US008431743B2

(12) United States Patent
Dieterle et al.

(10) Patent No.: US 8,431,743 B2
(45) Date of Patent: Apr. 30, 2013

(54) PREPARATION OF ACRYLIC ACID BY HETEROGENEOUSLY CATALYZED PARTIAL GAS PHASE OXIDATION OF PROPYLENE

(75) Inventors: Martin Dieterle, Mannheim (DE); Klaus Joachim Mueller-Engel, Stutensee (DE); Claus Hechler, Ludwigshafen (DE); Ulrich Hammon, Mannheim (DE); Armin Diefenbacher, Germersheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 632 days.

(21) Appl. No.: 11/131,256

(22) Filed: May 18, 2005

(65) Prior Publication Data

US 2006/0004229 A1 Jan. 5, 2006

Related U.S. Application Data

(60) Provisional application No. 60/678,774, filed on May 9, 2005, provisional application No. 60/662,804, filed on Mar. 18, 2005, provisional application No. 60/657,374, filed on Mar. 2, 2005, provisional application No. 60/657,407, filed on Mar. 2, 2005, provisional application No. 60/656,874, filed on Mar. 1, 2005, provisional application No. 60/656,875, filed on Mar. 1, 2005, provisional application No. 60/584,469, filed on Jul. 1, 2004.

(30) Foreign Application Priority Data

| Jul. 1, 2004 | (DE) | 10 2004 032 129 |
| Mar. 1, 2005 | (DE) | 10 2005 009 885 |
| Mar. 1, 2005 | (DE) | 10 2005 009 891 |
| Mar. 2, 2005 | (DE) | 10 2005 010 111 |
| Mar. 18, 2005 | (DE) | 10 2005 013 039 |

(51) Int. Cl.
*C07C 51/42* (2006.01)

(52) U.S. Cl.
USPC .......... 562/600; 562/54; 562/512.2; 562/598; 562/599

(58) Field of Classification Search ................. 562/545, 562/512.2
See application file for complete search history.

(56) References Cited

U.S. PATENT DOCUMENTS

| 3,161,670 A | 12/1964 | Adams et al. |
| 4,317,926 A | 3/1982 | Sato et al. |
| 4,413,147 A | 11/1983 | Khoobiar |
| 4,532,365 A | 7/1985 | Khoobiar |
| 4,535,188 A | 8/1985 | Khoobiar |
| RE32,082 E | 2/1986 | Khoobiar |
| 5,198,578 A | 3/1993 | Etzkorn et al. |
| 5,426,221 A | 6/1995 | Willersinn |
| 5,637,222 A | 6/1997 | Herbst et al. |
| 5,705,684 A | 1/1998 | Hefner et al. |
| 5,780,679 A | 7/1998 | Egly et al. |
| 5,831,124 A | 11/1998 | Machhammer et al. |
| 5,897,749 A | 4/1999 | Kroker et al. |
| 6,207,022 B1 | 3/2001 | Dockner et al. |
| 6,348,638 B1 | 2/2002 | Schliephake et al. |
| 6,350,906 B2 | 2/2002 | Machhammer et al. |
| 6,395,936 B1 | 5/2002 | Arnold et al. |
| 6,403,829 B1 | 6/2002 | Unverricht et al. |
| 6,413,379 B1 | 7/2002 | Machhammer et al. |
| 6,423,875 B1 | 7/2002 | Machhammer et al. |
| 6,426,433 B1 | 7/2002 | Machhammer et al. |
| 6,448,439 B1 | 9/2002 | Eck et al. |
| 6,492,548 B1 * | 12/2002 | Brockwell et al. ............ 562/545 |
| 6,498,272 B1 | 12/2002 | Schroeder et al. |
| 6,525,217 B1 | 2/2003 | Unverricht et al. |
| 6,555,707 B1 | 4/2003 | Nestler et al. |
| 6,596,901 B1 | 7/2003 | Eck et al. |
| 6,646,161 B1 | 11/2003 | Eck et al. |
| 6,679,939 B1 | 1/2004 | Thiel et al. |
| 6,727,383 B1 | 4/2004 | Nestler et al. |
| 6,781,017 B2 | 8/2004 | Machhammer et al. |
| 6,888,024 B2 | 5/2005 | Dieterle et al. |
| 6,939,991 B2 | 9/2005 | Thiel et al. |
| 6,956,901 B2 | 10/2005 | Boroczky et al. |
| 7,294,741 B2 | 11/2007 | Bub et al. |
| 2001/0007043 A1 | 7/2001 | Machhammer et al. |
| 2002/0178389 A1 | 11/2002 | Satoh |
| 2003/0060661 A1 | 3/2003 | Eck et al. |
| 2003/0175159 A1 | 9/2003 | Heilek et al. |
| 2003/0187299 A1 | 10/2003 | Machhammer et al. |
| 2004/0063988 A1 | 4/2004 | Hechler et al. |
| 2004/0063989 A1 | 4/2004 | Hechler et al. |
| 2004/0097756 A1 | 5/2004 | Thiel et al. |
| 2004/0116736 A1 | 6/2004 | Machhammer et al. |
| 2004/0116741 A1 | 6/2004 | Nordhoff et al. |
| 2004/0138501 A1 | 7/2004 | Thiel et al. |
| 2004/0181083 A1 | 9/2004 | Proll et al. |
| 2004/0191953 A1 | 9/2004 | Dieterle et al. |
| 2004/0192963 A1 | 9/2004 | Dieterle et al. |
| 2004/0192964 A1 | 9/2004 | Petzoldt et al. |
| 2004/0192965 A1 | 9/2004 | Petzoldt et al. |
| 2004/0199001 A1 | 10/2004 | Schindler et al. |
| 2004/0225158 A1 | 11/2004 | Dieterle et al. |
| 2004/0242826 A1 | 12/2004 | Nishimura |
| 2004/0249196 A1 | 12/2004 | Dieterle et al. |
| 2004/0256319 A1 | 12/2004 | Hammon et al. |
| 2004/0260121 A1 | 12/2004 | Nestler et al. |
| 2005/0006299 A1 | 1/2005 | Heilek et al. |
| 2005/0090628 A1 | 4/2005 | Eck et al. |
| 2005/0101803 A1 | 5/2005 | Dieterle et al. |
| 2005/0119515 A1 | 6/2005 | Machhammer et al. |
| 2005/0171380 A1 | 8/2005 | Bub et al. |

FOREIGN PATENT DOCUMENTS

| DE | 33 13 573 A1 | 10/1983 |
| DE | 43 08 087 A1 | 9/1994 |

(Continued)

OTHER PUBLICATIONS

Foreign Search Report, ROC (Taiwan) Patent Application No. 094114839, Dec. 27, 2010.

*Primary Examiner* — Sudhakar Katakam
(74) *Attorney, Agent, or Firm* — Oblon, Spivak, McClelland, Maier & Neustadt, L.L.P.

(57) ABSTRACT

The present invention relates to a process for preparing acrylic acid by two-stage heterogeneously catalyzed partial gas phase oxidation of propylene, in which the propylene source used is a preceding propane dehydrogenation and in which the first oxidation stage is operated with restricted propylene conversion, and unconverted propane and propylene present in the product gas mixture of the second partial oxidation stage are recycled substantially into the preceding propane dehydrogenation.

32 Claims, No Drawings

FOREIGN PATENT DOCUMENTS

| | | |
|---|---|---|
| DE | 43 35 172 A1 | 4/1995 |
| DE | 44 36 243 A1 | 4/1996 |
| DE | 195 01 325 A1 | 7/1996 |
| DE | 195 08 558 A1 | 9/1996 |
| DE | 196 06 877 A1 | 8/1997 |
| DE | 196 27 847 A1 | 1/1998 |
| DE | 197 40 252 A1 | 3/1999 |
| DE | 197 40 253 A1 | 3/1999 |
| DE | 198 37 517 A1 | 2/2000 |
| DE | 198 37 519 A1 | 2/2000 |
| DE | 198 37 520 A1 | 2/2000 |
| DE | 100 53 086 | 10/2000 |
| DE | 199 24 532 A1 | 11/2000 |
| DE | 199 24 533 A1 | 11/2000 |
| DE | 199 48 248 A1 | 4/2001 |
| DE | 101 31 297 A1 | 1/2003 |
| DE | 102 35 847 A1 | 8/2003 |
| DE | 102 11 275 A1 | 9/2003 |
| DE | 102 23 058 A1 | 12/2003 |
| DE | 103 13 209 A1 | 3/2004 |
| DE | 103 36 386 A1 | 3/2004 |
| DE | 102 43 625 A1 | 4/2004 |
| DE | 102 45 585 A1 | 4/2004 |
| DE | 102 46 119 A1 | 4/2004 |
| DE | 102 47 240 A1 | 4/2004 |
| DE | 103 32 758 A1 | 5/2004 |
| DE | 103 16 039 A1 | 10/2004 |
| DE | 10 2004 025 445 A1 | 2/2005 |
| DE | 10 2004 032 129 A1 | 3/2005 |
| DE | 10 2004 021 763 A1 | 5/2005 |
| DE | 10 2004 021 764 A1 | 6/2005 |
| DE | 103 51 269 A1 | 6/2005 |
| EP | 0 117 146 | 8/1984 |
| EP | 0 274 681 A1 | 7/1988 |
| EP | 0 293 224 A1 | 11/1988 |
| EP | 0 695 736 A1 | 2/1996 |
| EP | 0 792 867 A2 | 9/1997 |
| EP | 0 854 129 A1 | 7/1998 |
| EP | 0 920 408 B1 | 6/1999 |
| EP | 0 925 272 B1 | 6/1999 |
| EP | 0 982 287 A1 | 3/2000 |
| EP | 0 982 288 A2 | 3/2000 |
| EP | 0 982 289 A2 | 3/2000 |
| EP | 0 990 636 A1 | 4/2000 |
| EP | 1 015 410 B1 | 7/2000 |
| EP | 1 015 411 B1 | 7/2000 |
| EP | 1 041 062 A2 | 10/2000 |
| EP | 1 066 239 B1 | 1/2001 |
| EP | 1 066 240 B1 | 1/2001 |
| EP | 1 068 174 B1 | 1/2001 |
| EP | 1 070 700 A2 | 1/2001 |
| EP | 1 106 598 A2 | 6/2001 |
| EP | 1 180 508 A1 | 2/2002 |
| EP | 101 15 277 A1 | 6/2002 |
| EP | 1 388 532 A1 | 2/2004 |
| EP | 1 388 533 A1 | 2/2004 |
| EP | 1 484 303 A2 | 12/2004 |
| EP | 1 484 308 A1 | 12/2004 |
| EP | 1 484 309 A1 | 12/2004 |
| TW | 20040975 | 6/2004 |
| TW | 255811 | 6/2006 |
| WO | WO 97/36849 | 10/1997 |
| WO | WO 97/48669 | 12/1997 |
| WO | WO 98/01415 | 1/1998 |
| WO | WO 99/14181 | 3/1999 |
| WO | WO 99/14182 | 3/1999 |
| WO | WO 99/50219 | 10/1999 |
| WO | WO 99/50220 | 10/1999 |
| WO | WO 99/50222 | 10/1999 |
| WO | WO 00/53556 | 9/2000 |
| WO | WO 00/53557 | 9/2000 |
| WO | WO 00/53558 | 9/2000 |
| WO | WO 00/53559 | 9/2000 |
| WO | WO 00/53560 | 9/2000 |
| WO | WO 00/53561 | 9/2000 |
| WO | WO 01/77056 A1 | 10/2001 |
| WO | WO 01/96270 A2 | 12/2001 |
| WO | WO 01/96271 A2 | 12/2001 |
| WO | WO 02/09839 A1 | 2/2002 |
| WO | WO 02/055469 A1 | 7/2002 |
| WO | WO 03/011804 A2 | 2/2003 |
| WO | WO 03/029177 A1 | 4/2003 |
| WO | WO 03/041832 A1 | 5/2003 |
| WO | WO 03/041833 A1 | 5/2003 |
| WO | WO 03/076370 A1 | 9/2003 |
| WO | WO 03/078378 A1 | 9/2003 |
| WO | WO 2004/031106 A1 | 4/2004 |
| WO | WO 2004/035514 A1 | 4/2004 |
| WO | WO 2004/063138 A1 | 7/2004 |
| WO | WO 2004/085362 A1 | 10/2004 |
| WO | WO 2004/085363 A1 | 10/2004 |
| WO | WO 2004/085365 A2 | 10/2004 |
| WO | WO 2004/085367 A1 | 10/2004 |
| WO | WO 2004/085369 A1 | 10/2004 |
| WO | WO 2004/085370 A1 | 10/2004 |

* cited by examiner

PREPARATION OF ACRYLIC ACID BY HETEROGENEOUSLY CATALYZED PARTIAL GAS PHASE OXIDATION OF PROPYLENE

TITLE OF THE INVENTION

BACKGROUND OF THE INVENTION

1. Field of the Invention

The present invention relates to a process for preparing acrylic acid by heterogeneously catalyzed partial gas phase oxidation of propylene, by a) in a first reaction stage, subjecting propane to a homogeneous and/or a heterogeneously catalyzed dehydrogenation and/or oxydehydrogenation in the presence of and/or with exclusion of oxygen to obtain a product gas mixture 1 comprising propane and propylene, and b) if appropriate removing and/or converting to other compounds a portion of the constituents, other than propane and propylene, present in the product gas mixture 1 formed in the first reaction stage to obtain a product gas mixture 1' from product gas mixture 1, and c) subjecting product gas mixture 1 and/or product gas mixture 1', as a constituent of a starting reaction gas mixture 2 which comprises molecular oxygen and propylene in a molar $O_2:C_3H_6$ ratio of $\geq 1$, to a heterogeneously catalyzed partial gas phase oxidation of propylene present in product gas mixture 1 and/or product gas mixture 1' to acrolein in a second reaction stage charged with a fixed catalyst bed 2 whose catalysts have at least one multimetal oxide comprising the elements Mo, Fe and Bi as an active composition to obtain a product gas mixture 2, and d) if appropriate lowering the temperature of the product gas mixture 2 leaving the second reaction stage by indirect and/or direct cooling and if appropriate adding molecular oxygen and/or inert gas to product gas mixture 2, and e) then subjecting it, as a starting reaction gas mixture 3 which comprises acrolein, molecular oxygen and at least one inert gas and comprises molecular oxygen and acrolein in a molar $O_2:C_3H_4O$ ratio of $\geq 0.5$, to a heterogeneously catalyzed partial gas phase oxidation of acrolein present in starting reaction gas mixture 3 to acrylic acid in a third reaction stage charged with a fixed catalyst bed 3 whose catalysts have at least one multimetal oxide comprising the elements Mo and V as an active composition to obtain a product gas mixture 3, and f) removing acrylic acid in a separating zone A from the product gas mixture 3 and recycling at least the unconverted propane and propylene present in product gas mixture 3 to an extent of in each case at least 80 mol % based on the particular amount present in product gas mixture 3 into at least the first of the three reaction stages.

2. Driscription of the Background

Acrylic acid is an important monomer which finds use as such or in the form of its alkyl esters for obtaining polymers suitable, for example, as adhesives.

It is known that acrylic acid can be prepared by two-stage heterogeneously catalyzed partial gas phase oxidation of propylene (cf., for example, EP-A 990 636, U.S. Pat. No. 5,198,578, EP-A 10 15 410, EP-A 14 84 303, EP-A 14 84 308, EP-A 14 84 309 and U.S. 2004/0242826).

It is characteristic of the aforementioned processes that the acrylic acid is not obtained as such, but rather as a constituent of a product gas mixture from which it subsequently has to be removed.

It is common to substantially all separation processes known in this regard that, if appropriate after direct and/or indirect cooling of the aforementioned product gas mixture, acrylic acid present in the product gas mixture is converted to the condensed phase in a basic removal step. This may be effected, for example, by absorption into a suitable solvent (for example water, high-boiling organic solvents, aqueous solutions) and/or by partial or substantially full condensation (for example by fractional condensation) (on this subject, cf., for example, the abovementioned documents, and the documents EP-A 13 88 533, EP-A 13 88 532, DE-A 102 35 847, EP-A 79 28 67, WO 98/01415, EP-A 10 15 411, EP-A 10 15 410, WO 99/50219, WO 00/53560, WO 02/09839, DE-A 102 35 847, WO 03/041833, DE-A 102 23 058, DE-A 102 43 625, DE-A 103 36 386, EP-A 85 41 29, U.S. Pat. No. 4,317,926, DE-A 198 37 520, DE-A 196 06 877, DE-A 19 50 1325, DE-A 102 47 240, DE-A 197 40 253, EP-A 69 57 36, EP-A 98 22 87, EP-A 10 41 062, EP-A 11 71 46, DE-A 43 08 087, DE-A 43 35 172, DE-A 44 36 243, DE-A 19 924 532, DE-A 103 32 758 and DE-A 19 924 533). An acrylic acid removal may also be undertaken as described in EP-A 98 22 87, EP-A 98 22 89, DE-A 103 36 386, DE-A 101 15 277, DE-A 196 06 877, DE-A 197 40 252, DE-A 196 27 847, EP-A 92 04 08, EP-A 10 68 174, EP-A 10 66 239, EP-A 10 66 240, WO 00/53560, WO 00/53561, DE-A 100 53 086 and EP-A 98 22 88. Favorable modes of removal are also the processes described in the documents WO 2004/063138, WO 2004/035514, DE-A 102 43 625 and DE-A 102 35 847.

The condensed phase which comprises acrylic acid and is obtained in the basic removal described may then be further purified, for example, by extraction, rectification, desorption and/or crystallization to the desired degree of purity of the acrylic acid. For example, the further purification may be effected as described in the documents WO 01/77056, WO 03/041832, WO 02/055469, WO 03/078378 and WO 03/041833.

A common feature of the basic removals described is that a residual gas stream (cf. also EP-A 11 80 508) normally remains (typically at the top of the separating column which comprises separating internals and is used for the basic removal), which comprises substantially those constituents of the product gas mixture whose boiling point at standard pressure (1 bar) is $\leq -30°$ C. (i.e. the constituents which are difficult to condense or else highly volatile). The residual gas constituents are primarily reactants unconsumed in the partial oxidation, i.e. molecular oxygen (is generally used in excess relative to the stoichiometry of the partial oxidation in order to modify the catalyst activity advantageously) and in some cases propylene, and in particular inert diluent gases used in the partial oxidation, for example nitrogen, noble gases, carbon oxides and saturated hydrocarbons. Depending on the separation process employed, steam may be present in the residual gas only in traces or in amounts of up to 20% by volume, or up to 25% by volume or more. In small amounts, the residual gas may also comprise acrylic acid and/or acrolein which are normally, however, predominantly basically removed as described.

A disadvantage of the remaining residual gas is that it can be recycled into the partial oxidation only in a limited amount. More substantial recycling is not possible because the cycle gas constituents would otherwise accumulate in such a cycle gas mode. This would have the consequence of reaction gas streams in the partial oxidation which are no longer manageable and finally the extinguishing of the partial oxidation. In general, at most half of the residual gas is therefore recycled as oxidation cycle gas into the partial oxidation and the remaining amount is sent to combustion as outlet gas (cf., for example, EP-A 925 272).

Among other reasons, the aforementioned is disadvantageous because propylene which has not been converted in the partial oxidation and remains in the residual gas is necessarily lost (a propylene removal from the residual gas and subsequent separate recycling of the removed propylene into the partial oxidation is of low economic viability owing to the small fractions of propylene).

The disadvantageousness is so great in particular because the starting propylene used for the acrylic acid preparation is normally propylene having a comparatively high purity (for example polymer-grade or chemical-grade propylene; cf. DE-A 101 31 297), which has normally passed through a separation from the other hydrocarbons, for example propane, which accompany it as a result of the preparation.

For this reason among others, very high propylene conversions are therefore pursued in the first reaction stage (cf. WO 03/029177). The same also applies to the acrolein conversion in the second reaction stage. This is the case additionally because acrolein which has not been converted in the second reaction stage becomes noticeably disadvantageous, for example, in the removal of acrylic acid from the product gas mixture of the partial oxidation (undesirably promotes the polymerization tendency of acrylic acid (cf., for example, DE-A 10 2004 021 763 and DE-A 10 2004 021 706)). In order to obtain the aforementioned high conversions, the prior art even recommends the use of postreactors (cf., for example, DE-A 10 2004 021 763 and DE-A 10 2004 021 706).

In particular on the industrial scale of the two-stage partial oxidation of propylene to acrylic acid, propylene conversions of >99.5 mol % are in many cases pursued in the first reaction stage in order to be able to fully dispense with an oxidation cycle gas recycling into the partial oxidation. Such an operating mode additionally includes the advantage that the energy required for the oxidation cycle gas recycling (the oxidation cycle gas has to be recompressed to partial oxidation pressure by means of a turbocompressor before the recycling) and the not inconsiderable investment in the compressor (for example one of the model 12 MH4B from Mannesmann DEMAG, Germany) is not required.

However, high conversions typically require catalysts which are highly tuned with regard to their activity and/or high temperatures in the partial oxidation. Both have a disadvantageous effect on the catalyst lifetime (cf. DE-A 103 51 269 and DE-A 10 2004 025 445). This is the case in particular because the reaction gas mixture passes through a maximum value, known as the hotspot value, as it flows through the fixed catalyst bed in each of the two partial oxidation stages.

For reasons of convenience, the temperature of the fixed catalyst bed and the effective temperature of the fixed catalyst bed are therefore distinguished from one another. The temperature of the fixed catalyst bed refers to the temperature of the fixed catalyst bed when the partial oxidation process is being performed, but in the theoretical absence of a chemical reaction (i.e. without the influence of the heat of reaction). In contrast, the effective temperature of the fixed catalyst bed refers to the actual temperature of the fixed catalyst bed including the heat of reaction of the partial oxidation. When the temperature of the fixed catalyst bed is not constant along the fixed catalyst bed (for example in the case of a plurality of temperature zones), the term temperature of the fixed catalyst bed means the (numerical) average of the temperature along the fixed catalyst bed. The temperature of the fixed catalyst bed over its length may of course also be configured in such a way that the temperature is constant over a certain length, then changes abruptly and maintains this new value over a further length, etc. In that case, reference is made to a fixed catalyst bed (fixed bed catalyst charge) having more than one temperature zone (or else reaction zone), or disposed in more than one temperature zone (or else reaction zone). Catalyst-charged reactors which implement such temperature zones (or else reaction zones) are correspondingly referred to as one-zone or multizone reactors (cf., for example, WO 04/085369). In common with the temperature of the reaction gas mixtures, the effective temperature of the fixed catalyst bed likewise passes through the hotspot value in flow direction of the reaction gas mixture.

It is possible to make use of the possibility of lowering the hotspot temperature by operating the partial oxidation process at reduced reactant conversion in the conventional, above-described propylene partial oxidation to acrylic acid at best with considerable disadvantages for the above-described reasons.

SUMMARY OF THE INVENTION

It is therefore an object of the present invention to provide a process for preparing acrylic acid by heterogeneously catalyzed partial gas phase oxidation of propylene, which at worst still has the disadvantages described in reduced form at least in the first reaction stage (propylene->acrolein).

Accordingly, a process has been found for preparing acrylic acid by heterogeneously catalyzed partial gas phase oxidation of propylene, by
a) in a first reaction stage, subjecting propane to a homogeneous and/or a heterogeneously catalyzed dehydrogenation and/or oxydehydrogenation in the presence of and/or with exclusion of oxygen to obtain a product gas mixture 1 comprising propane and propylene, and
b) if appropriate removing and/or converting to other compounds a portion of the constituents, other than propane and propylene, present in the product gas mixture 1 formed in the first reaction stage to obtain a product gas mixture 1' from product gas mixture 1, and
c) subjecting product gas mixture 1 and/or product gas mixture 1', as a constituent of a starting reaction gas mixture (2-$a$) which comprises molecular oxygen and propylene in a molar $O_2:C_3H_6$ ratio of $\geqq 1$, to a heterogeneously catalyzed partial gas phase oxidation of propylene present in product gas mixture 1 and/or product gas mixture 1' to acrolein in a second reaction stage charged with a fixed catalyst bed (2-$b$) whose catalysts have at least one multimetal oxide comprising the elements Mo, Fe and Bi as an active composition to obtain a product gas mixture (2-$c$), and
d) if appropriate lowering the temperature of the product gas mixture (2-$c$) leaving the second reaction stage by indirect and/or direct cooling and if appropriate adding molecular oxygen and/or inert gas to product gas mixture (2-$c$), and then
e) subjecting it, as a starting reaction gas mixture (3-$a$) which comprises acrolein, molecular oxygen and at least one inert gas and comprises molecular oxygen and acrolein in a molar $O_2:C_3H_4O$ ratio of $\geqq 0.5$, to a heterogeneously catalyzed partial gas phase oxidation of acrolein present in starting reaction gas mixture 3 to acrylic acid in a third reaction stage charged with a fixed catalyst bed (3-$b$) whose catalysts have at least one multimetal oxide comprising the elements Mo and V as an active composition to obtain a product gas mixture (3-$c$), and
f) removing acrylic acid in a separating zone A from product gas mixture (3-$c$) and recycling at least the unconverted propane and propylene present in product gas mixture 3 to an extent of in each case at least 80 mol % based on the particular amount present in product gas mixture (3-c) into at least the first of the three reaction stages, wherein the conversion $C^P$ of propylene in the second reaction stage, based on single pass through it, is ≦99.5 mol %, and the conversion $C^A$ of acrolein in the third reaction stage, based on single pass through it, is ≧96 mol %, and the process has at least one, preferably separate, discharge for constituents other than propane and propene. Separate means here that the at least one discharge is effected preferably without accompaniment of propane and propene. In other words, the content of propane and propene in the at least one outlet gas is preferably at values of ≦5, better ≦1% by volume, or better at ≦0.5% by volume, or ≦0.25% by volume, or ≦0.1% by volume.

DETAILED DESCRIPTION OF THE PREFERRED EMBODIMENTS

In addition to the advantages of the process according to the invention which have already been mentioned, it should be noted that a lower $C^P$ is accompanied by an increased selectivity of acrylic acid formation. Furthermore, the amount of catalyst required for fixed catalyst bed 2 falls to a disproportionately large extent with decreasing $C^P$, since the catalyst requirement accompanying increasing $C^P$ increases exponentially.

The basic idea of the process according to the invention, to use a partial propane dehydrogenation and/or a propane oxydehydrogenation as the propylene source for acrylic acid preparation and to recycle propane and propylene unconverted in the overall process at least partly into the propylene source, is known (cf., for example, DE-A 102 45 585, WO 01/96270, DE-A 10 2004 032 129, WO 03/076370, WO 01/96271, EP-A 117 146, WO 03/0118804, U.S. Pat. No. 3,161,670, DE-A 33 13 573, WO 04/031106, DE-A 103 16 039, DE-A 195 08 558, WO 03/11804, DE-A 198 37 520, DE-A 198 37 519, DE-A 198 37 517, WO 97/36849 and EP-A 1 106 598 and EP-A 274 681).

The potential (available as a result of the raw material switch to the substantially less expensive propane and the associated possibility of at least one, preferably separate, economically viable discharge for constituents other than propane (and propylene) with simultaneously very quantitative recycling of unconverted propane from the partial oxidation into the propylene source) of a reduced propylene conversion in the first reaction stage, accompanied by a subsequent very comprehensive propylene recycling proceeding with propane in the integrated system without additional cost and inconvenience, into the overall process has, however, not been seen to date.

According to the invention, it is therefore advantageous to carry out the process according to the invention in such a way that $C^P$≦99.0 mol % and $C^A$≧96 mol %, or better
$C^P$≦98.5 mol % and $C^A$≧96 mol %, or better
$C^P$≦98.0 mol % and $C^A$≧96 mol %, or better
$C^P$≦97.5 mol % and $C^A$≧96 mol %, or better
$C^P$≦97.0 mol % and $C^A$≧96 mol %, or better
$C^P$≦96.5 mol % and $C^A$≧96 mol %, or better
$C^P$≦96.0 mol % and $C^A$≧96 mol %, or better
$C^P$≦95.5 mol % and $C^A$≧96 mol %, or better
$C^P$≦95.0 mol % and $C^A$≧96 mol %, or better
$C^P$≦94.5 mol % and $C^A$≧96 mol %, or better
$C^P$≦94.0 mol % and $C^A$≧96 mol %, or better
$C^P$≦93.5 mol % and $C^A$≧96 mol %, or better
$C^P$≦93.0 mol % and $C^A$≧96 mol %, or better
$C^P$≦92.0 mol % and $C^A$≧96 mol %, or better
$C^P$≦91.0 mol % and $C^A$≧96 mol %, or better
$C^P$≦90.0 mol % and $C^A$≧96 mol %, or better
$C^P$≦85.0 mol % and $C^A$≧96 mol %, or better
$C^P$≦80.0 mol % and $C^A$≧96 mol %, or better
$C^P$≦75.0 mol % and $C^A$≧96 mol %.

In general, $C^P$ in all of the aforementioned pairs will be ≧50 mol %, preferably ≧60 mol %, advantageously ≧70 mol %.

Of course, $C^P$ may also be ≧75 mol %, or ≧80 mol %, or ≧85 mol %, or ≧90 mol %. In other words, a possible inventive $C^P$ range is any possible combination of an aforementioned $C^P$ lower limit with an aforementioned $C^P$ upper limit.

According to the invention, it is also advantageous when $C^A$ in each of the aforementioned $C^P$, $C^A$ pairs is ≧96.5 mol %, better ≧97 mol %, better ≧97.5 mol %, better ≧98 mol %, better ≧98.5 mol %, better ≧99 mol %, better ≧99.5 mol %, better ≧99.6 mol %, better ≧99.7 mol %, better ≧99.8 mol %, better ≧99.9 mol %, better ≧99.91 mol %, better ≧99.92 mol %, better ≧99.93 mol %, better ≧99.94 mol %, better ≧99.95 mol %, better ≧99.96 mol %, better ≧99.97 mol %, better ≧99.98 mol %, better ≧99.99 mol %.

The aforementioned maximum values can be attained, for example, when the third reaction stage comprises at least one postreactor according to DE-A 10 2004 021 764 or DE-A 10 2004 021 7063. Alternatively, process variants according to the prior art specified in these documents may be employed.

In general, $C^A$ will be <100 mol %, or not greater than 99.995 mol %. In many cases, $C^A$ will be ≦99.99 mol %, or ≧99.98 mol %, or ≦99.96 mol %, or ≦99.95 mol %. In other words, a possible inventive $C^A$ range is any possible combination of an aforementioned $C^A$ lower limit with an aforementioned $C^A$ upper limit. Since $C^P$ and $C^A$ in the process according to the invention may be adjusted independently of one another, it is also possible in accordance with the invention to freely combine the ranges for $C^P$ with the ranges for $C^A$. Advantageously, a preferred range for $C^P$ is combined with a preferred range for $C^A$.

Particularly advantageous in accordance with the invention is a $C^P$ of from 80 to 98 mol %, with a simultaneous $C^A$ of from 99.0 to 99.9 mol %. Another combination preferred in accordance with the invention is a $C^P$ of from 90 to 98 mol % with a simultaneous $C^A$ of from 99.0 to 99.9 mol % or more, or from 99.3 to 99.6 mol %.

It is also favorable for the process according to the invention, irrespective of $C^A$ and $C^P$, when, after the removal of the acrylic acid from product gas mixture 3 in separation zone A, the unconverted propane and propylene present in product gas mixture 3 are recycled to an extent of in each case at least 85 mol %, better to an extent of in each case at least 90 mol %, better to an extent of in each case at least 92 mol %, better to an extent of in each case at least 94 mol %, better to an extent of in each case at least 95 mol %, better to an extent of in each case at least 95.5 mol %, better to an extent of in each case at least 96 mol %, better to an extent of in each case at least 96.5 mol %, better to an extent of in each case at least 97 mol %, better to an extent of in each case at least 97.5 mol %, better to an extent of in each case at least 98 mol %, better to an extent of in each case at least 98.5 mol %, better to an extent of in each case at least 99 mol %, better to an extent of in each case at least 99.5 mol %, better to an extent of in each case at least 99.75 mol % or at least 99.9 mol % and at best quantitatively (based in each case on the particular amount of propane or propylene present in product gas mixture 3) at least into the first of the three reaction stages. According to the invention, the aforementioned propane and propene recycling is advantageously effected exclusively into the first reaction stage. However, it may also be effected partly (for example to an extent of up to 50% by weight, or to an extent of up to 30% by weight, or to an extent of up to 20% by weight, or to an extent of up to 10% by weight, or to an extent of up to 5% by weight or less) into the second and/or third reaction stage.

In the case of the second reaction stage, the point of addition may be into a $C_3$ removal disposed between the first and the second reaction stage (for example as stripping gas).

Appropriately in accordance with the invention, the aforementioned recycling of propane and propylene will be carried out in an integrated system, i.e. in the same recycle gas. Such recycle gases will be referred to below as $C_3$ cycle gases.

In the simplest case, $C_3$ cycle gas may be oxidation cycle gas. In other words, the acrylic acid present as the target product in product gas mixture 3 will be converted in separation zone A from the gaseous into the condensed phase, for example by absorptive and/or condensative measures. Useful absorbents are, for example, water and/or organic solvents (especially hydrophobic organic solvents which have a higher boiling point than acrylic acid under standard conditions (25° C., 1 bar) (in principle, the removal (condensation) may be undertaken as described in EP-A 117146, DE-A 4308087, DE-A 4335172, DE-A 4436243, DE-A 19924533, EP-A 982287, EP-A 982289, DE-A 19924532, DE-A 10115277, DE-A 19606877, DE-A 19740252, DE-A 19627847, DE-A 10053086 and EP-A 982288; preference is given to removing as described in FIG. 7 of WO 0196271 and as described in DE-A 102004032129 and the equivalents thereof)). In the course of this "condensation" of acrylic acid, as already described at the outset, a residual gas which is not transferred to the condensed phase normally remains (oxidation cycle gas) which comprises the constituents of product gas mixture 3 which are comparatively (compared with acrylic acid) difficult to "condense". These are, as already stated, generally those components whose boiling point at standard pressure (1 bar) is $\leq -30°$ C. (their total portion in the oxidation residual gas is generally $\geq 70\%$ by volume, frequently $\geq 80\%$ by volume and in many cases $\geq 90\%$ by volume).

In the process according to the invention, product gas mixture 3 is generally composed substantially of the acrylic acid target product, unconverted molecular oxygen, propane, unconverted propylene, molecular nitrogen, steam which has formed as a by-product and/or has been used as a diluent gas, carbon oxides which have been formed as a by-product and/or have been used as a diluent gas, residual amounts of acrolein, and small amounts of other lower aldehydes, lower alkanecarboxylic acids (e.g. acetic acid, formic acid and propionic acid), and maleic anhydride, benzaldehyde, aromatic carboxylic acids and aromatic carboxylic anhydrides (e.g. phthalic anhydride and benzoic acid), and in some cases further hydrocarbons and other inert diluent gases.

According to that which has been described above, the oxidation cycle gas includes, according to the invention, primarily unconverted propane, unconverted propylene and generally $O_2$ and inert diluent gases, for example other saturated hydrocarbons such as methane, ethane, but also $N_2$, $CO_2$, noble gases. (He, Ne, Ar etc.), CO, and to a small extent also acrylic acid and acrolein, and in some cases acetic acid, formaldehyde and formic acid and also ethylene. Its steam content may be up to 25% by volume, frequently only up to 20% by volume, or only up to 10% by volume, but in many cases only below 10% by volume or below 5% by volume. Other lower aldehydes and alkanecarboxylic acids may equally be present in small amounts.

In other words, oxidation cycle gas generally consists predominantly of the inert diluent gases used for the two partial oxidation stages and of steam which is typically formed as a by-product in the partial oxidation or has been added as diluent gas, and carbon oxides formed by undesired full oxidation.

According to the invention, the oxidation cycle gas may then be recycled as such (and the propane and propylene present therein with it) into the first reaction stage (into reaction stage 1). However, it is also of course possible to remove the propane and propylene present therein from other constituents beforehand and thus to recycle them alone or in the presence of fewer secondary components into the first reaction stage. In the latter case, there would be a first discharge for constituents other than propane and propylene from the process according to the invention at this point.

Such a removal of propane and propylene may be effected, for example, by absorption with subsequent desorption and/or stripping (and absorbent reuse) in a high-boiling hydrophobic organic solvent (e.g. tetradecane). Further separation means are adsorption, rectification, membrane processes and partial condensation. Preference is given to performing the separating processes mentioned at elevated pressure.

When dehydrogenation catalysts are used which are sensitive toward oxygen or oxygen-containing compounds, these oxygenates will be removed from the propane and propylene before they are recycled. Such an oxygen removal may also be sensible in order to prevent combustion of propane and/or propylene at the recycle point into the dehydrogenation stage. The dehydrogenation catalysts of DE-A 19 937 107 are not sensitive toward oxygenates (especially those according to example 1 to 4 of the DE-A).

Another removal means is offered by fractional distillation. Preference is given to carrying out a fractional pressure distillation at low temperatures. The pressure to be employed may be from 10 to 100 bar. The rectification columns used may be columns having random packing, trays or structured packing. Suitable tray columns are those having dual-flow trays, bubble-cap trays or valve trays. The reflux ratio may be, for example, from 1 to 10. Other separation means are, for example, pressure extraction, pressure swing adsorption, pressure scrubbing, partial condensation and pressure extraction.

If the $C_3$ cycle gas still comprises carbon monoxide before it is recycled into the first reaction stage, this may be combusted catalytically to $CO_2$ before the recycling. The $CO_2$ formed can then be removed in a comparatively simple by scrubbing with a basic liquid.

It is of course also possible to proceed in such a way that only a portion of the oxidation cycle gas is recycled with an unchanged composition into the first reaction stage and propane and propylene are removed in a mixture (in an integrated system) only from the remaining portion and likewise recycled into the first reaction stage (as already mentioned previously, all propane/propylene recyclings described may also be effected partly into the second and/or into the third reaction stage).

In a removal of propane and propylene by fractional distillation of the oxidation cycle gas, a separation line may be defined, for example, in such a way that, in the rectifying section of the rectification column, substantially all of those constituents are removed and drawn off at the top of the column whose boiling point is lower than the boiling point of propylene. These constituents will primarily be the carbon oxides CO and $CO_2$, and also unconverted oxygen and ethylene, and methane, ethane and $N_2$. In the bottom, constituents having a higher boiling point than propylene and propane may be removed.

When, in the first reaction stage of the process according to the invention, a heterogeneously catalyzed oxydehydrogenation of propane is employed, a discharge of secondary components other than propane and propylene may always also be carried out when removals of molecular nitrogen are undertaken as in the documents DE-A 19837520, DE-A 19837517, DE-A 19837519 and DE-A 19837518.

The above-described oxidation cycle gas forms (based on the amount of propane and propylene present therein) the majority (normally at least 80% by weight, or at least 90% by weight, or at least 95% by weight or more) of all $C_3$ cycle gases of a process according to the invention, which is why it and the cycle gas streams which comprise propane and propylene and may be obtained therefrom by secondary component removal are also referred to as main $C_3$ cycle gas.

Especially when the acrylic acid is condensed by absorption by means of an organic solvent, generally at least one second residual gas comprising unconverted propane and unconverted propylene is generally obtained in separation zone A and is likewise advantageously treated in accordance with the invention as $C_3$ cycle gas. Based on propane and propylene present therein, its amount is normally substantially smaller in comparison to the main $C_3$ cycle gas. This can be attributed to the absorbate which forms also taking up propane and propylene to a certain extent in addition to acrylic acid. In the further course of the extractive, distillative, crystallizative and/or desorptive removal of the acrylic acid from the condensed phase or from the absorbate, this unconverted propane and propylene are advantageously recovered in accordance with the invention as a constituent of at least one further gas phase and recycled as further $C_3$ cycle gas. Before the recycling, as described for the main $C_3$ cycle gas, a secondary component removal may be undertaken as a further possible secondary component discharge (irrespective of whether such a secondary component removal has been undertaken or not, the term secondary $C_3$ cycle gas is used for these recycled $C_3$ cycle gases).

The secondary $C_3$ cycle gases may be recycled independently or in a mixture with main $C_3$ cycle gas. For the latter, the term total $C_3$ cycle gas is used. Secondary $C_3$ cycle gases may be oxygen-free or else oxygen-containing. The latter is the case, for example, when it is obtained by stripping by means of air or at the top of a rectification column flushed by means of air as a polymerization inhibitor. Advantageously, the secondary $C_3$ cycle gases may also be fed, owing to their limited amount, directly to starting reaction gas mixture 2 (preferred) and/or to starting reaction gas mixture 3.

According to the invention, preference is given to recycling the $C_3$ cycle gases into reaction stage 1 into starting reaction gas mixture 1 which is used to charge reaction stage 1 and also comprises fresh propane required for the process according to the invention. However, it may also be recycled into reaction stage 1 along the dehydrogenation conversion, as recommended by DE-A 102004032129.

In this document, fresh propane refers to propane which has not yet taken part in any chemical reaction. In general, it will be crude propane (which preferably fulfills the specification according to DE-A 102 46 119 and DE-A 102 45 585) which also comprises small amounts of components other than propane.

In this document, the starting reaction gas mixture 2 for the propylene partial oxidation to acrolein appropriately likewise fulfils the specifications recommended in DE-A 102 46 119 and DE-A 102 45 585.

In contrast to the exothermic, homogeneous or heterogeneously catalyzed oxydehydrogenation which is forced by the presence of oxygen and in which free hydrogen is neither formed as an intermediate (the hydrogen pulled from the propane to be dehydrogenated is pulled out directly as water ($H_2O$)) nor is detectable, a heterogeneously catalyzed dehydrogenation refers to a ("conventional") dehydrogenation whose thermal character, in contrast to the oxydehydrogenation, is endothermic (an exothermic hydrogen combustion may be included in the heterogeneously catalyzed dehydrogenation as a subsequent step) and in which free molecular hydrogen is formed at least as an intermediate. This generally requires different reaction conditions and different catalysts from the oxydehydrogenation.

The hourly space velocity on a catalyst bed, catalyzing a reaction step, of (starting) reaction gas mixture refers in this document to the amount of (starting) reaction gas mixture in standard liters (=l (STP); the volume in liters that the appropriate amount of (starting) reaction gas mixture would take up under standard conditions (0° C., 1 bar)) which is conducted per hour through one liter of fixed catalyst bed.

The hourly space velocity may also be based only on one constituent of the (starting) reaction gas mixture. In that case, it is the amount of this constituent in l (STP)/l·h which is conducted per hour through one liter of the catalyst bed (pure inert material charges are not included in the fixed catalyst bed).

In this document, an inert gas refers to a reaction gas constituent which behaves substantially inertly under the conditions of the reaction and, each of the inert reaction gas constituents viewed alone, remains chemically unchanged to an extent of more than 95 mol %, preferably to an extent of more than 99 mol %.

In principle, the propylene content of starting reaction gas mixture 2, with a view to satisfactory space-time yields, will be ≧4% by volume. However, the inventive procedure is advantageous especially when the propylene content of starting reaction gas mixture 2 is ≧7% by volume.

Normally, the aforementioned propylene content will be ≦15% by volume. Preference is given in accordance with the invention to propylene contents of starting reaction gas mixture 2 of from 7 to 12% by volume, more preferably from 7 to 11% by volume and most preferably from 7 to 10% by volume or from 7 to 9% by volume. The propylene content, preferred in accordance with the invention, of starting reaction gas 2 is 8% by volume.

It is also generally advantageous for the process according to the invention when the molar ratio $V_1$ of propane present in starting reaction gas mixture 2 to propylene present in starting reaction gas mixture 2 is from 1 to 4. Preferably, $V_1$=from 1 to 3.5, more preferably from 1 to 3.0 or from 1 to 2.5, and most preferably $V_1$=from 1.5 to 2.2. It is also generally advantageous for the process according to the invention when the molar ratio of molecular nitrogen present in starting reaction gas mixture 2 to molecular oxygen present in starting reaction gas mixture 2 is from 2 to 6, preferably from 3 to 4.5, more preferably from 3.5 to 4.5 and most preferably from 3.5 to 4 or 3.73.

Furthermore, it is generally advantageous for the process according to the invention when the molar ratio $V_3$ of molecular oxygen present in starting reaction gas mixture 2 to propylene present in starting reaction gas mixture 2 is from 1.3 to 2.4, preferably from 1.4 to 2.2, more preferably from 1.4 to 2.1 and most preferably from 1.5 to 2.1 or from 1.7 to 2.1 or 1.9.

Possible inventive starting reaction gas mixtures 2 comprise
from 6 to 9% by volume of propylene,
from 8 to 18% by volume of molecular oxygen,
from 6 to 30% by volume of propane and
from 32 to 72% by volume of molecular nitrogen
where
$V_1$=from 1 to 4,
$V_2$=from 2 to 6 and
$V_3$=from 1.3 to 2.4.

Preferred inventive starting reaction gas mixtures 2 comprise
from 7 to 9% by volume of propylene,
from 9.8 to 16% by volume of molecular oxygen,
from 9 to 25% by volume of propane and
from 35 to 65% by volume of molecular nitrogen,
where
$V_1$=from 1 to 3.5,
$V_2$=from 3 to 4.5 and
$V_3$=from 1.4 to 2.2.

Very particularly preferred starting reaction gas mixtures 2 comprise
from 7 to 9% by volume of propylene,
from 9.8 to 15% by volume of molecular oxygen,
from 10.5 to 20% by volume of propane and
from 40 to 60% by volume of molecular nitrogen,
where
$V_1$=from 1.5 to 2.5,
$V_2$=from 3.5 to 4.5 and
$V_3$=from 1.4 to 2.14.

The starting reaction gas mixture 2 which is most preferred in accordance with the invention comprises
from 7 to 8% by volume of propylene,
from 11.9 to 15.5% by volume of molecular oxygen,
from 11.9 to 15.5% by volume of propane and
from 50 to 60% by volume of molecular nitrogen
where
$V_1$=from 1.7 to 2.1
$V_2$=from 3.5 to 4.5 and
$V_3$=from 1.7 to 2.1.

In principle, the acrolein content of starting reaction gas mixture 3, from the point of view of satisfactory space-time yields, will be $\geq 3$% by volume.

However, the inventive procedure is especially advantageous when the acrolein content of starting reaction gas mixture 3 is $\geq 4$% by volume, or $\geq 5$% by volume, or $\geq 6$% by volume. Normally, the aforementioned acrolein content will be $\leq 15$% by volume. Preference is given in accordance with the invention to acrolein contents of starting reaction gas mixture 3 of from 6 to 11% by volume, more preferably from 6 to 10% by volume and most preferably from 6 to 9 or from 6 to 8% by volume. Instead of the number 6, 5.5 may also be one of the aforementioned acrolein content limits. The acrolein content of starting reaction gas mixture 3 which is preferred in accordance with the invention is 7% by volume.

It is also generally advantageous for the process according to the invention when the molar ratio $V_4$ of molecular oxygen present in starting reaction gas mixture 3 to acrolein present in starting reaction gas mixture 3 is $\geq 0.5$ and $\leq 2$, advantageously $\geq 1$ and $\leq 1.75$, more advantageously $\geq 1$ and $\leq 1.5$ and most advantageously $\geq 1$ and $\leq 1.25$.

It is additionally advantageous for the process according to the invention when the molar ratio $V_5$ of propane present in starting reaction gas mixture 3 to acrolein present therein is from 1 to 4, preferably from 1.5 to 3.5, more preferably from 1.5 to 3 and most preferably from 1.5 or 2 to 2.5.

Possible inventive starting reaction gas mixtures 3 comprise
from 4.5 to 8% by volume of acrolein,
from 2.25 or 4.5 to 9% by volume of molecular oxygen,
from 6 to 30% by volume of propane,
from 32 to 72% by volume of molecular nitrogen and
from 5 to 15% by volume of steam.

Preferred inventive starting reaction gas mixtures 3 comprise
from 5.5 to 8% by volume of acrolein,
from 2.75 or 5.5 to 9% by volume of molecular oxygen,
from 10 to 25% by volume of propane,
from 40 to 70% by volume of molecular nitrogen and
from 5 to 15% by volume of steam.

Very particularly preferred inventive starting reaction gas mixtures 3 comprise
from 6 to 8% by volume of acrolein,
from 3 or 6 to 9% by volume of molecular oxygen,
from 10 to 20% by volume of propane,
from 50 to 65% by volume of molecular nitrogen and
from 7 to 13% by volume of steam.

According to the invention, it is favorable when a possible starting reaction gas mixture 2 and a possible starting reaction gas mixture 3, or a preferred starting reaction gas mixture 2 and a preferred starting reaction gas mixture 3, or a very particularly preferred starting reaction gas mixture 2 and a very particularly preferred starting reaction gas mixture 3, are employed in combination in the process according to the invention.

In general, both starting reaction gas mixture 2 and starting reaction gas mixture 3 comprise, in addition to the constituents listed in the above frameworks, $\leq 10$% by volume, preferably $\leq 8$% by volume, more preferably $\leq 5$% by volume and most preferably $\leq 3$% by volume of other constituents.

The content, both in starting reaction gas mixture 2 and in starting reaction gas mixture 3, of methane and/or ethane will generally be $\leq 8$% by volume, usually $\leq 5$% by volume and typically $\leq 3$% by volume or $\leq 2$% by volume. Frequently, it will, however, advantageously (both constituents are substantially inert and have favorable heat conductivity) be $\geq 0.5$% by volume.

Particularly advantageously, the total content in starting reaction gas mixture 2 and starting reaction gas mixture 3 of carbon oxides ($CO_2$, CO) in the process according to the invention is $\leq 5$% by volume, particularly advantageously $\leq 3$% by volume or 2% by volume.

In a corresponding manner, the starting reaction gas mixture 2 comprises, in accordance with the invention, with advantage $\leq 5$% by volume of water, advantageously $\leq 3$% by volume of water, more advantageously $\leq 2$% by volume of water and generally $\geq 0.5$% by volume of water.

The hourly space velocity both on the fixed catalyst bed 2 and on the fixed catalyst bed 3 of the particular starting reaction gas is, in accordance with the invention, preferably from 1500 to 4000 or 6000 l (STP)/l·h or more.

The hourly space velocity both on the fixed catalyst bed 2 and on the fixed catalyst bed 3 of the particular reactants (propylene or acrolein) is normally $\geq$70 l (STP)/l·h, advantageously $\geq$90 l (STP)/l·h or $\geq$120 l (STP)/l·h, more advantageously $\geq$140 l (STP)/l·h and most advantageously $\geq$160 l (STP)/l·h. In general, the aforementioned reactant hourly space velocities are $\leq$600 l (STP)/l·h, in many cases $\leq$300 l (STP)/l·h and often $\geq$250 l (STP)/l·h.

Both in the second reaction stage and in the third reaction stage, the reaction pressure is generally in the range from 0.5 to 3 bar, preference being given to the range from 1 to 3 bar.

The temperature of the fixed catalyst bed 2 in the second reaction stage is generally from 300 to 400° C. The temperature of the fixed catalyst bed 3 in the third reaction stage is generally from 200 to 350° C.

When the first reaction stage is an oxydehydrogenation of propane, it may be carried out as a homogeneous and/or heterogeneously catalyzed oxydehydrogenation of propane to propylene with molecular oxygen in the gas phase. The molecular oxygen source used may be air, pure molecular oxygen or molecular oxygen-enriched air. Useful alternative oxygen sources are also nitrogen oxides such as $NO_2$, $N_2O_4$, etc.

When the first reaction stage is configured as a homogeneous oxydehydrogenation, this can in principle be carried out as described, for example, in the documents U.S. Pat. No. 3,798,283, CN-A 1 105 352, Applied Catalysis, 70(2)1991, p. 175-187, Catalysis Today 13, 1992, p. 673-678 and in the application DE-A 19 622 331. An appropriate oxygen source is air. The temperature of the homogeneous oxydehydrogenation is appropriately selected within the range from 300 to 700° C., preferably within the range from 400 to 600° C., more preferably within the range from 400 to 500° C. The working pressure may be from 0.5 to 100 bar, in particular from 1 to 10 bar. The residence time is typically from 0.1 or 0.5 to 20 seconds, preferably from 0.1 or 0.5 to 5 seconds.

The reactor used may, for example, be a tube oven or a tube bundle reactor, for example a countercurrent tube oven with flue gas as a heat carrier or a tube bundle reactor with salt melt as a heat carrier. The propane to oxygen ratio in the corresponding starting reaction gas mixture 1 is preferably from 0.5:1 to 40:1, in particular between 1:1 to 6:1, more preferably between 2:1 to 5:1. Starting reaction gas mixture 1 may also comprise further, preferably inert (in this document, inert constituents refer, as already stated, quite generally preferably to those constituents which are converted in the relevant reaction step to an extent of less than 5 mol %, preferably to an extent of less than 3 mol % and more preferably to an extent of less than 1 mol %; most preferably, they are not converted at all), constituents such as water, carbon dioxide, carbon monoxide, nitrogen, noble gases, other hydrocarbons (for example secondary constituents present in the crude propane) and/or propylene, etc., and it may also include recycled (cycle gas) constituents.

When the propane dehydrogenation is configured as a heterogeneously catalyzed oxydehydrogenation, it can in principle be carried out as described, for example, in the documents U.S. Pat. No. 4,788,371, CN-A 1073893, Catalysis Letters 23 (1994), 103-106, W. Zhang, Gaodeng Xuexiao Huaxue Xuebao, 14 (1993) 566, Z. Huang, Shiyou Huagong, 21 (1992) 592, WO 97/36849, DE-A 197 53 817, U.S. Pat. Nos. 3,862,256, and 3,887,631, DE-A 195 30 454, U.S. Pat. No. 4,341,664, J. of Catalysis 167, 560-569 (1997), J. of Catalysis 167, 550-559 (1997), Topics in Catalysis 3 (1996) 265-275, U.S. Pat. No. 5,086,032, Catalysis Letters 10 (1991), 181-192, Ind. Eng. Chem. Res. 1996, 35, 14-18, U.S. Pat. No. 4,255,284, Applied Catalysis A: General, 100 (1993), 111-130, J. of Catalysis 148, 56-67 (1994), V. Cortés Corberán and S. Vic Bellón (Ed.), New Developments in Selective Oxidation II, 1994, Elsevier Science B. V., p. 305-313, 3rd World Congress on Oxidation Catalysis, R. K. Grasselli, S. T. Oyama, A. M. Gaffney and J. E. Lyons (Ed.), 1997, Elsevier Science B. V., p. 375ff or in DE-A 19837520, DE-A 19837517, DE-A 19837519 and DE-A 19837518. It is also possible to use air as the oxygen source. However, the oxygen source here frequently consists to an extent of at least 90 mol % of molecular oxygen, and in many cases at least 95 mol % of molecular oxygen.

The catalysts suitable for the heterogeneously catalyzed oxydehydrogenation are subject to no particular restrictions. Suitable oxydehydrogenation catalysts are all of those which are known to those skilled in this field of the art and are capable of oxidizing propane to propylene. In particular, it is possible to use all of the oxydehydrogenation catalysts specified in the aforementioned documents. Suitable catalysts are, for example, oxydehydrogenation catalysts which comprise MoVNb oxides or vanadyl pyrophosphate, if appropriate with promoter. One example of a favorable oxydehydrogenation catalyst is a catalyst which comprises a mixed metal oxide having Mo, V, Te, O and X as essential constituents, X being at least one element selected from niobium, tantalum, tungsten, titanium, aluminum, zirconium, chromium, manganese, gallium, iron, ruthenium, cobalt, rhodium, nickel, palladium, platinum, antimony, bismuth, boron, indium, silicon, lanthanum, sodium, lithium, potassium, magnesium, silver, gold and cerium (on this subject, cf. also EP-A 938463 and EP-A 167109). Further particularly suitable oxydehydrogenation catalysts are the multimetal oxide compositions or catalysts A of DE-A-197 53 817 and the catalysts of DE-A 19838312, and the multimetal oxide compositions and catalysts A specified as preferred in the former document are very particularly favorable. In other words, useful active compositions for the oxydehydrogenation are in particular multimetal oxide compositions of the following general formula $$M^1{}_a Mo_{1-b} M^2{}_b O_x$$

where
$M^1$=Co, Ni, Mg, Zn, Mn and/or Cu,
$M^2$=W, V, Te, Nb, P, Cr, Fe, Sb, Ce, Sn and/or La,
a=0.5-1.5
b=0-0.5
and
x=a number which is determined by the valency and frequency of the elements in the general formula other than oxygen.

In principle, suitable active compositions of the aforementioned general formula can be prepared in a simple manner by generating a very intimate, preferably finely divided dry mixture having a composition corresponding to their stoichiometry from suitable sources of their elemental constituents and calcining it at temperatures of from 450 to 1000° C. Useful sources for the elemental constituents of the general formula may be compounds which are already oxides and/or compounds which can be converted to oxides by heating, at least in the presence of oxygen. These are in particular halides, nitrates, formates, oxalates, citrates, acetates, carbonates, ammine complex salts, ammonium salts and/or hydroxides. The starting compounds for preparing the multimetal oxide composition may be intimately mixed in dry form, for example as a finely divided powder, or in wet form, for example with water as a solvent. The resulting multimetal oxide compositions may be used for the oxydehydrogenation either in powder form or shaped to particular catalyst geometries, in which case the shaping may be effected before or after the final calcination. They may also be used in the form of unsupported catalysts. A pulverulent active composition or precursor composition may also be shaped by applying to preshaped inert catalyst supports. The support materials used may be customary, porous or nonporous aluminum oxides, silicon dioxide, thorium dioxide, zirconium dioxide, silicon carbide or silicates, and the support bodies may have a regular or irregular shape.

For the heterogeneously catalyzed oxydehydrogenation of propane, the reaction temperature is preferably in the range from 200 to 600° C., especially in the range from 250 to 500° C., more preferably in the range from 350 to 440° C. The working pressure is preferably in the range from 0.5 to 10 bar, in particular from 1 to 10 bar, more preferably from 1 to 5 bar. Working pressures above 1 bar, for example from 1.5 to 10 bar, have been found to be particularly advantageous. In general, the heterogeneously catalyzed oxydehydrogenation of propane is effected over a fixed catalyst bed. The latter is appropriately introduced as bed into the tubes of a tube bundle reactor, as described, for example, in EP-A-0 700 893 and EP-A-0 700 714 and the literature cited in these documents. The average residence time of reaction gas mixture 1 in the catalyst charge is appropriately from 0.5 to 20 seconds. The ratio of propane to oxygen varies with the desired conversion and the selectivity of the catalyst. It is appropriately in the range from 0.5:1 to 40:1, in particular from 1:1 to 6:1, more preferably from 2:1 to 5:1. In general, the propylene selectivity decreases with rising propane conversion. Preference is therefore given to carrying out the propane to propylene reaction in such a way that relatively low conversions of propane are attained at high selectivities for propylene. The conversion of propane is more preferably in the range from 5 to 40 mol %, frequently in the range from 10 to 30 mol %. In this context, the term "propane conversion" means the proportion of propane fed (sum of propane present in the crude propane and recycled $C_3$ cycle gas) which is converted in single pass. In general, the selectivity of propylene formation is from 50 to 98 mol %, more preferably from 80 to 98 mol %, the term "selectivity" referring to the number of moles of propylene which are obtained per mole of converted propane, expressed as a molar percentage.

In general, the starting mixture used in the oxidative propane dehydrogenation comprises from 5 to 95 mol % of propane (based on 100 mol % of starting mixture). In addition to propane and oxygen, the starting mixture for the heterogeneously catalyzed oxydehydrogenation may also comprise further, especially inert, constituents such as carbon dioxide, carbon monoxide, nitrogen, noble gases, other hydrocarbons, for example secondary constituents present in the crude propane, and/or propylene. The heterogeneously catalyzed oxydehydrogenation may also be carried out in the presence of diluents, for example steam.

Any reactor sequence which is known to those skilled in the art may be used to carry out the homogeneous oxydehydrogenation or the heterogeneously catalyzed oxydehydrogenation of propane. For example, the oxydehydrogenation may be carried out in a single reactor or in a battery of two or more reactors, between which oxygen is introduced if appropriate. The possibility also exists of practising the homogeneous and the heterogeneously catalyzed oxydehydrogenation in combination with one another.

Product gas mixture 1 of an inventive propane oxydehydrogenation may comprise, for example, the following components as possible constituents: propylene, propane, carbon dioxide, carbon monoxide, water, nitrogen, oxygen, ethane, ethene, methane, acrolein, acrylic acid, ethylene oxide, butane (e.g. n-butane or isobutane), acetic acid, formaldehyde, formic acid, propylene oxide and butenes (e.g. butene-1). Typically, a product gas mixture obtained in the inventive propane oxydehydrogenation comprises: from 5 to 10 mol % of propylene, from 0.1 to 2 mol % of carbon monoxide, from 1 to 3 mol % of carbon dioxide, from 4 to 10 mol % of water, from 0 to 1 mol % of nitrogen, from 0.1 to 0.5 mol % of acrolein, from 0 to 1 mol % of acrylic acid, from 0.05 to 0.2 mol % of acetic acid, from 0.01 to 0.05 mol % of formaldehyde, from 1 to 5 mol % of oxygen, from 0.1 to 1.0 mol % of further abovementioned components, and, as the remainder, substantially propane, based in each case on 100 mol % of product gas mixture.

Advantageously in accordance with the invention, the first reaction stage is, however, a conventional heterogeneously catalyzed partial dehydrogenation of propane. In principle, all known heterogeneously catalyzed partial dehydrogenations of propane are useful for this purpose, as known, for example, from the documents WO 03/076370, WO 01/96271, EP-A 117 146, WO 03/011804, U.S. Pat. No. 3,161,670, WO 01/96270, DE-A 33 13 573, DE-A 102 45 585, DE-A 103 16 039 and from the German application DE-A 10 2004 032 129.

All dehydrogenation catalysts known for this purpose in the prior art are likewise useful. Advantageously, dehydrogenation will be effected in a fixed catalyst bed.

The dehydrogenation catalysts can be divided roughly into two groups, into those which are of oxidic nature (for example chromium oxide and/or aluminum oxide) and into those which consist of at least one generally comparatively noble metal (for example platinum) deposited onto a generally oxidic support. Dehydrogenation catalysts which may be used include all of those which are recommended in DE-A 102 19 879, WO 01/96270, EP-A 731 077, DE-A 10211275, DE-A 10131297, WO 99/46039, U.S. Pat. No. 4,788,371, EP-A-0 705 136, WO 99/29420, U.S. Pat. Nos. 4,220,091, 5,430,220, and 5,877,369, EP-A-0 117 146, DE-A 199 37 196, DE-A 199 37 105 and DE-A 199 37 107, and also the catalyst according to example 4 of DE-A 102 19 879. In particular, the catalyst according to example 1, example 2, example 3 and example 4 of DE-A 199 37 107, the catalyst according to example 4 of DE-A 102 19 879 and the catalysts of WO 02/51547, WO 02/51540 and DE-A 10 2005 002 127 may be used.

They are dehydrogenation catalysts which comprise from 10 to 99.9% by weight of zirconium dioxide, from 0 to 60% by weight of aluminum oxide, silicon dioxide and/or titanium dioxide, and from 0.1 to 10% by weight of at least one element of the first or second main group, of an element of the third transition group, of an element of the eighth transition group of the periodic table of the elements, lanthanum and/or tin, with the proviso that the sum of the percentages by weight is 100% by weight.

Also particularly suitable is the dehydrogenation catalyst used in the example of this document.

Generally, the dehydrogenation catalysts are catalyst extrudates (diameter typically from 1 to 10 mm, preferably from 1.5 to 5 mm; length typically from 1 to 20 mm, preferably from 3 to 10 mm), tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm).

In general, the dehydrogenation catalysts (especially those used by way of example in this document and those recommended in DE-A 199 37 107 (especially the exemplary catalysts of this DE-A)) are such that they are capable of catalyzing both the dehydrogenation of propane and the combustion of molecular hydrogen. In the case of a competition situation over the catalysts, the hydrogen combustion proceeds very much more rapidly in comparison to the dehydrogenation of propane.

For the performance of the heterogeneously catalyzed propane dehydrogenation, in principle all reactor types and process variants known in the prior art are useful. Descriptions of such process variants are contained, for example, in all prior art documents cited with regard to the conventional dehydrogenations and accompanying dehydrogenation catalysts.

It is characteristic of the partial heterogeneously catalyzed dehydrogenation of propane that it proceeds endothermically. This means that the heat (energy) required for the attainment of the required reaction temperature and for the reaction has to be supplied to the starting reaction gas mixture 1 either beforehand and/or in the course of the heterogeneously catalyzed dehydrogenation. In some cases, the reaction gas mixture 1 has to draw the heat of reaction required from itself.

In addition, it is typical of heterogeneously catalyzed dehydrogenations of propane, owing to the high reaction temperatures required, that small amounts of high molecular weight organic compounds having a high boiling point, up to and including carbon, are formed and are deposited on the catalyst surface, thus deactivating it. In order to minimize this disadvantageous accompanying phenomenon, the propane-containing reaction gas mixture 1 which is to be passed at elevated temperature over the catalyst surface for the heterogeneously catalyzed dehydrogenation can be diluted with steam. Carbon which is deposited is partly or fully eliminated under the resulting conditions by the principle of coal gasification.

Another means of eliminated deposited carbon compounds is to allow a gas comprising oxygen (appropriately in the absence of hydrocarbons) to flow through the dehydrogenation catalyst at elevated temperature from time to time (if required daily or hourly) and thus to effectively burn off the deposited carbon. However, substantial suppression of the formation of carbon deposits is also possible by adding molecular hydrogen to the propane to be dehydrogenated under heterogeneous catalysis before it is conducted through the dehydrogenation catalyst at elevated temperature. High dehydrogenation conversions generally result in short regeneration intervals.

There is of course also the possibility of adding a mixture of steam and molecular hydrogen to the propane to be dehydrogenated under heterogeneous catalysis. Addition of molecular hydrogen to the heterogeneously catalyzed dehydrogenation of propane also reduces the undesired formation of allene (propadiene), propyne and acetylene as by-products. Partial oxidation of hydrogen added in this way is likewise capable of supplying heat of reaction required.

An essential feature of the invention is that useful reaction stages 1 are also heterogeneously catalyzed partial propane dehydrogenations in which the propane conversion is from 20 to 30 mol % (based on single pass of fresh propane through the dehydrogenation). However, particularly favorable heterogeneously catalyzed partial propane dehydrogenations as reaction stage 1 of the process according to the invention are those in which the aforementioned propane conversion is from 30 to 60 mol %, preferably from 35 to 55 mol % and more preferably from 35 to 45 mol %. Another suitable conversion range is from 25 or 30 to 40 mol %.

For the realization of the aforementioned propane conversions, it is favorable to carry out the heterogeneously catalyzed propane dehydrogenation at a working pressure of from 0.3 to 10 bar, or advantageously to 3 bar. It is also favorable to dilute the propane to be dehydrogenated under heterogeneous catalysis with steam. Thus, the heat capacity of the water firstly balances out a portion of the effect of the endothermicity of the dehydrogenation and the dilution with steam secondly reduces the partial reactant and product pressure, which has a favorable effect on the equilibrium position of the dehydrogenation. In addition, the use of steam, as already mentioned, has an advantageous effect on the onstream time of dehydrogenation catalysts comprising noble metal, especially in the case of desired high propane conversions. If required, molecular hydrogen may also be added as a further constituent. The molar ratio of molecular hydrogen to propane in starting reaction gas mixture 1 is generally $\leq 5$. The molar ratio of steam to propane in starting reaction gas mixture 1 is appropriately from $\geq 0.05$ to 2 or to 1.

Generally, very small amounts of steam in starting reaction gas mixture 1 are preferred and pursued. In the case of propane conversions based on fresh propane in the range from 20 to 30 mol %, the amount of steam typically present in the oxidation cycle gas which is optionally recycled into starting reaction gas mixture 1 in accordance with the invention is typically sufficient as the steam supply for the heterogeneously catalyzed dehydrogenation. For higher propane conversions based on fresh propane, steam is normally added additionally, which may, for example, be separated process water.

In principle, a heterogeneously catalyzed partial propane dehydrogenation functioning as reaction stage 1 may be carried out (quasi)adiabatically and at the same time endothermically. In this case, starting reaction gas mixture 1 is heated generally to a temperature of from 500 to 700° C. (or from 550 to 650° C.) (for example by direct firing of the surrounding wall). In the case of adiabatic pass through the at least one catalyst bed, reaction gas mixture 1 will then cool by from about 30° C. to 200° C. depending on conversion and dilution. Presence of steam as a heat carrier also becomes noticeably advantageous from the point of view of an adiabatic mode. Lower reaction temperatures enable longer onstream times of the catalyst bed used. Higher reaction temperatures support increased conversions.

Appropriately from an application point of view, a heterogeneously catalyzed propane dehydrogenation as reaction stage 1 for the process according to the invention will be realized in the form of a tray reactor.

This appropriately comprises more than one catalyst bed catalyzing the dehydrogenation in spatial succession. The catalyst bed number may be from 1 to 20, appropriately from 2 to 8, or else from 3 to 6. Increased propane conversions can be achieved increasingly readily with increasing number of trays. The catalyst beds are preferably arranged in radial or axial succession. From an application point of view, it is appropriate to use the catalyst bed in the form of a fixed bed in such a tray reactor.

In the simplest case, the fixed catalyst beds in a shaft furnace reactor are arranged axially or in the annular gaps of concentric cylindrical grids. However, it is also possible to arrange the annular gaps in segments one above another and to conduct the gas after it has passed radially through one segment into the next segment above it or below it.

Appropriately, reaction gas mixture 1 is subjected to intermediate heating in the tray reactor on its path from one catalyst bed to the next catalyst bed, for example by passing it over heat exchanger surfaces (e.g. ribs) heated by hot gases or by passing it through pipes heated by hot combustion gases.

When the tray reactor is otherwise operated adiabatically, it is sufficient for propane conversions based of fresh propane of $\leq 30$ mol %, in particular when using the catalysts described in DE-A 199 37 107, especially those of the exemplary embodiments, to conduct reaction gas mixture 1 into the dehydrogenation reactor preheated to a temperature of from 450 to 550° C. and to keep it within this temperature range inside the tray reactor. This means that the entire propane dehydrogenation can thus be realized at very low temperatures, which is found to be particularly favorable for the onstream time of the fixed catalyst beds between two regenerations. For higher propane conversions, reaction gas mixture 1 is appropriately conducted into the dehydrogenation reactor preheated to higher temperatures (these may be up to 700° C.) and kept within this elevated temperature range inside the tray reactor.

It is even more elegant to carry out the above-outlined intermediate heating in a direct way (autothermal method). To this end, a limited amount of molecular oxygen is added to reaction gas mixture 1 either before it flows through the first catalyst bed (in that case starting reaction gas mixture 1 should comprise added molecular hydrogen) and/or between the downstream catalyst beds. It is thus possible (generally catalyzed by the dehydrogenation catalysts themselves) to bring about a limited combustion of molecular hydrogen which is present in reaction gas mixture 1, has been formed in the course of the heterogeneously catalyzed propane dehydrogenation and/or has been added to reaction gas mixture 1 (in some cases accompanied to a minor extent by propane conversion) (it may also be appropriate from an application point of view to insert catalyst beds in the tray reactor which are charged with catalyst which particularly specifically (selectively) catalyzes the combustion of hydrogen (examples of useful catalysts include those of the documents U.S. Pat. Nos. 4,788,371, 4,886,928, 5,430,209, 5,530,171, 5,527,979 and 5,563,314; for example, such catalyst beds may be accommodated in the tray reactor in alternation to the beds comprising dehydrogenation catalyst). The heat of reaction released thus allows virtually isothermal operation of the heterogeneously catalyzed propane dehydrogenation in a quasi-autothermal manner (the gross exothermicity is essentially zero). As the selected residence time of the reaction gas in the catalyst bed is increased, propane dehydrogenation is thus possible at decreasing or substantially constant temperature, which enables particularly long onstream times between two regenerations (in the extreme case, to ensure autothermicity, it is also possible to only combust propane).

In general, oxygen feeding as described above should be undertaken in accordance with the invention in such a way that the oxygen content of reaction gas mixture 1, based on the amount of molecular hydrogen contained therein, is from 0.5 to 50 or to 30% by volume, preferably from 10 to 25% by volume. Useful oxygen sources include both pure molecular oxygen and oxygen diluted with inert gas, for example CO, $CO_2$, $N_2$ and/or noble gases, but especially also air (apart from oxidation cycle gas, preference is given to using exclusively air as the oxygen source). The resulting combustion gases generally have an additional diluting effect and thus promote heterogeneously catalyzed propane dehydrogenation. This is especially true of steam formed in the course of combustion.

The isothermicity of the heterogeneously catalyzed propane dehydrogenation which functions appropriately as reaction stage 1 for the process according to the invention can be further improved by incorporating closed (for example tubular) internals which have favorably, but not necessarily, been evacuated before filling in the spaces between the catalyst beds in the tray reactor. These internals contain suitable solids or liquids which evaporate or melt above a certain temperature, thereby consuming heat, and, when the temperature falls below this value, condense again and thereby release heat.

A heterogeneously catalyzed propane dehydrogenation which forms reaction stage 1 can of course also be realized as described in DE-A 102 11 275 (as a "loop variant"), which forms an integral part of this patent application.

In other words, it is advantageous for the process according to the invention that a process for the continuous heterogeneously catalyzed partial dehydrogenation of propane in the gas phase can function as reaction stage 1, in which a starting reaction gas mixture 1 which comprises the propane which is to be dehydrogenated is fed continuously to a dehydrogenation zone, starting reaction gas mixture 1 is conducted in the dehydrogenation zone through at least one fixed catalyst bed, over which molecular hydrogen and (partially) propylene are formed by catalytic dehydrogenation, at least one gas comprising molecular oxygen is added to starting reaction gas mixture 1 before and/or after entry into the dehydrogenation zone, the molecular oxygen oxidizes the molecular hydrogen present in reaction gas mixture 1 partly to steam in the dehydrogenation zone and a product gas which comprises molecular hydrogen, steam, propylene and unconverted propane is removed from the dehydrogenation zone, and wherein the product gas withdrawn from the dehydrogenation zone is divided into two portions of identical composition and one of the two portions is recycled into the dehydrogenation zone as dehydrogenation cycle gas (preferably as a constituent of starting reaction gas mixture 1), as also recommended by WO 03/076370.

In this case, oxidation cycle gas may be a constituent of starting reaction gas mixture 1 and/or, according to the teaching of the German patent application DE-A 10 2004 032 129, not added to reaction gas mixture 1 until dehydrogenation has proceeded at least partly.

When oxidation cycle gas is a constituent of starting reaction gas mixture 1, it appropriately comprises only the molecular oxygen stemming from the oxidation cycle gas.

For the process according to the invention, it is favorable in the context of the loop mode described when the amount of dehydrogenation cycle gas, based on the product gas formed in the dehydrogenation, is from 30 to 70% by volume, advantageously from 40 to 60% by volume, preferably 50% by volume.

With regard to reaction stages 2 and 3 which follow in accordance with the invention, starting reaction gas mixture 1 comprises, in the case of a loop mode carried out as described, for example, in a tray reactor (tray loop reactor then=dehydrogenation zone), in the steady state appropriately:

| | |
|---|---|
| from 15 to 25% by volume | of propane, |
| from 2 to 6% by volume | of propylene, |
| from 5 to 20% by volume | of steam, |
| from 2 to 10% by volume | of molecular hydrogen, |
| from 40 to 75% by volume | of molecular nitrogen, and |
| from >0 to 3% by volume | of molecular oxygen. |

The conversion of propane (based on single pass of the aforementioned starting reaction gas mixture 1 through the tray reactor operated in loop mode) and the loop cycle gas ratio (amount of dehydrogenation cycle gas based on the total amount of product gas obtained in the dehydrogenation zone) are selected with a view to the two-stage heterogeneously catalyzed gas phase partial oxidation of propylene which follows in accordance with the invention advantageously (for example in a tray loop reactor as the dehydrogenation zone) in such a way that the product gas formed in the dehydrogenation zone comprises unconverted propane and desired propylene in a molar propene to propane ratio of from 0.25 or 0.3 to 0.5 (in some cases to 0.66). At a loop cycle gas ratio of 0.5, this corresponds to a conversion of the propane present in starting reaction gas mixture 1 based on single pass thereof through the dehydrogenation zone of from 15 to 25 mol %.

Typical hourly space velocities on the dehydrogenation catalyst beds of reaction gas mixture 1 are from 250 to 5000 $h^{-1}$ (in high-load mode even up to 40 000 $h^{-1}$), preferably from 10 000 to 25 000 l (STP)/l·h, more preferably from 15 000 to 20 000 l (STP)/l·h. The corresponding hourly space velocities of propane are typically from 50 to 1000 $h^{-1}$ (in high-load mode even up to 40 000 $h^{-1}$), preferably from 2000 to 5000 l (STP)/l·h, more preferably from 3000 to 4000 l (STP)/l·h.

The dehydrogenation product gas withdrawn as a propylene source (reaction stage 1) from the dehydrogenation zone (the dehydrogenation reactor), according to the reaction conditions selected for the heterogeneously catalyzed propane dehydrogenation, is at a pressure of from 0.3 to 10 bar, preferably from 1 to 3 bar, and frequently has a temperature of from 450 to 650° C., in many cases a temperature of from 500 to 600° C. In general, it comprises propane, propene, $H_2$, $N_2$, $H_2O$, methane, ethane (the latter two result usually as a consequence of thermal decomposition of a small amount of propane), ethylene, butene-1, other butenes such as isobutene, other $C_4$-hydrocarbons such as n-butane, isobutane, butadiene, etc., CO and $CO_2$, but generally also oxygenates such as alcohols, aldehydes and carboxylic acids (normally having $\leq 9$ carbon atoms). In addition, constituents arising from the oxidation cycle gas may also be present in small amounts.

While EP-A 117 146, DE-A 33 13 573 and U.S. Pat. No. 3,161,670 recommend the use of the product gas formed in a propane oxydehydrogenation and/or propane dehydrogenation as such to charge the inventive partial oxidation, it is advantageous for the two-stage partial oxidation of propylene to acrylic acid which follows in accordance with the invention to remove at least a portion of the constituents other than propane and propylene present therein from the propylene-containing product gas of the first reaction stage before it is used as the propene source for the inventive propylene partial oxidation. In this context, the requirements of DE-A 102 11 275 should be observed. This removal offers a further discharge means for secondary components other than propane and propylene in the process according to the invention.

Advantageously in accordance with the invention, at least 50% by volume, preferably at least 75% by volume, more preferably at least 90% by volume and most preferably at least 95% by volume, of the constituents other than propane and propylene which are present in the product gas of the first reaction stage will be removed before it is used as the propylene source for the inventive partial oxidation. This is especially true when the first reaction stage is a heterogeneously catalyzed partial propane dehydrogenation.

One means to this end which is appropriate for the inventive requirements consists, for example, in contacting (for example by simply passing it through) the preferably cooled (preferably to temperatures of from 10 to 100 or 70° C.) product gas mixture of the propane dehydrogenation and/or oxydehydrogenation, for example at a pressure of from 0.1 to 50 bar, preferably from 5 to 15 bar and a temperature of, for example, from 0 to 100° C., preferably from 20 to 40° C., with a (preferably high-boiling) organic (preferably hydrophobic) solvent in which propane and propylene are absorbed (appropriately preferentially over the other constituents of the product gas mixtures of the propane dehydrogenation and/or oxydehydrogenation). Subsequent desorption, rectification and/or stripping with a gas which behaves inertly with regard to the inventive partial oxidation and/or is required as a reactant in this partial oxidation (for example air or another mixture of molecular oxygen and inert gas) allows the propane and propylene in a mixture to be recovered in purified form and this mixture to be used as the propylene source for the partial oxidation (preference is given to proceeding as described in comparative example 1 of the German application DE-A 10 2004 032 129). The offgas of such an absorption which may comprise molecular hydrogen can, for example, be subjected again to a pressure swing adsorption and/or membrane separation (for example according to DE-A 10235419) and then, if required, the hydrogen removed can also be used.

However, the C3 hydrocarbons/C4 hydrocarbons separation factor in the aforementioned separation process is comparatively limited and frequently insufficient for the requirements described in DE-A 10245585.

As an alternative to the separation step via absorption described, preference is therefore frequently given to a pressure swing adsorption or a pressure rectification for the inventive purposes.

Suitable absorbents for the above-described absorptive removal are in principle all absorbents which are capable of absorbing propane and propylene (in the manner described below, propane and propylene may also be removed from oxidation cycle gas and then recycled as $C_3$ cycle gas into the first reaction stage (and optionally further reaction stages)). The absorbent is preferably an organic solvent which is preferably hydrophobic and/or high-boiling. Advantageously, this solvent has a boiling point (at a standard pressure of 1 atm) of at least 120° C., preferably of at least 180° C., preferentially of from 200 to 350° C., in particular of from 250 to 300° C., more preferably of from 260 to 290° C. Appropriately, the flashpoint (at a standard pressure of 1 bar) is above 110° C. Generally suitable as absorbents are relatively nonpolar organic solvents, for example aliphatic hydrocarbons which preferably do not contain any externally active polar group, but also aromatic hydrocarbons. Generally, it is desired that the absorbent has a very high boiling point with simultaneously very high solubility for propane and propylene. Examples of absorbents include aliphatic hydrocarbons, for example $C_8$-$C_{20}$-alkanes or alkenes, or aromatic hydrocarbons, for example middle oil fractions from paraffin distillation or ethers having bulky (sterically demanding) groups on the oxygen atom, or mixtures thereof, to which a polar solvent, for example the dimethyl 1,2-phthalate disclosed in DE-A 43 08 087 may be added. Also suitable are esters of benzoic acid and phthalic acid with straight-chain alkanols containing from 1 to 8 carbon atoms, such as n-butyl benzoate, methyl benzoate, ethyl benzoate, dimethyl phthalate, diethyl phthalate, and also what are known as heat carrier oils such as diphenyl, diphenyl ether and mixtures of diphenyl and diphenyl ether or the chlorine derivatives thereof and triarylalkenes, for example 4-methyl-4'-benzyldiphenylmethane and its isomers 2-methyl-2'-benzyl-diphenylmethane, 2-methyl-4'-benzyldiphenylmethane and 4-methyl-2'-benzyldiphenylmethane, and mixtures of such isomers. A suitable absorbent is a solvent mixture of diphenyl and diphenyl ether, preferably in the azeotropic composition, especially of about 25% by weight of diphenyl (biphenyl) and about 75% by weight of diphenyl ether, for example the Diphyl® obtainable commercially (for example purchased from Bayer Aktiengesellschaft). Frequently, this solvent mixture comprises a solvent such as dimethyl phthalate added in an amount of from 0.1 to 25% by weight based on the entire solvent mixture.

Particularly suitable absorbents are also octanes, nonanes, decanes, undecanes, dodecanes, tridecanes, tetradecanes, pentadecanes, hexadecanes, heptadecanes and octadecanes, of which tetradecanes in particular have been found to be particularly suitable. It is favorable when the absorbent used firstly fulfills the abovementioned boiling point but secondly at the same time does not have too high a molecular weight. Advantageously, the molecular weight of the absorbent is $\leqq 300$ g/mol. Also suitable are the paraffin oils having from 8 to 16 carbon atoms described in DE-A 33 13 573. Examples of suitable commercial products are products sold by Haltermann, such as Halpasols i, such as Halpasol 250/340 i and Halpasol 250/275 i, and also printing ink oils under the names PKWF and Printosol. Preference is given to aromatics-free commercial products, for example those of the PKWFaf type. If they comprise a small residual aromatics content, it may advantageously be lowered by rectification and/or adsorption before the use described and suppressed to values significantly below 1000 ppm by weight.

The performance of the absorption is subject to no particular restrictions. It is possible to use all common processes and conditions known to those skilled in the art. Preference is given to contacting the gas mixture with the absorbent at a pressure of from 1 to 50 bar, preferably from 2 to 20 bar, more preferably from 5 to 15 bar, and a temperature of from 0 to 100° C., in particular from 20 to 50 or 40° C. The absorption may be undertaken either in columns or in quench apparatus. It is possible to work in cocurrent or (preferably) in countercurrent. Suitable absorption columns are, for example, tray columns (having bubble-cap and/or sieve trays), columns having structured packings (for example sheet metal packings having a specific surface area of from 100 to 1000, or to 750 m$^2$/m$^3$, for example Mellapak® 250 Y) and columns having random packing (for example filled with Raschig packings). However, it is also possible to use trickle and spray towers, graphite block absorbers, surface absorbers such as thick-film and thin-film absorbers, and also plate scrubbers, cross-spray scrubbers and rotary scrubbers. In addition, it may be favorable to allow the absorption to take place in a bubble column with and without internals.

The propane and the propylene may be removed from the absorbent by stripping, flash evaporation (flashing) and/or distillation.

The propane and propylene are removed from the absorbent preferably by stripping and/or desorption. The desorption may be carried out in a customary manner by a pressure and/or temperature change, preferably at a pressure of from 0.1 to 10 bar, in particular from 1 to 5 bar, more preferably from 1 to 3 bar, and a temperature of from 0 to 200° C., in particular from 20 to 100° C., more preferably from 30 to 70° C., particularly preferably from 30 to 50° C. An example of a gas suitable for the stripping is steam, but preference is given in particular to oxygen/nitrogen mixtures, for example air. When air or oxygen/nitrogen mixtures are used in which the oxygen content is above 10% by volume, it may be sensible, before and/or during the stripping process, to add a gas which reduces the explosion range. Particularly suitable for this purpose are gases having a specific heat capacity of $\geqq 29$ J/mol·K at 20° C., for example methane, ethane, propane (preferred; fresh propane and/or C$_3$ cycle gas are possibilities), propene, benzene, methanol, ethanol, and ammonia, carbon dioxide and water. However, preference is given in accordance with the invention to avoiding C$_4$ hydrocarbons as such additives. Particularly suitable for the stripping are also bubble columns with and without internals.

The propane and propylene may also be removed from the absorbent by a distillation or rectification, in which case the columns which are familiar to those skilled in the art and have structured packings, random packings or appropriate internals can be used. Preferred conditions in the distillation or rectification are a pressure of from 0.01 to 5 bar, in particular from 0.1 to 4 bar, more preferably from 1 to 3 bar, and a temperature (in the bottom) of from 50 to 300° C., in particular from 150 to 250° C.

Before it is used to charge the partial oxidation, a propylene source which has been obtained from the absorbent by stripping and is suitable for the subsequent partial oxidation stages may be fed to a further process stage, in order, for example, to reduce the losses of entrained absorbent (for example separation in demisters and/or depth filters) and to thus simultaneously protect the partial oxidation stages from absorbent or in order to further improve the separating action between C3/C4 hydrocarbons. Such a removal of the absorbent may be effected by all process steps known to those skilled in the art. In the context of the process according to the invention, an example of a preferred embodiment of such a removal is the quenching of the outlet stream from the stripping apparatus with water. In this case, the absorbent is scrubbed out of this laden outlet stream with water and the outlet stream is simultaneously laden with water (small amounts of water have a beneficial effect on the activity of the catalysts for the partial oxidation which follows in accordance with the invention). This scrubbing or the quenching may be effected, for example, at the top of a desorption column using a liquid collecting tray by counterspraying of water or in a dedicated apparatus.

To support the separating effect, it is possible to install internals which increase the quench surface area in the quench chamber, as are known to those skilled in the art from rectifications, absorptions and desorptions.

Water is a preferred scrubbing medium in that it normally does not interfere in the downstream at least one partial zone. After the water has scrubbed the absorbent out of the outlet stream laden with propane and propylene, the water/absorbent mixture may be fed to a phase separation and the treated, low-volume outlet stream fed directly to the partial oxidation which follows in accordance with the invention.

In a manner advantageous for the process according to the invention, it is generally possible, especially when the propylene/propane mixture has been stripped free from the absorbate by means of air, to directly obtain usable starting reaction gas mixtures 2. In the case that their propane content should not yet be satisfactory in accordance with the invention, it is possible also to add fresh propane to them before they are used for the inventive partial oxidation of the propylene present. This is then recycled in accordance with the invention via C$_3$ cycle gas (for example oxidation cycle gas) into reaction stage 1 (for example into the heterogeneously catalyzed dehydrogenation (for example as a constituent of starting reaction gas mixture 1)). Around the appropriate amount of propane, the feed of fresh propane into starting reaction gas mixture 1 (generally into reaction stage 1) may then be reduced. In the extreme case, the required feed of fresh propane in reaction stage 1 (for example in the heterogeneously catalyzed propane dehydrogenation) may be dispensed with fully when this feed of fresh propane is effected, before the inventive partial oxidation of propylene is carried out, fully into starting reaction mixture 2 or 3, whence it is then added to starting reaction gas mixture 1 (or generally to reaction stage 1) for, for example, the heterogeneously catalyzed propane dehydrogenation as a remaining constituent in the oxidation cycle gas only after it has passed through the inventive partial oxidation.

Fresh propane may also be fed partly or fully into starting reaction gas mixture 3 (however, starting reaction gas mixture 3 is sometimes already not explosive when this qualification was actually true for starting reaction gas mixture 2). This is advantageous in particular because an undesired side reaction of propane to propionaldehyde and/or propionic acid starts in particular from the first reaction stage under its conditions. It is also advantageous to divide a fresh propane feed substantially uniformly between the second and the third reaction stage.

As a result of this possibility of feeding fresh propane into starting reaction gas mixture 2 and/or 3, the composition of starting reaction gas mixture 2 and 3 can reliably be made nonexplosive. A decisive factor in answering the question of whether starting reaction gas mixture 2 or 3 is explosive or not is whether combustion (ignition, explosion) initiated by a local ignition source (for example glowing platinum wire) spreads in the starting reaction gas mixture 2 or 3 under certain starting conditions (pressure, temperature) or not (cf. DIN51649 and the investigation description in WO 04/007405). When there is spread, the mixture shall be referred to here as explosive. When there is no spread, the mixture is classified as nonexplosive in this document. When starting reaction gas mixture 2 or 3 is nonexplosive, this also applies to the reaction gas mixtures 2 and 3 formed in the course of the inventive partial oxidation of propylene (cf. WO 04/007405).

It is of course also possible to add the propane (fresh propane) required for the process according to the invention fully to starting reaction gas mixture 1. However, the present invention also relates to advantageous embodiments of the process according to the invention in which the propane (fresh propane) required for the process is added at most partly (for example only to an extent of 75%, or only to an extent of 50%, or only to an extent of 25%) to starting reaction gas mixture 1 and at least partly (generally the remainder, in some cases the entirety) to starting reaction gas mixture 2 (and/or to starting reaction gas mixture 3). Otherwise, the procedure may be as described in WO 01/96170 which forms an integral part of this application.

The two-stage nature of the inventive propylene partial oxidation to acrylic acid is based on the fact that the heterogeneously catalyzed gas phase partial oxidation of propylene to acrylic acid with molecular oxygen proceeds in principle in two successive steps along the reaction coordinate, of which the first leads to acrolein and the second from acrolein to acrylic acid.

The implementation of this fact in two reaction stages opens up the possibility in each of the two oxidation stages of adjusting the fixed catalyst bed to be used and preferably also the other reaction conditions, for example the temperature of the fixed catalyst bed, in an optimizing manner.

Particularly suitable multimetal oxide catalysts for each of the two reaction stages 2 and 3 have been described many times before and are well known to those skilled in the art. For example, EP-A 253 409 on page 5 refers to corresponding U.S. patents.

Favorable catalysts for the particular partial oxidation stage are also disclosed by DE-A 4 431 957, DE-A 102004025445 and DE-A 4431949. This is especially true of those of the general formula I in both of the aforementioned documents. Particularly advantageous catalysts for the particular oxidation stage are disclosed by the documents DE-A 10325488, DE-A 10325487, DE-A 10353954, DE-A 10344149, DE-A 10351269, DE-A 10350812, DE-A 10350822.

For the inventive reaction stage 2, i.e. the heterogeneously catalyzed gas phase partial oxidation of propylene to acrolein, useful active compositions are in principle all multimetal oxide compositions comprising Mo, Bi and Fe.

These are in particular the multimetal oxide active compositions of the general formula I of DE-A 199 55 176, the multimetal oxide active compositions of the general formula I of DE-A 199 48 523, the multimetal oxide active compositions of the general formulae I, II and III of DE-A 101 01 695, the multimetal oxide active compositions of the general formulae I, II and III of DE-A 199 48 248 and the multimetal oxide active compositions of the general formulae I, II and III of DE-A 199 55 168 and also the multimetal oxide active compositions specified in EP-A 70 07 14.

Also suitable for this reaction stage are the multimetal oxide catalysts comprising Mo, Bi and Fe which are disclosed in the documents DE-A 100 46 957, DE-A 100 63 162, DE-C 3 338 380, DE-A 199 02 562, EP-A 15 565, DE-C 2 380 765, EP-A 8 074 65, EP-A 27 93 74, DE-A 330 00 44, EP-A 575897, U.S. Pat. No. 4,438,217, DE-A 19855913, WO 98/24746, DE-A 197 46 210 (those of the general formula II), JP-A 91/294239, EP-A 293 224 and EP-A 700 714. This applies in particular to the exemplary embodiments in these documents, and among these particular preference is given to those of EP-A 15565, EP-A 575897, DE-A 197 46 210 and DE-A 198 55 913. Particular emphasis is given in this context to a catalyst according to example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}O_x \cdot 10\ SiO_2$. Emphasis is also given to the example having the serial number 3 from DE-A 198 55 913 (stoichiometry: $Mo_{12}Co_7Fe_3Bi_{0.6}K_{0.08}Si_{1.6}O_x$) as an unsupported hollow cylinder catalyst of geometry 5 mm×3 mm×2 mm (external diameter×height×internal diameter) and also to the unsupported multimetal oxide II catalyst according to example 1 of DE-A 197 46 210. Mention should also be made of the multimetal oxide catalysts of U.S. Pat. No. 4,438,217. The latter is especially true when these hollow cylinders have a geometry of 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Further possible catalyst geometries in this context are extrudates (for example length 7.7 mm and diameter 7 mm; or length 6.4 mm and diameter 5.7 mm).

A multitude of the multimetal oxide active compositions suitable for the step from propylene to acrolein can be encompassed by the general formula IV $$Mo_{12}Bi_aFe_bX^1_cX^2_dX^3_eX^4_fO_n \quad (IV)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in IV other than oxygen.

They are obtainable in a manner known per se (see, for example, DE-A 4 023 239) and are customarily shaped in substance to give spheres, rings or cylinders or else used in the form of coated catalysts, i.e. preshaped inert support bodies coated with the active composition. They may of course also be used as catalysts in powder form.

In principle, active compositions of the general formula IV can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions IV are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions IV can be intimately mixed in dry or in wet form. When they are mixed in dry form, the starting compounds are appropriately used as finely divided powders and subjected to calcination after mixing and optional compacting. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions of the general formula IV may be used for the inventive "propylene→acrolein" step either in powder form or shaped to certain catalyst geometries, and the shaping may be effected either before or after the final calcination. For example, unsupported catalysts can be prepared from the powder form of the active composition or its uncalcined and/or partially calcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries include solid cylinders or hollow cylinders having an external diameter and a length of from 2 to 10 mm. In the case of the hollow cylinder, a wall thickness of from 1 to 3 mm is advantageous. The unsupported catalyst can of course also have spherical geometry, and the spherical diameter can be from 2 to 10 mm.

A particularly favorable hollow cylinder geometry is 5 mm×3 mm×2 mm (external diameter×length×internal diameter), especially in the case of unsupported catalysts.

The pulverulent active composition or its pulverulent precursor composition which is yet to be calcined and/or partially calcined may of course also be shaped by applying to preshaped inert catalyst supports. The coating of the support bodies to produce the coated catalysts is generally performed in a suitable rotatable vessel, as disclosed, for example, by DE-A 2 909 671, EP-A 293 859 or EP-A 714 700. To coat the support bodies, the powder composition to be applied is appropriately moistened and dried again after application, for example by means of hot air. The coating thickness of the powder composition applied to the support body is appropriately selected within the range from 10 to 1000 μm, preferably within the range from 50 to 500 μm and more preferably within the range from 150 to 250 μm.

Useful support materials are the customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention is based. The support bodies can have a regular or irregular shape, although preference is given to regularly shaped support bodies having distinct surface roughness, for example spheres or hollow cylinders. Suitable support bodies are substantially nonporous, surface-roughened spherical supports made of steatite whose diameter is from 1 to 10 mm or to 8 mm, preferably from 4 to 5 mm. However, suitable support bodies are also cylinders whose length is from 2 to 10 mm and whose external diameter is from 4 to 10 mm. In the case of rings suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Support bodies suitable in accordance with the invention are in particular also rings of geometry 7 mm×3 mm×4 mm (external diameter×length×internal diameter). The fineness of the catalytically active oxide compositions to be applied to the surface of the support body is of course adapted to the desired coating thickness (cf. EP-A 714 700).

Multimetal oxide active compositions to be used for the second reaction stage are also compositions of the general formula V

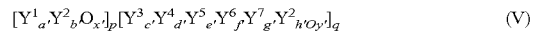

$$[Y^1{}_{a'}Y^2{}_{b'}O_{x'}]_{p'}[Y^3{}_{c'}Y^4{}_{d'}Y^5{}_{e'}Y^6{}_{f'}Y^7{}_{g'}Y^2{}_{h'}O_{y'}]_{q'} \quad (V)$$

in which the variables are each defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from >0 to 20,
f'=from 0 to 6,
g'=from 0 to 15,
h'=from 8 to 16,
x',y'=numbers which are determined by the valency and frequency of the elements in V other than oxygen and p,q=numbers whose p/q ratio is from 0.1 to 10,
comprising three-dimensional regions of the chemical composition $Y^1_a Y^2_b O_{x'}$, which are delimited from their local environment owing to their different composition from their local environment, and whose maximum diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous inventive multimetal oxide compositions V are those in which $Y^1$ is only bismuth.

Among these, preference is given in turn to those of the general formula VI

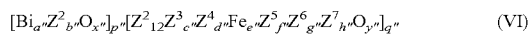

in which the variables are each defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably from 0.1 to 3,
f"=from 0 to 5,
g"=from 0 to 10,
h"=from 0 to 1,
x",y"=numbers which are determined by the valency and frequency of the elements in VI other than oxygen,
p",q"=numbers whose p"/q" ratio is from 0.1 to 5, preferably from 0.5 to 2,
and very particular preference is given to those compositions VI in which $Z^2_{b''}$=(tungsten)$_{b''}$ and $Z^2_{12}$=(molybdenum)$_{12}$.

It is also advantageous when at least 25 mol % (preferably at least 50 mol % and more preferably at least 100 mol %) of the total proportion of $[Y^1_a Y^2_b O_x]_p$ ($[Bi_{a''} Z^2_{b''} O_{x''}]_{p''}$) of the multimetal oxide compositions V (multimetal oxide compositions VI) suitable in accordance with the invention in the multimetal oxide compositions V (multimetal oxide compositions VI) suitable in accordance with the invention is in the form of three-dimensional regions of the chemical composition $Y^1_a Y^2_b O_x [Bi_{a''} Z^2_{b''} O_{x''}]$ which are delimited from their local environment owing to their different chemical composition from their local environment, and whose maximum diameter is in the range from 1 nm to 100 μm.

With regard to the shaping, the statements made for the multimetal oxide composition IV catalysts apply to multimetal oxide composition V catalysts.

The preparation of multimetal oxide active compositions V is described, for example, in EP-A 575 897 and also in DE-A 198 55 913.

The inert support materials recommended above are also useful, inter alia, as inert materials for the dilution and/or delimitation of the appropriate fixed catalyst beds, or as a preliminary bed which protects them and/or heats the gas mixture.

For the third reaction stage, the heterogeneously catalyzed gas phase partial oxidation of acrolein to acrylic acid, useful active compositions are, as already stated, in principle all multimetal oxide compositions comprising Mo and V for the required catalysts, for example those of DE-A 100 46 928.

A multitude thereof, for example those of DE-A 198 15 281, can be encompassed by the general formula VII

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in VII other than oxygen.

Embodiments which are preferred in accordance with the invention among the active multimetal oxides VII are those which are encompassed by the following definitions of the variables of the general formula VII:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 1 to 1 and
n=a number which is determined by the valency and frequency of the elements in VII other than oxygen.

However, multimetal oxides VII which are very particularly preferred in accordance with the invention are those of the general formula VIII

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5,
g'=from 0 to 8 and
n'=a number which is determined by the valency and frequency of the elements in VIII other than oxygen.

The multimetal oxide active compositions (VII) which are suitable in accordance with the invention are obtainable in a manner known per se, for example disclosed in DE-A 43 35 973 or in EP-A 714 700.

In principle, multimetal oxide active compositions suitable for the "acrolein→acrylic acid" step (the third reaction stage), especially those of the general formula VII, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions VII include those compounds which are already oxides and/or those compounds which can be converted to oxides by heating, at least in the presence of oxygen.

The starting compounds for the preparation of multimetal oxide compositions VII can be intimately mixed in dry or in wet form. When they are mixed in dry form, the starting compounds are appropriately used in the form of finely divided powder and subjected to calcining after mixing and, if appropriate, compaction. However, preference is given to intimate mixing in wet form.

This is typically done by mixing the starting compounds with one another in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The resulting multimetal oxide compositions, especially those of the general formula VII, may be used for the acrolein oxidation either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), if appropriate with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinders, a wall thickness of from 1 to 3 mm is appropriate. The unsupported catalyst may of course also have spherical geometry, in which case the spherical diameter may be from 2 to 10 mm (e.g. 8.2 mm or 5.1 mm).

The pulverulent active composition or its pulverulent precursor composition which is yet to be calcined can of course also be shaped by applying to preshaped inert catalyst supports. The coating of the support bodies to prepare the coated catalysts is generally performed in a suitable rotatable vessel, as disclosed, for example, by DE-A 2 909 671, EP-A 293 859 or by EP-A 714 700.

To coat the support bodies, the powder composition to be applied is appropriately moistened and is dried again after application, for example by means of hot air. The coating thickness of the powder composition applied to the support body is appropriately selected within the range from 10 to 1000 µm, preferably within the range from 50 to 500 µm and more preferably within the range from 150 to 250 µm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders with grit layer. Suitable support bodies include substantially nonporous, surface-roughened, spherical supports made of steatite, whose diameter is from 1 to 10 mm or to 8 mm, preferably from 4 to 5 mm. In other words, suitable spherical geometries may have diameters of 8.2 mm or 5.1 mm. However, suitable support bodies also include cylinders whose length is from 2 to 10 mm and whose external diameter is from 4 to 10 mm. In the case of rings as support bodies, the wall thickness is also typically from 1 to 4 mm. Annular support bodies to be used with preference have a length of from 2 to 6 mm, an external diameter of from 4 to 8 mm and a wall thickness of from 1 to 2 mm. Suitable support bodies are also in particular rings of geometry 7 mm×3 mm×4 mm (external diameter×length× internal diameter). The fineness of the catalytically active oxide compositions to be applied to the surface of the support body is of course adapted to the desired coating thickness (cf. EP-A 714 700).

Favorable multimetal oxide active compositions to be used for the "acrolein→acrylic acid" step (the third reaction stage) are also compositions of the general formula IX $$[D]_p[E]_q \quad (IX)$$

in which the variables are each defined as follows:
$E=Z^7{}_{12}Cu_{h''}H_{i''}O_{y''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta, preferably Mo and/or W,
a"=from 1 to 8,
b"=from 0.2 to 5,
c"=from 0 to 23,
d"=from 0 to 50,
e"=from 0 to 2,
f"=from 0 to 5,
g"=from 0 to 50,
h"=from 4 to 30,
i"=from 0 to 20 and
x",y"=numbers which are determined by the valency and frequency of the elements in IX other than oxygen and
p,q=numbers other than zero whose p/q ratio is from 160:1 to 1:1,
and which are obtainable by separately preforming a multimetal oxide composition E

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D

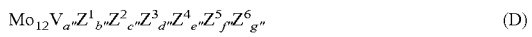

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to the multimetal oxide compositions IX in which the preformed solid starting composition 1 is incorporated into an aqueous starting composition 2 at a temperature of <70° C. A detailed description of the preparation of multimetal oxide composition VI catalysts is contained, for example, in EP-A 668 104, DE-A 197 36 105, DE-A 100 46 928, DE-A 197 40 493 and DE-A 195 28 646.

With regard to the shaping, the statements made for the multimetal oxide composition VII catalysts apply to multimetal oxide composition IX catalysts.

Multimetal oxide catalysts which are outstandingly suitable for the "acrolein→acrylic acid" step are also those of DE-A 198 15 281, especially having multimetal oxide active compositions of the general formula I of this document.

Advantageously, unsupported catalyst rings are used for the step from propylene to acrolein and coated catalyst rings for the step from acrolein to acrylic acid.

The implementation of the second reaction stage, the partial oxidation of propylene to acrolein, may be carried out in a single-zone multiple catalyst tube fixed bed reactor with the catalysts described, for example (quite generally in tube bundle reactors; appropriately from an application point of view, the number of catalyst tubes accommodated in the tube bundle reactor is at least 5000, preferably at least 10 000, frequently from 15 000 to 30 000; a number above 40 000 is usually exceptional; within the vessel, the catalyst tubes are normally arranged in homogeneous distribution, the distribution appropriately being selected in such a way that the separation of the central internal axes of immediately adjacent catalyst tubes (known as the catalyst tube pitch) is from 35 to 45 mm (cf., for example, EP-A 468 290); suitable heat exchange media are in particular fluid heating media; these may be melts of salts such as potassium nitrate, potassium nitrite, sodium nitrite and/or sodium nitrate, or of low-melting metals such as sodium, mercury and alloys of different metals), as described by DE-A 4 431 957. In this case, reaction gas mixture 2 and heat carrier (heat exchange medium) may be conducted in cocurrent or in countercurrent viewed over the reactor.

The reaction pressure is typically in the range from 1 to 3 bar and the total hourly space velocity on the fixed catalyst bed of (starting) reaction gas mixture 2 is preferably from 1500 to 4000 or 6000 l (STP)/l·h or more. The propylene loading (the propylene hourly space velocity on the fixed catalyst bed) is typically from 90 to 200 l (STP)/l·h or to 300 l (STP)/l·h or more. Propylene loadings above 135 l (STP)/l·h or ≧140 l (STP)/l·h, or ≧150 l (STP)/l·h, or ≧160 l (STP)/l·h are particularly preferred in accordance with the invention, since the inventive starting reaction gas mixture 2 and the inventive procedure bring about favorable hotspot behavior (all of the above also applies irrespective of the specific selection of the fixed bed reactor).

The flow to the single-zone multiple catalyst tube fixed bed reactor of the charge gas mixture is preferably from above. The heat exchange medium used is appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$).

Viewed over the reactor, as already stated, salt melt and reaction gas mixture 2 may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows (for the flow from bottom to top, the charge sequence is appropriately reversed):

first, to a length of from 40 to 80 or to 60% of the catalyst tube length, either only catalyst or a mixture of catalyst and inert material, the latter, based on the mixture, making up a proportion by weight of up to 20% by weight (section C);

following this, to a length of from 20 to 50 or to 40% of the total tube length, either only catalyst or a mixture of catalyst and inert material, the latter, based on the mixture, making up a proportion by weight of up to 40% by weight (section B); and finally, to a length of from 10 to 20% of the total tube length, a bed of inert material (section A) which is preferably selected such that it causes a very small pressure drop.

Section C is preferably undiluted.

The aforementioned charge variant is especially appropriate when the catalysts used are those according to example 1 of DE-A 100 46 957 or according to example 3 of DE-A 100 46 957 and the inert material used is steatite rings having the geometry 7 mm×7 mm×4 mm (external diameter×height× internal diameter). With regard to the salt bath temperature, the statements of DE-A 4 431 957 apply.

However, the implementation of the second reaction stage, the inventive partial oxidation from propylene to acrolein (and in some cases acrylic acid), may also be carried out with the catalysts described, for example, in a two-zone multiple catalyst tube fixed bed reactor as described by DE-A 199 10 506. Advantageously in accordance with the invention, the inventive partial oxidation of propene to acrolein is effected as described in EP-A 1159244 and most preferably as described in WO 04/085363 and in WO 04/085362, but observing the inventive boundary conditions for $C^P$.

The documents EP-A 1159244, WO 04/085363 and WO 04/085362 are regarded as being an integral part of this document.

In other words, the second reaction stage, the partial oxidation of propylene to acrolein, can be carried out particularly advantageously over a fixed catalyst bed having increased propylene hourly space velocity and at least two temperature zones.

In other words, an advantageous embodiment of the second reaction stage is a process in which starting reaction gas mixture 2 is conducted over (through) a fixed catalyst bed 2 whose active composition is at least one multimetal oxide comprising the elements Mo, Fe and Bi, with the proviso that the propylene conversion on single pass does not exceed the value of $C^P$ predefined in accordance with the invention (the selectivity of acrolein formation and of acrylic acid by-product formation taken together will regularly be ≧90 mol %) and wherein a) the hourly space velocity on fixed catalyst bed 2 of propene present in starting reaction gas mixture 2 is ≧140 or ≧160 l (STP) of propene/l of fixed catalyst bed 2·h, b) fixed catalyst bed 2 consists of one fixed catalyst bed 2 arranged in two spatially successive reaction zones A*, B*, the temperature of reaction zone A* being from 300 to 390° C. and the temperature of reaction zone B* being from 305 to 420° C. and at the same time at least 5° C. above the temperature of reaction zone A*, c) starting reaction gas mixture 2 flows through reaction zones A*, B* in the time sequence "first A*", "then B*" and d) reaction zone A* extends up to a conversion of propene of from 40 to 80% of the value of $C^P$ pursued in accordance with the invention in the second reaction stage.

Otherwise, reference is made to EP-A 1159244.

In other words, a particularly preferred embodiment of the inventive second reaction stage is also a process in which starting reaction gas mixture 2 is conducted over a fixed catalyst bed 2 whose active composition is at least one multimetal oxide comprising the elements Mo, Fe and Bi, with the proviso that fixed catalyst bed 2 is arranged in two spatially successive temperature zones A, B, both the temperature of temperature zone A and the temperature of temperature zone B are a temperature in the range from 290 to 380° C., fixed catalyst bed 2 consists of at least two spatially successive fixed catalyst bed zones, the volume-specific activity within a fixed catalyst bed zone being substantially constant and increasing in flow direction of reaction gas mixture 2 at the transition from one fixed catalyst bed zone into another fixed catalyst bed zone, and said increase preferably being sharp (step increase), temperature zone A extends up to a conversion of propylene of from 40 to 80% of the value of $C^P$ pursued in accordance with the invention in the second reaction stage, the propene conversion in single pass of starting reaction gas mixture 2 through the entire fixed catalyst bed has the value $C^P$ and the selectivity of acrolein formation based on converted propene is ≧90 mol %, the time sequence in which reaction gas mixture 2 flows through temperature zones A, B corresponds to the alphabetic sequence of the temperature zones, the hourly space velocity on fixed catalyst bed 2 of propylene present in starting reaction gas mixture 2 is ≧90 l (STP) of propylene/l of fixed catalyst bed 2·h, and the difference $T^{maxA}-T^{maxB}$, formed from the highest temperature $T^{maxA}$ that reaction gas mixture 2 has within temperature zone A and the highest temperature $T^{maxB}$ that reaction gas mixture 2 has within temperature zone B is ≧0° C., and, optionally more preferred, in the process, the transition from temperature zone A into temperature zone B in fixed catalyst bed 2 does not coincide with a transition from one fixed catalyst bed zone into another fixed catalyst bed zone.

Further details of this procedure can be found in WO 04/085362 which is an integral part of this document, and also in the further course of this document in the description of the particularly preferred simultaneous configuration of the second and third reaction stage of the process according to the invention.

The performance of the third reaction stage, i.e. the partial oxidation of acrolein to acrylic acid, may be carried out with the catalysts described (quite generally in tube bundle reactors; appropriately from an application point of view, the number of catalyst tubes accommodated in the tube bundle reactor is at least 5000, preferably at least 10 000, frequently from 15 000 to 30 000; a number above 40 000 is usually exceptional; within the vessel, the catalyst tubes are normally arranged in homogeneous distribution, the distribution appropriately being selected in such a way that the distance of the central internal axes of immediately adjacent catalyst tubes (known as the catalyst tube pitch) is from 35 to 45 mm (cf., for example, EP-A 468 290); suitable heat exchange media are in particular fluid heating media; these may be melts of salts such as potassium nitrate, potassium nitrite, sodium nitrite and/or sodium nitrate, or of low-melting metals such as sodium, mercury and alloys of different metals; appropriately, both the second and the third reaction stage are operated in such tube bundle reactors), for example in a one-zone multiple catalyst tube fixed bed reactor as described in DE-A 44 31 949. In this reaction stage, reaction gas mixture 3 and heat carrier can be conducted in cocurrent viewed over the reactor. According to the invention, the product gas mixture 2 of the preceding inventive propylene partial oxidation to acrolein may in principle be conducted as such (if appropriate after intermediate cooling (this may be effected indirectly or directly by, for example, secondary air addition) thereof), i.e. without secondary component removal, into the third reaction stage, i.e. into the acrolein partial oxidation.

The molecular oxygen required for the third step, the acrolein partial oxidation, may already be present in the starting reaction gas mixture 2 for the inventive reaction stage too (the propylene partial oxidation to acrolein) (this is preferred in accordance with the invention). However, it may also be added partly or fully directly to the product gas mixture 2 of the first reaction stage (this is preferably effected in the form of (secondary) air, but may also be effected in the form of pure oxygen or of mixtures of inert gas or oxygen).

As in the second reaction stage, the reaction pressure in the third reaction stage too is typically in the range from 1 to 3 bar and the total hourly space velocity on fixed catalyst bed 3 of (starting) reaction gas mixture 3 is preferably from 1500 to 4000 or 6000 l (STP)/l·h or more. The acrolein loading (the acrolein hourly space velocity on fixed catalyst bed 3) is typically from 90 to 190 l (STP)/l·h, or to 290 l (STP)/l·h or more. Acrolein loadings above 135 l (STP)/l·h, or ≧140 l (STP)/l·h, or ≧150 l (STP)/l·h, or ≧160 l (STP)/l·h are particularly preferred, since the inventive presence of propane in starting reaction gas mixture 3 likewise results in favorable hotspot behavior.

The flow to the single-zone multiple catalyst tube fixed bed reactor of charge gas mixture 3 is likewise preferably from above. The heat exchange medium used in the second stage is also appropriately a salt melt, preferably consisting of 60% by weight of potassium nitrate ($KNO_3$) and 40% by weight of sodium nitrite ($NaNO_2$), or of 53% by weight of potassium nitrate ($KNO_3$), 40% by weight of sodium nitrite ($NaNO_2$) and 7% by weight of sodium nitrate ($NaNO_3$). Viewed over the reactor, as already stated, salt melt and reaction gas mixture 3 may be conducted either in cocurrent or in countercurrent. The salt melt itself is preferably conducted in a meandering manner around the catalyst tubes.

When the flow to the catalyst tubes is from top to bottom, it is appropriate to charge the catalyst tubes with catalyst from bottom to top as follows:

first, to a length of from 50 to 80 or to 70% of the catalyst tube length, either only catalyst or a mixture of catalyst and inert material, the latter, based on the mixture, making up a proportion by weight of up to 20% by weight (section C);

following this, to a length of from 20 to 40% of the total tube length, either only catalyst or a mixture of catalyst and inert material, the latter, based on the mixture, making up a proportion by weight of up to 50 or up to 40% by weight (section B); and finally, to a length of from 5 to 20% of the total tube length, a bed of inert material (section A) which is preferably selected such that it causes a very small pressure drop.

Section C is preferably undiluted. As is quite generally the case for the heterogeneously catalyzed gas phase partial oxidation of acrolein to acrylic acid (especially at high acrolein loadings on fixed catalyst bed 3 and high steam contents of charge gas mixture 3), section B may also consist of two successive catalyst dilutions (for the purpose of minimizing hotspot temperature and hotspot temperature sensitivity). From bottom to top, first with up to 20% by weight of inert material and subsequently with from >20% by weight to 50 or 40% by weight of inert material. Section C is then preferably undiluted.

For flow to the catalyst tubes from bottom to top, the catalyst tube charge is appropriately reversed.

The aforementioned charge variant is especially appropriate when the catalysts used are those according to Preparation Example 5 of DE-A 100 46 928 or those according to DE-A 198 15 281 and the inert material used is steatite rings having the geometry 7 mm×7 mm×4 mm or 7 mm×7 mm×3 mm (in each case external diameter×height×internal diameter). With regard to the salt bath temperature, the statements of DE-A 443 19 49 apply. It is generally selected in such a way that the acrolein conversion $C^A$ pursued in accordance with the invention is achieved in single pass.

However, the performance of the partial oxidation of acrolein to acrylic acid may also be carried out with the catalysts described, for example, in a two-zone multiple catalyst tube fixed bed reactor as described in DE-1 99 10 508. For the acrolein conversion, the above statements apply. In this case too, the charge gas mixture (starting reaction gas mixtures 3) will be obtained directly by using product gas mixture 2 (if appropriate after indirect or direct (for example by supplying secondary air) intermediate cooling thereof) (as has already been described above). The oxygen required for the acrolein partial oxidation is preferably added in the form of air (if appropriate also in the form of pure molecular oxygen or in the form of a mixture of molecular oxygen and an inert gas) and, for example, added directly to the product gas mixture 2 of the first step of the two-stage partial oxidation (propylene→acrolein). However, it may also, as already described, already be present in the starting reaction gas mixture 2 for the second reaction stage, which is advantageous in accordance with the invention.

In a two-stage partial oxidation, as described, of propylene to acrylic acid with direct further use of the product gas mixture of the first step of the partial oxidation to charge the second step of the partial oxidation, two one-zone multiple catalyst tube fixed bed reactors (at high reactant hourly space velocity on the catalyst bed, as is quite generally the case, preference is given to countercurrent mode between reaction gas and salt bath (heat carrier) viewed over the tube bundle reactor) or two two-zone multiple catalyst tube fixed bed reactors will generally be connected in series. A mixed series connection (one-zone/two-zone or vice versa) is also possible. "One-zone" in the propene→acrolein stage and "two-zone" in the acrolein→acrylic acid stage is favorable.

Between the reactors may be disposed an intermediate cooler which may if appropriate comprise inert beds which can perform a filter function. The salt bath temperatures of multiple catalyst tube reactors for the first step of the two-stage partial oxidation of propylene to acrylic acid is generally from 300 to 400° C. The salt bath temperature of multiple catalyst tube reactors for the second step of the partial oxidation of propylene to acrylic acid, the partial oxidation of acrolein to acrylic acid, is usually from 200 to 350° C. In addition, the heat exchange media (preferably salt melts) are normally conducted through the relevant multiple catalyst tube fixed bed reactors in such amounts that the difference between their input and their output temperature is generally $\leq 5°$ C.

It should also be mentioned once again that a portion of the starting reaction gas mixture 2 for the first step ("propylene→acrolein") may be oxidation cycle gas (residual gas) coming from the partial oxidation.

This is, as already stated, a gas which comprises molecular oxygen and remains after the target product removal (acrolein and/or acrylic acid removal) from the product gas mixture of the partial oxidation and may be recycled partly as inert diluent gas into the charge for the first and/or if appropriate second step of the partial oxidation of propylene to acrolein and/or acrylic acid.

However, preference is given in accordance with the invention to recycling such oxidation cycle gas comprising propane, molecular oxygen and unconverted propylene exclusively into the first reaction stage which functions as the propylene source (for example the heterogeneously catalyzed propane dehydrogenation).

Overall, a tube bundle reactor within which the catalyst charge changes appropriately along the individual catalyst tubes with completion of the first reaction step (such two-stage propylene partial oxidations in a single reactor are taught, for example, by EP-A 91 13 13, EP-A 97 98 13, EP-A 99 06 36 and DE-A 28 30 765) forms the simplest implementation form of the two oxidation stages for the two steps of the partial oxidation from propylene to acrylic acid. If appropriate, the charge of the catalyst tubes with catalyst is interrupted by an inert bed.

However, preference is given to implementing the two oxidation stages in the form of two tube bundle systems connected in series. These may be disposed in one reactor, in which case the transition from one tube bundle to the other tube bundle is formed by a bed of inert material which is not accommodated in the catalyst tube (and is preferably accessible on foot). While the catalyst tubes are generally flowed around by a heat carrier, this does not reach an inert bed accommodated as described above. Advantageously, the two catalyst tube bundles are therefore accommodated in spatially separate reactors. In general, an intermediate cooler is disposed between the two tube bundle reactors in order to reduce any acrolein postcombustion proceeding in the product gas mixture 2 which leaves the second reaction stage.

The reaction temperature in the second reaction stage (propylene→acrolein) is generally from 300 to 450° C., preferably from 320 to 390° C. The reaction temperature in the third reaction stage (acrolein→acrylic acid) is generally from 200 to 370° C., frequently from 220 to 330° C. The reaction pressure in both oxidation stages is appropriately from 0.5 to 5 bar, advantageously from 1 to 3 bar. The hourly space velocity (l(STP)/l·h) on the oxidation catalysts of reaction gas in both reaction stages is frequently from 1500 to 2500 l (STP)/l·h or to 4000 l (STP)/l·h. The hourly space velocity of propylene in reaction stage 2 may be from 100 to 200 or 300 and more l (STP)/l·h.

In principle, the two oxidation stages in the process according to the invention may be configured as described, for example, in DE-A 198 37 517, DE-A 199 10 506, DE-A 199 10 508 and DE-A 198 37 519.

In both reaction stages, an excess of molecular oxygen relative to the amount required in accordance with the reaction stoichiometry generally has an advantageous effect on the kinetics of the particular gas phase partial oxidation.

Of course, it is possible in one embodiment of an inventive two-stage partial oxidation of propylene to acrylic acid in the form of two oxidation stages connected in series to partly or fully remove carbon dioxide and steam which have formed as a by-product in the first oxidation stage and are present in the product gas mixture leaving the first oxidation stage from this product gas mixture, if required, before it is passed on into the second oxidation stage. Preference is given in accordance with the invention to selecting a procedure which does not provide for such a removal.

Useful sources for intermediate oxygen feeding carried out between the two oxidation stages are, as already stated, in addition to air (preferred), either pure molecular oxygen or molecular oxygen diluted with inert gas such as $CO_2$, CO, noble gases, $N_2$ and/or saturated hydrocarbons. However, it is also possible to add nitrogen oxides as an oxygen source at this point.

In the process according to the invention, metering of, for example, cold air to hot product gas mixture 2 can also bring about cooling thereof by a direct route before it is used further as a constituent of a starting reaction gas mixture 3.

Advantageously in accordance with the invention, the partial oxidation of acrolein to acrylic acid is effected as described in EP-A 11 59 246 and most preferably as described in WO 04/085365 and in WO 04/085370. Preference is given in accordance with the invention to using, as acrolein-containing starting reaction gas mixture 3, the product gas mixture of an inventive partial oxidation of propylene to acrolein which has if appropriate been supplemented with sufficient secondary air that the ratio of molecular oxygen to acrolein in the resulting starting reaction gas mixture 3 is in each case from 0.5 to 1.5. The documents EP-A 1159246, WO 04/08536 and WO 04/085370 are regarded as an integral part of this document.

In other words, the inventive partial oxidation of acrolein to acrylic acid can be carried out with increased acrolein hourly space velocity advantageously over a fixed catalyst bed 3 which has at least two temperature zones.

In other words, an advantageous embodiment of the inventive partial oxidation of acrolein to acrylic acid (reaction stage 3) is a process in which starting reaction gas mixture 3 is conducted over (through) a fixed catalyst bed 3 whose active composition is at least one multimetal oxide comprising the elements Mo and V, with the proviso that the acrolein conversion in single pass reaches the pursued value of $C^A$ (the accompanying selectivity of acrylic acid formation will regularly be $\geq 90$ mol %) and wherein
a) the hourly space velocity on fixed catalyst bed 3 of acrolein present in starting reaction gas mixture 3 is $\geq 130$ or $\geq 150$ l (STP) of acrolein/l of fixed catalyst bed 3·h,
b) fixed catalyst bed 3 consists of one fixed catalyst bed 3 arranged in two spatially successive reaction zones C*, D*, the temperature of reaction zone C* being from 230 to 270° C. and the temperature of reaction zone D* being from 250 to 300° C. and at the same time at least 5° C. above the temperature of reaction zone C*,
c) starting reaction gas mixture 3 flows through reaction zones C*, D* in the time sequence "first C*", "then D*" and
d) reaction zone C* extends up to a conversion of acrolein of from 55 to 85 mol % of the value of $C^A$ pursued in accordance with the invention in the third reaction stage.

Otherwise, reference is made to EP-A 11 59 246.

In other words, a particularly preferred embodiment of the inventive partial oxidation of acrolein to acrylic acid is also a process in which starting reaction gas mixture 3 is conducted over a fixed catalyst bed 3 whose active composition is at least one multimetal oxide comprising the elements Mo and V, with the proviso that fixed catalyst bed 3 is arranged in two spatially successive temperature zones C, D,
both the temperature of temperature zone C and the temperature of temperature zone D are a temperature in the range from 230 to 320° C.,
fixed catalyst bed 3 consists of at least two spatially successive fixed catalyst bed zones, the volume-specific activity within a fixed catalyst bed zone being substantially constant and increasing in flow direction of reaction gas mixture 3 at the transition from one fixed catalyst bed zone into another fixed catalyst bed zone, and said increase preferably being sharp (step increase), temperature zone C extends up to a conversion of acrolein of from 45 to 85% of the value of $C^A$ pursued in accordance with the invention in the third reaction stage,
the acrolein conversion in single pass of starting reaction gas mixture 3 through the entire fixed catalyst bed 2 has the value $C^A$ and the selectivity of acrylic acid formation based on converted acrolein is $\geq 90$ mol %,
the time sequence in which reaction gas mixture 3 flows through temperature zones C, D corresponds to the alphabetic sequence of the temperature zones,
the hourly space velocity on fixed catalyst bed 3 of acrolein present in starting reaction gas mixture 3 is $\geq 70$ l (STP) of acrolein/l of fixed catalyst bed 3·h, and
the difference $T^{maxC}-T^{maxD}$, formed from the highest temperature $T^{maxC}$ that reaction gas mixture 3 has within temperature zone C and the highest temperature $T^{maxD}$ that reaction gas mixture 3 has within temperature zone D is $\geq 0°$ C., and, optionally more preferred, in the process, the transition from temperature zone C into temperature zone D in fixed catalyst bed 3 does not coincide with a transition from one fixed catalyst bed zone into another fixed catalyst bed zone.

Further details of this procedure can be found in WO 04/085370 which is an integral part of this document, and also in the further course of this document in the description of the particularly preferred two-stage partial oxidation of propylene to acrylic acid.

Such a particularly preferred two-stage partial oxidation of propylene to acrylic acid may advantageously be carried out as described in EP-A 1159248 and in WO 04/085367. Both documents form an integral part of this document.

In other words, a starting reaction gas mixture 2 will initially be conducted in the second reaction stage over (through) a fixed catalyst bed 2 whose active composition is at least one multimetal oxide comprising the elements Mo, Fe and Bi, with the proviso that the propylene conversion in single pass attains the value of $C^P$ pursued in accordance with the invention and the accompanying selectivity of acrolein formation and of acrylic acid by-product formation taken together is $\geq 90$ mol %, the temperature of the product gas mixture 2 leaving the second reaction stage will if appropriate be reduced by indirect and/or direct cooling and molecular oxygen and/or inert gas will be added if appropriate to product gas mixture 2, and will then, as a starting reaction gas mixture 3 which comprises acrolein, molecular oxygen and at least one inert gas and comprises the molecular oxygen and the acrolein in a molar $O_2:C_3H_4O$ ratio of $\geq 0.5$, in a third reaction stage over (through) a fixed catalyst bed 3 whose active composition is at least one multimetal oxide comprising molybdenum and vanadium, with the proviso that the acrolein conversion in single pass attains the value of $C^A$ pursued in accordance with the invention and the selectivity of acrylic acid formation assessed over both reaction stages, based on propylene converted, will be $\geq 80$ mol % and the further procedure will be such that
a) the hourly space velocity on fixed catalyst bed 2 of propene present in starting reaction gas mixture 2 is $\geq 140$ or $\geq 160$ l (STP) of propene/l of fixed catalyst bed 2·h,
b) fixed catalyst bed 2 consists of one fixed catalyst bed 2 arranged in two spatially successive reaction zones A*, B*, the temperature of reaction zone A* being from 300 to 390° C. and the temperature of reaction zone B* being from 305 to 420° C. and at the same time at least 5° C. above the temperature of reaction zone A*,
c) starting reaction gas mixture 2 flows through reaction zones A*, B* in the time sequence "first A*", "then B*", d) reaction zone A* extends up to a conversion of propene of from 40 to 80% of the value of $C^P$ pursued in accordance with the invention in the first reaction stage,
e) the hourly space velocity on fixed catalyst bed 3 of acrolein present in starting reaction gas mixture 3 is $\geq 120$ or $\geq 140$ l (STP) of acrolein/l of fixed catalyst bed 3·h,
f) fixed catalyst bed 3 consists of one fixed catalyst bed 3 arranged in two spatially successive reaction zones C*, D*, the temperature of reaction zone C* being from 230 to 270° C. and the temperature of reaction zone D* being from 250 to 300° C. and at the same time at least 10° C. above the reaction zone C*,
g) starting reaction gas mixture 3 flows through reaction zones C*, D* in the time sequence "first C*", "then D*" and
h) reaction zone C* extends up to a conversion of propene of from 55 to 85% of the value of $C^A$ pursued in accordance with the invention in the first reaction stage.

Otherwise, reference is made to EP-A 11 59 248.

However, it will more preferably be carried out according to WO 04/085369 which is an integral part of this document.

In other words, an inventive starting reaction gas mixture 2 will first be conducted in a second reaction stage over a fixed catalyst bed 2 whose active composition is at least one multimetal oxide comprising the elements Mo, Fe and Bi, with the proviso that
  fixed catalyst bed 2 is arranged in two spatially successive temperature zones A, B,
  both the temperature of temperature zone A and the temperature of temperature zone B are a temperature in the range from 290 to 380° C.,
  fixed catalyst bed 2 consists of at least two spatially successive fixed catalyst bed zones, the volume-specific activity within a fixed catalyst bed zone being substantially constant and increasing in flow direction of reaction gas mixture 2 at the transition from one fixed catalyst bed zone into another fixed catalyst bed zone, and said increase preferably being sharp (step increase),
  temperature zone A extends up to a conversion of propene of from 40 to 80 mol % of the value of $C^P$ pursued in accordance with the invention in the second reaction stage,
  the propene conversion in single pass of starting reaction gas mixture 2 through the entire fixed catalyst bed 2 has the value of $C^P$ pursued in accordance with the invention and the selectivity of acrolein formation and of acrylic acid by-product formation taken together and based on converted propene is $\geq 90$ mol %,
  the time sequence in which reaction gas mixture 2 flows through temperature zones A, B corresponds to the alphabetic sequence of temperature zones A, B,
  the hourly space velocity on fixed catalyst bed 2 of propene present in starting reaction gas mixture 2 is $\geq 90$ l (STP) of propene/l of fixed catalyst bed 2·h, and
  the difference $T^{maxA}-T^{maxB}$, formed from the highest temperature $T^{maxA}$ that reaction gas mixture 2 has within temperature zone A and the highest temperature $T^{maxB}$ that reaction gas mixture 2 has within temperature zone B is $\geq 0°$ C.,
then the temperature of product gas mixture 2 leaving the second reaction stage will be reduced if appropriate by cooling and molecular oxygen and/or inert gas if appropriate, preferably air if appropriate, will be added to product gas mixture 2, and it will subsequently be conducted, as a starting reaction gas mixture 3 which comprises acrolein, molecular oxygen and at least one inert gas and comprises the molecular oxygen and the acrolein in a molar $O_2:C_3H_4O$ ratio of $\geq 0.5$, in a third reaction stage over a fixed catalyst bed 3 whose active composition is at least one multimetal oxide comprising the elements Mo and V, with the proviso that
  fixed catalyst bed 3 is arranged in two spatially successive temperature zones C, D,
  both the temperature of temperature zone C and the temperature of temperature zone D are a temperature in the range from 230 to 320° C.,
  fixed catalyst bed 3 consists of at least two spatially successive fixed catalyst bed zones, the volume-specific activity within a fixed catalyst bed zone being substantially constant and increasing in flow direction of reaction gas mixture 3 at the transition from one fixed catalyst bed zone into another fixed catalyst bed zone, and said increase preferably being sharp (step increase),
  temperature zone C extends up to a conversion of acrolein of from 45 to 85% of the value of $C^A$ pursued in the third reaction stage,
  the acrolein conversion in single pass of starting reaction gas mixture 3 through the entire fixed catalyst bed 3 has the value $C^A$ pursued in accordance with the invention and the selectivity of acrylic acid formation based on propene converted over both reaction stages is $\geq 80$ mol %,
  the time sequence in which reaction gas mixture 3 flows through temperature zones C, D corresponds to the alphabetic sequence of the temperature zones C,D,
  the hourly space velocity on fixed catalyst bed 3 of acrolein present in starting reaction gas mixture 3 is $\geq 70$ l (STP) of acrolein/l of fixed catalyst bed 3·h, and
  the difference $T^{maxC}-T^{maxD}$, formed from the highest temperature $T^{maxC}$ that reaction gas mixture 3 has within temperature zone C and the highest temperature $T^{maxD}$ that reaction gas mixture 3 has within temperature zone D is $\geq 0°$ C.,
and, optionally more preferred, in the process, neither the transition from temperature zone A into temperature zone B in fixed catalyst bed 2 nor the transition from temperature zone C into temperature zone D in fixed catalyst bed 3 coincides with a transition from one fixed catalyst bed zone into another fixed catalyst bed zone.

In this document, the temperature of a temperature zone refers to the temperature of the portion of the fixed catalyst bed disposed in the temperature zone when the process according to the invention is being performed, but in the absence of a chemical reaction. When this temperature is not constant within the temperature zone, the term temperature of a temperature zone refers to the (numerical) mean of the temperature of the fixed catalyst bed along the reaction zone. It is essential in this context that the individual temperature zones are heated substantially independent of one another.

Since both the heterogeneously catalyzed partial gas phase oxidation of propene to acrolein and the heterogeneously catalyzed partial gas phase oxidation of acrolein to acrylic acid are markedly exothermic reactions, both the temperature of reaction gas mixture 2 and the temperature of reaction gas mixture 3 on reactive pass through fixed catalyst bed 2 or fixed catalyst bed 3 are generally different from the temperature of a temperature zone. They are normally above the temperature of the temperature zone and generally pass through a maximum (hotspot maximum) or fall starting from a maximum value within a temperature zone.

In general, the difference $T^{maxA}-T^{maxB}$ in the process according to the invention will not be more than 80° C. According to the invention, $T^{maxA}-T^{maxB}$ is preferably $\geq 3°$ C. and $\leq 70°$ C. With very particular preference, $T^{maxA}-T^{maxB}$ in the process according to the invention is $\geq 20°$ C. and $\leq 60°$ C.

When the process according to the invention is being performed in the case of relatively low ($\geq 90$ l (STP)/l·h and $\leq 160$ l (STP)/l·h) propene hourly space velocities on the fixed catalyst bed, the $T^{maxA}$-$T^{maxB}$ differences required according to the invention are normally attained when, firstly, both the temperature of reaction zone A and the temperature of reaction zone B are in the range from 290 to 380° C. and, secondly, the difference between the temperature of reaction zone B ($T_B$) and the temperature of reaction zone A ($T_A$), i.e., $T_B$-$T_A$, is $\leq 0°$ C. and $\geq -20°$ C. or $\geq -10°$ C. or $\leq 0°$ C. and $\geq -5°$ C., or frequently $\leq 0°$ C. and $\geq -3°$ C.

When the process according to the invention is being performed under increased (preferred in accordance with the invention) propene hourly space velocities ($\geq 160$ l (STP)/l·h and $\leq 300$ l (STP)/l·h, or $\leq 600$ l (STP)/l·h), the $T^{maxA}$-$T^{maxB}$ differences required according to the invention are normally attained when, firstly, both the temperature of reaction zone A and the temperature of reaction zone B are in the range from 290 to 380° C. and $T_B$-$T_A$ is $\geq 0°$ C. and $\leq 50°$ C., or $\geq 5°$ C. and $\leq 45°$ C., or $\geq 10°$ C. and $\leq 40°$ C., or $\geq 15°$ C. and $\leq 30°$ C. or $\leq 35°$ C. (e.g. 20° C. or 25° C.).

The above statement regarding the $T_B$-$T_A$ temperature differences regularly also applies when the temperature of reaction zone A is within the preferred range of from 305 to 365° C. or within the particularly preferred range of from 310 to 340° C.

The propene hourly space velocity on the fixed catalyst bed in the process described may therefore be, for example, $\geq 90$ l (STP)/l·h and $\leq 300$ l (STP)/l h, or $\geq 110$ l (STP)/l·h and $\leq 280$ l (STP)/l·h or $\geq 130$ l (STP)/l·h and $\leq 260$ l (STP)/l·h, or $\geq 150$ l (STP)/l·h and $\leq 240$ l (STP)/l·h, or $\geq 170$ l (STP)/l·h and $\leq 220$ l (STP)/l·h, or $\geq 190$ l (STP)/l·h and $\leq 200$ l(STP)/l·h.

According to the invention, temperature zone A preferably extends up to a propene conversion of from 50 to 70% or from 60 to 70%, of the value, pursued in accordance with the invention, of $C^P$ in the second reaction stage.

In general, the difference $T^{maxC}$-$T^{maxD}$ in the process according to the invention will not be more than 75° C. According to the invention, $T^{maxC}$-$T^{maxD}$ is preferably $\geq 3°$ C. and $\leq 60°$ C. With very particular preference, $T^{maxC}$-$T^{maxD}$ in the process according to the invention is $\geq 5°$ C. and $\leq 40°$ C.

When the process according to the invention is being performed in the case of relatively low ($\geq 70$ l (STP)/l·h and $\leq 150$ l (STP)/l·h) acrolein hourly space velocities on fixed catalyst bed 3, the $T^{maxC}$-$T^{maxD}$ differences required according to the invention are normally attained when, firstly, both the temperature of reaction zone C and the temperature of reaction zone D are in the range from 230 to 320° C. and, secondly, the difference between the temperature of reaction zone D ($T_D$) and the temperature of reaction zone C ($T_C$), i.e., $T_D$-$T_C$, is $\leq 0°$C. and $\geq -20°$ C. or $\geq -10°$ C. or $\leq 0°$ C. and $\geq -5°$ C., or frequently $\leq 0°$ C. and $\geq -3°$ C.

When the process according to the invention is being performed under increased propene hourly space velocities and thus also increased acrolein hourly space velocities ($\geq 150$ l (STP)/l·h and $\leq 300$ l (STP)/l·h, or $\leq 600$ l (STP)/l·h), the $T^{maxC}$-$T^{maxD}$ differences required according to the invention are normally attained when, firstly, both the temperature of reaction zone C and the temperature of reaction zone D are in the range from 230 to 320° C. and $T_D$-$T^C$ is $\geq 0°$ C. and $\leq 40°$ C., or 5° C. and $\leq 35°$ C., or 30° C., or $\geq 10°$ C. and $\leq 25°$ C., or $\leq 20°$ C., or $\leq 15°$ C.

The above statement regarding the $T_D$-$T_C$ temperature differences regularly also applies when the temperature of reaction zone C is within the preferred range of from 250 to 300° C. or within the particularly preferred range of from 260 to 280° C.

The acrolein hourly space velocity on fixed catalyst bed 3 in the process according to the invention may therefore be, for example, $\geq 70$ l (STP)/l·h or $\geq 90$ l (STP)/l·h and $\leq 300$ l (STP)/l·h, or $\geq 110$ l (STP)/l·h and $\leq 280$ l (STP)/l·h or $\geq 130$ l (STP)/l·h and $\leq 260$ l (STP)/l·h, or $\geq 150$ l (STP)/l·h and $\leq 240$ l (STP)/l·h, or $\geq 170$ l (STP)/l·h and $\leq 220$ l (STP)/l·h, or $\geq 190$ l (STP)/l·h and $\leq 200$ l (STP)/l·h.

According to the invention, temperature zone C preferably extends up to an acrolein conversion of from 50 to 85% or from 60 to 85%, of the value for $C^A$ pursued in the third reaction stage.

The working pressure in both reaction stages of the process according to the invention may be either below atmospheric pressure (e.g. down to 0.5 bar) or above atmospheric pressure. Typically, the working pressure in both reaction stages of the process according to the invention will be at values of from 1 to 5 bar, frequently from 1 to 3 bar.

Normally, the reaction pressure will not excess 100 bar in either of the two reaction stages.

The selectivity of product-of-value formation in the above-described second reaction stage (sum of acrolein formation and acrylic acid by-product formation) in the case of suitable selection (see catalysts recommended in this document) of fixed catalyst bed 2 in a manner known per se will, in accordance with the invention, regularly be $\geq 92$ mol %, or $\geq 94$ mol %, frequently $\geq 95$ mol %, or $\geq 96$ mol % or $\geq 97$ mol %.

In general, the acrolein hourly space velocity on fixed catalyst bed 3 in the above-described process will also be at least about 10 l (STP)/l·h, frequently at least about 20 or 25 l (STP)/l·h, or at least 30 or 40 l (STP)/l·h, or at least 50 l (STP)/l·h, below the propene hourly space velocity on fixed catalyst bed 2. This can be attributed primarily to the fact that conversion of propene in the second reaction stage is conducted to a limited extent in accordance with the invention.

In the case of suitable selection of fixed catalyst beds 2 and 3 in a manner known per se (see catalyst recommendations given in this document), the selectivity of acrylic acid formation assessed over both reaction stages in the above-described procedure, based on converted propene, may, in accordance with the invention, regularly be at values of $\geq 83$ mol %, frequently at $\geq 85$ mol %, or $\geq 88$ mol %, often at $\geq 90$ mol %, or $\geq 93$ mol %.

It is essential for the procedure described that fixed catalyst bed 2 consists of at least two spatially successive fixed catalyst bed zones, the volume-specific activity within one fixed catalyst bed zone being substantially constant and increasing sharply at the transition from one fixed catalyst bed zone into another fixed catalyst bed zone in flow direction of reaction gas mixture 2.

The volume-specific (i.e. normalized to the unit of the particular bed volume) activity of a fixed catalyst bed zone can then be adjusted over the fixed catalyst bed zone in a substantially constant manner by starting from a basic amount of shaped catalyst bodies prepared in a uniform manner (their bed corresponds to the maximum achievable volume-specific activity) and homogeneously diluting it in the particular fixed catalyst bed zone with shaped bodies (shaped diluent bodies) which behave substantially inertly with regard to the heterogeneously catalyzed partial gas phase oxidation. The higher the proportion of shaped diluent bodies selected, the less the amount of active composition and catalyst activity is present in a certain volume of the bed. Useful materials for such inert shaped diluent bodies are in principle all of those which are suitable as support material for coated catalysts suitable in accordance with the invention.

Useful such materials include, for example, porous or nonporous aluminum oxides, silicon dioxide, thorium dioxide, zirconium dioxide, silicon carbide, silicates such as magnesium silicate or aluminum silicate or the steatite already mentioned (e.g. Steatite C-220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted with them.

According to the invention, it is favorable when the chemical composition of the active composition used does not vary over the entire fixed catalyst bed 2. In other words, although the active composition used for a single shaped catalyst body can be a mixture of different multimetal oxides comprising the elements Mo, Fe and Bi, the same mixture then has to be used for all shaped catalyst bodies of fixed catalyst bed 2.

A volume-specific activity increasing zone by zone over the fixed catalyst bed in flow direction of reaction gas mixture 2 can therefore be achieved for the process according to the invention in a simple manner, for example, by beginning the bed in a first fixed catalyst bed zone with a high proportion of inert shaped diluent bodies based on one type of shaped catalyst bodies, and then reducing this proportion of shaped diluent bodies zone by zone in flow direction.

However, a zone by zone increase in the volume-specific activity is also possible, for example, by increasing the thickness of the active composition layer applied to the support zone by zone at constant geometry and active composition type of a coated shaped catalyst body or, in a mixture of coated catalysts having the same geometry but having different proportions by weight of the active composition by increasing the proportion of shaped catalyst bodies having higher active composition content zone by zone. Alternatively, the active compositions themselves can be diluted in the course of the active composition preparation by, for example, incorporating inert, diluting materials such as hardfired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of coated catalysts (having identical active composition) by varying the mixing ratio in an appropriate manner. A variation in the volume-specific activity can also be achieved by the use of catalyst geometries having different bulk density (for example, in the case of unsupported catalysts having identical active composition of the different geometries). It is of course also possible to use the variants described in combination.

It is of course also possible to use mixtures of catalysts having chemically different active compositions and, as a consequence of this different composition, having different activity for fixed catalyst bed 2. These mixtures may in turn, zone by zone, be varied in their composition and/or be diluted with different amounts of inert shaped diluent bodies.

Upstream and/or downstream of fixed catalyst bed 2 may be disposed beds consisting exclusively of inert material (for example only shaped diluent bodies) (in this document, they are not included for terminology purposes in fixed catalyst bed 2, since they do not comprise any shaped bodies which have multimetal oxide active composition). The shaped diluent bodies used for the inert bed may have the same geometry as the shaped catalyst bodies used in fixed catalyst bed 2. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having a diameter d=4-5 mm. Temperature zones A and B in the process according to the invention may also extend to the inert beds. According to the invention, it is advantageous when neither temperature zone A nor temperature zone B covers more than three fixed catalyst bed zones (according to the invention, at least one fixed catalyst bed zone is necessarily covered by both temperature zones).

According to the invention, it is particularly advantageous when the entire fixed catalyst bed 2 comprises not more than five, appropriately not more than four or three, fixed catalyst bed zones.

According to the invention, at the transition from one fixed catalyst bed zone to another fixed catalyst bed zone (in flow direction of reaction gas mixture 2) of fixed catalyst bed 2, the volume-specific active composition (i.e. the weight of the multimetal oxide active composition present in the uniform bed volume) should (in the case of uniform active composition over the entire fixed catalyst bed 2) appropriately increase by at least 5% by weight, preferably by at least 10% by weight (this applies in particular in the case of uniform shaped catalyst bodies over the entire fixed catalyst bed 2). In general, this increase in the process according to the invention will not be more than 50% by weight, usually not more than 40% by weight. According to the invention, in the case of uniform active composition over the entire fixed catalyst bed 2, the difference in the volume-specific active composition of the fixed catalyst bed zone having the lowest volume-specific activity and the fixed catalyst bed zone having the highest volume-specific activity should also not be more than 50% by weight, preferably not more than 40% by weight, and generally not more than 30% by weight.

In the process according to the invention, fixed catalyst bed 2 will frequently consist of only two fixed catalyst bed zones.

According to the invention, preference is given to the last fixed catalyst bed zone of fixed catalyst bed 2 in flow direction of reaction gas mixture 2 being undiluted. In other words, it preferably consists exclusively of shaped catalyst bodies. If required, it may also consist of a bed of shaped catalyst bodies whose volume-specific activity is reduced, for example by dilution with inert material, for example by 10%.

When fixed catalyst bed 2 consists of only two fixed catalyst bed zones, it is generally advantageous according to the invention (as is quite generally the case in the process according to the invention) when the fixed catalyst bed zone having the highest volume-specific activity does not project into temperature zone A (in particular when the heating in temperature zone A and temperature zone B is effected by means of a flowing heat carrier which in each case flows in countercurrent to the reaction gas mixture). In other words, the fixed catalyst bed zone having the lower volume-specific activity will favorably project into temperature zone B and the fixed catalyst bed zone having the higher volume-specific activity will begin and end in temperature zone B (i.e. have its beginning beyond the transition from temperature zone A to temperature zone B).

When fixed catalyst bed 2 consists of only three fixed catalyst bed zones, it is generally equally advantageous according to the invention when the fixed catalyst bed zone having the higher volume-specific activity does not project into temperature zone A but begins and ends in temperature zone B, i.e. has its beginning beyond the transition from temperature zone A to temperature zone B (in particular when the heating in temperature zone A and temperature zone B is effected by means of a flowing heat carrier which in each case flows in countercurrent to the reaction gas mixture). In other words, the fixed catalyst bed zone having the second highest volume-specific activity will normally project into both temperature zone A and temperature zone B.

When fixed catalyst bed 2 consists of four fixed catalyst bed zones, it is generally advantageous in accordance with the invention when the fixed catalyst bed zone having the third highest volume-specific activity projects into both temperature zone A and into temperature zone B (in particular when the heating in temperature zone A and temperature zone B is effected by means of a flowing heat carrier which in each case flows in countercurrent to reaction gas mixture 2).

In the case of cocurrent flow of reaction gas mixture 2 and heat carriers in temperature zones A and B, it may be advantageous in the process according to the invention when the fixed catalyst bed zone having the highest volume-specific activity within fixed catalyst bed 2 projects into temperature zone A.

Generally, the volume-specific activity between two fixed catalyst bed zones of a fixed catalyst bed 2 can be differentiated experimentally in a simple manner by passing the same reaction gas mixture comprising propene, under identical boundary conditions (preferably the conditions of the contemplated process), over fixed catalyst beds of the same length, but in each case each according to the composition of the particular fixed catalyst bed zone. The higher amount of propene converted indicates the higher volume-specific activity.

When the total length of fixed catalyst bed 2 is $L^1$, it is advantageous in accordance with the invention if there is no transition from one fixed catalyst bed zone to another fixed catalyst bed zone within the region of $$X^1 \pm L^1 \frac{4}{100}$$

or within the region of $$X^1 \pm L^1 \frac{3}{100}$$

or within the region of $$X^1 \pm L^1 \frac{2}{100},$$

where X is the location (the position) within fixed catalyst bed 2 of the transition from temperature zone A to temperature zone B.

Preference is given to the fixed catalyst bed in the above-described process being structured as follows in flow direction of reaction gas mixture 2.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of fixed catalyst bed 2, a homogeneous mixture of shaped catalyst bodies and shaped diluent bodies (both preferably having substantially the same geometry), in which the proportion by weight of the shaped diluent bodies (the densities of shaped catalyst bodies and of shaped diluent bodies generally differ only slightly) is normally from 5 to 40% by weight, or from 10 to 40% by weight, or from 20 to 40% by weight, or from 25 to 35% by weight. This first zone of the fixed catalyst bed is advantageously followed up to the end of the length of the fixed catalyst bed (i.e., for example, to a length of from 2.00 to 3.00 m, preferably from 2.50 to 3.00 m) either by a bed of shaped catalyst bodies diluted only to a slighter extent (than in the first zone), or, most preferably, an unaccompanied (undiluted) bed of the same shaped catalyst bodies which have also been used in the first zone. The aforesaid applies in particular when the shaped catalyst bodies used in the fixed catalyst bed are unsupported catalyst rings or coated catalyst rings (in particular those which are specified as preferred in this document). For the purposes of the above-mentioned structuring, both the shaped catalyst bodies and the shaped diluent bodies in the process according to the invention advantageously have substantially the ring geometry 5 mm×3 mm×2 mm (external diameter×length×internal diameter).

The aforesaid also applies when, instead of inert shaped diluent bodies, shaped coated catalyst bodies are used whose active composition content is from 2 to 15% by weight lower than the active composition content of any shaped coated catalyst bodies used at the end of fixed catalyst bed 2.

A pure inert material bed whose length, based on the length of fixed catalyst bed 2, is advantageously from 5 to 20% generally precedes fixed catalyst bed 2 in flow direction of reaction gas mixture 2. It is normally utilized as a heating zone for reaction gas mixture 2. It is normally utilized as a heating zone for reaction gas mixture 2. Instead of the inert material bed, it is also possible to use catalyst bed diluted with inert material as a heating zone.

According to the invention, the fixed catalyst bed zone having the lower volume-specific activity in the aforementioned fixed catalyst beds 2 then advantageously extends into temperature zone B for from 5 to 20%, frequently from 5 to 15%, of its length.

Appropriately, temperature zone A also extends to a preliminary bed of inert material which is used if appropriate for fixed catalyst bed 2.

For the advantageousness of the procedure described, it is also essential that fixed catalyst bed 3 consists of at least two spatially successive fixed catalyst bed zones, and the volume-specific activity within one fixed catalyst bed zone is substantially constant and increases sharply in flow direction of reaction gas mixture 3 at the transition from one fixed catalyst bed zone to another fixed catalyst bed zone.

The volume-specific (i.e. normalized to the unit of the particular bed volume) activity of a fixed bed catalyst zone can then be adjusted over the fixed catalyst bed zone in a substantially constant manner by starting from a basic amount of shaped catalyst bodies prepared in a uniform manner (their bed corresponds to the maximum achievable volume-specific activity) and homogeneously diluting it in the particular fixed catalyst bed zone with shaped bodies (shaped diluent bodies) which behave substantially inertly with regard to the heterogeneously catalyzed partial gas phase oxidation. The higher the proportion of shaped diluent bodies selected, the less active composition, i.e. catalyst activity, is present in a certain volume of the bed. Useful materials for such inert shaped diluent bodies are in principle all of those which are suitable as support material for coated catalysts suitable according to the invention.

Useful such materials include, for example, porous or non-porous aluminum oxides, silicon dioxide, thorium dioxide, zirconium dioxide, silicon carbide, silicates such as magnesium silicate or aluminum silicate or the steatite already mentioned above (e.g. Steatite C-220 from CeramTec).

The geometry of such inert shaped diluent bodies may in principle be as desired. In other words, they may, for example, be spheres, polygons, solid cylinders or else rings. According to the invention, the inert shaped diluent bodies selected will preferably be those whose geometry corresponds to that of the shaped catalyst bodies to be diluted with them.

According to the invention, it is favorable when the chemical composition of the active composition used does not vary over the entire fixed catalyst bed 3. In other words, although the active composition used for a single shaped catalyst body can be a mixture of different multimetal oxides comprising the elements Mo and V, the same mixture then has to be used for all shaped catalyst bodies of fixed catalyst bed 3.

A volume-specific activity increasing zone by zone over fixed catalyst bed 3 in flow direction of reaction gas mixture 3 can therefore be achieved for the process described in a simple manner, for example, by beginning the bed in a first fixed catalyst bed zone with a high proportion of inert shaped diluent bodies based on one type of shaped catalyst bodies, and then reducing this proportion of shaped diluent bodies zone by zone in flow direction.

However, a zone by zone increase in the volume-specific activity is also possible, for example, by increasing the thickness of the active composition layer applied to the support zone by zone at constant geometry and active composition type of a coated shaped catalyst body or, in a mixture of coated catalysts having the same geometry but having different proportions by weight of the active composition by increasing the proportion of shaped catalyst bodies having higher proportion by weight of active composition content zone by zone. Alternatively, the active compositions themselves can be diluted in the course of the active composition preparation by, for example, incorporating inert, diluting materials such as hard-fired silica into the dry mixture of starting compounds to be calcined. Different amounts of diluting material added lead automatically to different activities. The more diluting material is added, the lower the resulting activity will be. A similar effect can also be achieved, for example, in the case of mixtures of unsupported catalysts and of coated catalysts (having identical active composition) by varying the mixing ratio in an appropriate manner. A variation in the volume-specific activity can also be achieved by the use of catalyst geometries having different bed densities (for example, in the case of unsupported catalysts having identical active compositions of the different geometries). It is of course also possible to use the variants described in combination.

It is of course also possible to use mixtures of catalysts having chemically different active composition and, as a consequence of this different composition, having different activity for fixed catalyst bed 3. These mixtures may in turn, zone by zone, be varied in their composition and/or be diluted with different amounts of inert shaped diluent bodies.

Upstream and/or downstream of fixed catalyst bed 3 may be disposed beds consisting exclusively of inert material (for example only shaped diluent bodies) (in this document, they are not included for terminology purposes in fixed catalyst bed 3, since they do not comprise any shaped bodies which have multimetal oxide active composition). The shaped diluent bodies used for the inert bed may have the same geometry as the shaped catalyst bodies used in the fixed catalyst bed. However, the geometry of the shaped diluent bodies used for the inert bed may also be different to the abovementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having a diameter d=4-5 mm. Temperature zones C and D in the process according to the invention may also extend to the inert beds. According to the invention, it is advantageous when neither temperature zone C nor temperature zone D covers more than three fixed catalyst bed zones (according to the invention, at least one fixed catalyst bed zone is necessarily covered by both temperature zones).

According to the invention, it is particularly advantageous when the entire fixed catalyst bed 3 comprises not more than five, advantageously not more than four or three, fixed catalyst bed zones.

According to the invention, at the transition from one fixed catalyst bed zone to another fixed catalyst bed zone (in flow direction of reaction gas mixture 3), the volume-specific active composition (i.e. the weight of the multimetal oxide active composition present in the uniform bed volume) should (in the case of uniform active composition over the entire fixed catalyst bed 3) advantageously increase by at least 5% by weight, preferably by at least 10% by weight (this applies in particular in the case of uniform shaped catalyst bodies over the entire fixed catalyst bed 3). In general, this increase in the process according to the invention will not be more than 50% by weight, usually not more than 40% by weight. According to the invention, in the case of uniform active composition over the entire fixed catalyst bed 3, the difference in the volume-specific active composition of the fixed catalyst bed zone having the lowest volume-specific activity and the fixed catalyst bed zone having the highest volume-specific activity should also not be more than 50% by weight, preferably not more than 40% by weight, and generally not more than 30% by weight.

In the process according to the invention, fixed catalyst bed 3 will frequently consist of only two fixed catalyst bed zones.

According to the invention, preference is given to the last fixed catalyst bed zone of fixed catalyst bed 3 in flow direction of reaction gas mixture 3 being undiluted. In other words, it preferably consists exclusively of shaped catalyst bodies. If required, it may also consist of a bed of shaped catalyst bodies whose volume-specific activity is reduced, for example by dilution with inert material, for example by 10%. When fixed catalyst bed 3 consists of only two fixed catalyst bed zones, it is generally advantageous according to the invention (as is quite generally the case in the process according to the invention) when the fixed catalyst bed zone having the highest volume-specific activity projects into temperature zone C (in particular when the heating in temperature zone C and temperature zone D is effected by means of a flowing heat carrier which in each case flows in countercurrent to reaction gas mixture 3).

When fixed catalyst bed 3 consists of only three fixed catalyst bed zones, it is generally equally advantageous according to the invention when the fixed catalyst bed zone having the highest volume-specific activity projects into temperature zone C (in particular when the heating in temperature zone C and temperature zone D is effected by means of a flowing heat carrier which in each case flows in countercurrent to reaction gas mixture 3).

When fixed catalyst bed 3 consists of four fixed catalyst bed zones, it is generally advantageous in accordance with the invention when the fixed catalyst bed zone having the second highest volume-specific activity projects both into temperature zone C and into temperature zone D (in particular when the heating in temperature zone C and temperature zone D is effected by means of a flowing heat carrier which in each case flows in countercurrent to reaction gas mixture 3).

In the case of cocurrent flow of reaction gas mixture 3 and heat carriers in temperature zones C and D, it may be advantageous in accordance with the invention if the fixed catalyst bed zone within fixed catalyst bed 3 having the highest volume-specific activity does not project into temperature zone C, but rather only has its beginning beyond the transition from temperature zone C to temperature zone D.

The volume-specific activity between two fixed catalyst bed zones within fixed catalyst bed 3 can be differentiated experimentally in a simple manner by passing the same starting reaction gas mixture comprising acrolein over fixed catalyst beds of the same length but each corresponding to the composition of the particular fixed catalyst bed zone under identical boundary conditions (preferably the conditions of the contemplated process). The higher amount of acrolein converted indicates the higher volume-specific activity.

When the total length of fixed catalyst bed 3 is $L^2$, it is advantageous in accordance with the invention if there is no transition from one fixed catalyst bed zone to another fixed catalyst bed zone within the region of $$X^2 \pm L^2 \frac{4}{100}$$

or within the region of $$X^2 \pm L^2 \frac{3}{100}$$

or within the region of $$X^2 \pm L^2 \frac{2}{100},$$

where X is the location within fixed catalyst bed 3 of the transition from temperature zone C to temperature zone D.

Preference is given to fixed catalyst bed 3 in the above-described process being structured as follows in flow direction of reaction gas mixture 3.

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of fixed catalyst bed 3, a homogeneous mixture or two (having decreasing dilution) successive homogeneous mixtures of shaped catalyst bodies and shaped diluent bodies (both preferably having substantially the same geometry), in which the proportion of shaped diluent bodies is such that the volume-specific active composition, based on a bed consisting only of shaped catalyst bodies, has been reduced by from 10 to 50% by weight, preferably from 20 to 45% by weight and more preferably from 25 to 35% by weight. According to the invention, this first or these first two zones are then advantageously followed to the end of the length of fixed catalyst bed 3 (i.e., for example, to a length of from 2.00 to 3.00 m, preferably from 2.50 to 3.00 m) by either a bed of the shaped catalyst bodies diluted only to a slighter extent (than in the first or in the first two zones) or, most preferably, an unaccompanied bed of the same shaped catalyst bodies which have also been used in the first zones.

The aforementioned applies in particular when the shaped catalyst bodies used in fixed catalyst bed 3 are coated catalyst rings or coated catalyst spheres (in particular those which are listed in this document as preferred). It is advantageous when, for the purposes of the aforementioned structuring, both the shaped catalyst bodies or their support rings and the shaped diluent bodies in the process according to the invention substantially have the ring geometry 7 mm×3 mm×4 mm (external diameter×length×internal diameter).

The abovementioned also applies when, instead of inert shaped diluent bodies, shaped coated catalyst bodies are used whose active composition content is from 2 to 15% by weight lower than the active composition content of the shaped coated catalyst bodies at the end of fixed catalyst bed 3.

A pure inert material bed whose length, based on the length of fixed catalyst bed 3, is advantageously from 5 to 20% generally precedes fixed catalyst bed 3 in flow direction of reaction gas mixture 3. It normally serves the purpose of heating reaction gas mixture 3. Instead of the inert material bed, it is also possible to use a catalyst bed diluted with inert material as a heating zone.

It is advantageous in accordance with the invention when temperature zone C (which also advantageously extends in accordance with the invention to the preliminary bed of inert material) in the abovementioned fixed catalyst bed 3 extends for from 5 to 20%, frequently from 5 to 15%, of its length to the last (volume-specifically most active) fixed catalyst bed zone of fixed catalyst bed 3 in flow direction of reaction gas mixture 3.

In an advantageous manner from an application point of view, the second reaction stage of the above-described process is carried out in a two-zone tube bundle reactor, as described, for example, in DE-A 19910508, 19948523, 19910506 and 19948241. A preferred variant of a two-zone tube bundle reactor which can be used in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903218 are also suitable for carrying out the second reaction stage of the above-described process.

In other words, in the simplest manner, the fixed catalyst bed 2 to be used in accordance with the invention (possibly with downstream and/or upstream inert beds) is disposed in the metal tubes of a tube bundle reactor and two substantially spatially separated heating media, generally salt melts, are conducted around the metal tubes. The tube section over which the particular salt bath extends represents a temperature zone in accordance with the invention. In other words, in the simplest manner, for example, a salt bath A flows around that section of the tubes (temperature zone A) in which the oxidative conversion of propene (in single pass) proceeds until a conversion in the range from 40 to 80% of the $C^P$ value being pursued in accordance with the invention in the second reaction stage is achieved, and a salt bath B flows around the section of the tubes (reaction zone B) in which the subsequent oxidative conversion of propene (in single pass) proceeds until the value of $C^P$ being pursued in accordance with the invention is achieved (if required, the temperature zones A, B to be used in accordance with the invention may be followed by further reaction zones which are maintained at individual temperatures).

It is appropriate from an application point of view for the second reaction stage described not to include any further temperature zones. In other words, salt bath B appropriately flows around the section of the tubes in which the subsequent oxidative conversion of propene (in single pass) proceeds up to the $C^P$ value being pursued in accordance with the invention.

Typically, the beginning of temperature zone B lies beyond the hotspot maximum of temperature zone A.

According to the invention, both salt baths A, B can be conducted in cocurrent or in countercurrent through the space surrounding the reaction tubes relative to the flow direction of the reaction gas mixture flowing through the reaction tubes. It is of course also possible in accordance with the invention to employ cocurrent flow in temperature zone A and countercurrent flow in temperature zone B (or vice versa).

In all of the aforementioned cases, it is of course possible to superimpose a transverse flow on the parallel flow of the salt melt, relative to the reaction tubes, taking place within the particular temperature zone, so that the individual reaction zone corresponds to a tube bundle reactor as described in EP-A 700714 or in EP-A 700893, which results overall in a meandering flow profile of the heat exchange medium in a longitudinal section through the catalyst tube bundle.

Appropriately, starting reaction gas mixture 2 in the process according to the invention is fed to fixed catalyst bed 2 preheated to the reaction temperature.

Typically, the catalyst tubes in the two-zone tube bundle reactors are manufactured from ferritic steel and typically have a wall thickness of from 1 to 3 mm. Their internal diameter is generally from 20 to 30 mm, frequently from 21 to 26 mm. Their length is advantageously from 2 to 4 m, preferably from 2.5 to 3.5 m. In each temperature zone, the fixed bed catalyst charge 1 ccupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (known as the catalyst tube pitch) is from 35 to 45 mm (cf., for example, EP-B 468290).

Suitable heat exchange media for the two-zone method are also in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the aforementioned flow arrangements in the two-zone tube bundle reactors, the flow rate within the two heat exchange medium circuits required is selected in such a way that the temperature of the heat exchange medium rises from the entrance into the temperature zone to the exit from the temperature zone (as a result of the exothermicity of the reaction) by from 0 to 15° C. In other words, the aforementioned $\Delta T$ may, in accordance with the invention, be from 1 to 10° C., or from 2 to 8° C., or from 3 to 6° C.

According to the invention, the entrance temperature of the heat exchange medium into temperature zone A is normally in the range from 290 to 380° C., preferably in the range from 305 to 365° C. and more preferably in the range from 310 to 340° C. or is 330° C. According to the invention, in the case of propene hourly space velocities on fixed catalyst bed 2 of $\geq 90$ l (STP)/l·h and $\leq 160$ l (STP)/l·h, the entrance temperature of the heat exchange medium into temperature zone B is likewise in the range from 290 to 380° C., but at the same time normally, appropriately in accordance with the invention, from $\geq 0°$ C. to $\leq 20°$ C., or $\leq 10°$ C., or $\geq 0°$ C. and $\leq 5°$ C., or frequently $\geq 0°$ C. and $\leq 3°$ C., below the entrance temperature of the heat exchange medium entering temperature zone A. According to the invention, in the case of propene hourly space velocities on fixed catalyst bed 2 of $\geq 160$ l (STP)/l·h and (generally) $\leq 300$ l (STP)/l·h (or 600 l (STP)/l·h), the entrance temperature of the heat exchange medium into temperature zone B will likewise be in the range from 290 to 380° C., but normally, appropriately in accordance with the invention, from $\geq 0°$ C to $\leq 50°$ C., or $\geq 5°$ C. and $\leq 45°$ C., or $\geq 10°$ C. and $\leq 40°$ C., or $\geq 15°$ C. and $\leq 30°$ C. or $\leq 35°$ C. (for example 20° C. or 25° C.), above the entrance temperature of the heat exchange medium entering temperature zone A.

It should be pointed out once again at this juncture that, for an implementation of reaction stage 2 of the process according to the invention, it is also possible in particular to use the two-zone tube bundle reactor type which is described in DE-B 2201528 and includes the possibility of removing a portion of the hotter heat exchange medium of temperature zone B to temperature zone A, in order if appropriate to heat a cold starting reaction gas mixture 2 or a cold cycle gas. The tube bundle characteristics within an individual temperature zone may also be configured as described in EP-A 382098.

Otherwise, it has been found to be appropriate to cool the product gas mixture 2 leaving the second reaction stage in a direct and/or indirect manner before it enters the third reaction stage, in order to suppress subsequent complete combustion of portions of the acrolein formed in the second reaction stage. To this end, an aftercooler is typically connected between the two reaction stages. In the simplest case, this may be an indirect tube bundle heat transferrer. In this case, product gas mixture 2 is generally conducted through the tubes and a heat exchange medium is conducted around the tubes and may be of the type corresponding to the heat exchange media recommended for the tube bundle reactors. Advantageously, the tube interior is filled with inert random packings (for example spirals of stainless steel, rings of steatite, spheres of steatite, etc.). These improve the heat exchange and capture any molybdenum trioxide subliming from the fixed catalyst bed 2 of the second reaction stage before it enters the third reaction stage. It is advantageous for the aftercooler to be manufactured from stainless steel coated with zinc silicate primer.

According to the invention, the resulting selectivity of acrolein formation and also of acrylic acid by-product formation together in single pass in the second reaction stage will regularly be $\geq 92$ mol % or $\geq 94$ mol %, frequently $\geq 95$ mol % or $\geq 96$ mol % or $\geq 97$ mol %.

It is appropriate from an application point of view to cool the product gas mixture 2 of the second reaction stage in the aftercooler already mentioned to a temperature of from 210 to 290° C., frequently from 230 to 280° C. or from 250 to 270° C. The product gas mixture 2 of the second reaction stage can quite possibly be cooled to temperatures which are below the temperature of the third reaction stage. However, the aftercooling described is no way obligatory and can generally be dispensed with, especially when the path of product gas mixture 2 from the second reaction stage to the third reaction stage is kept short. Advantageously, the two-stage partial oxidation process described is also realized in such a way that the oxygen requirement in the third reaction stage is not already covered by an appropriately high oxygen content of starting reaction gas mixture 2, but rather that the required oxygen is added in the region between the second and third reaction stages ("secondary oxygen addition"). This may be effected before, during, after and/or for aftercooling. Useful sources for the molecular oxygen required in the third reaction stage include both pure oxygen and mixtures of oxygen and inert gas, for example air (preferred in accordance with the invention) or air depleted in molecular nitrogen (for example, ≧90% by volume of $O_2$, ≦10% by volume of $N_2$). The oxygen source is regularly added compressed to the reaction pressure. The oxygen requirement in the third reaction stage of the process according to the invention can of course already be covered by an appropriately high oxygen requirement in the second reaction stage. If required, an inert diluent gas can of course also be added as a secondary gas.

Like the implementation of the second reaction stage, the third reaction stage of the process according to the invention is also implemented in an appropriate manner from an application point of view in a two-zone tube bundle reactor, as has already been described for the second reaction stage. The remarks regarding the two-zone tube bundle reactor for the second reaction stage therefore also apply to the two-zone tube bundle reactor for the third reaction stage.

In other words, the fixed catalyst bed 3 (including any inert beds) to be used in accordance with the invention is disposed in a simple manner in the metal tubes of a tube bundle reactor and two substantially spatially separated heating media, generally salt melts, are conducted around the metal tubes. According to the invention, the tube section over which the respective salt bath extends represents a temperature zone.

In other words, for example, a salt bath C flows around those sections of the tubes (temperature zone C) in which the oxidative conversion of acrolein (in single pass) proceeds until a conversion value in the range from 45 to 85% (preferably from 50 to 85%, more preferably from 60 to 85%, of the value of $C^A$ pursued in accordance with the invention in the third reaction stage) is achieved, and a salt bath D flows around the section of the tubes (temperature zone D) in which the subsequent oxidative conversion of acrolein (in single pass) proceeds until the inventive value of $C^A$ is achieved (if required, the temperature zones C, D to be used in accordance with the invention may be followed by further temperature zones which are maintained at individual temperatures).

It is appropriate from an application point of view for reaction stage 3 of the process according to the invention not to include any further temperature zones. In other words, salt bath D advantageously flows around the section of the tubes in which the subsequent oxidative conversion of acrolein (in single pass) proceeds to the value of $C^A$ pursued in accordance with the invention.

Typically, the beginning of temperature zone D lies beyond the hotspot maximum of temperature zone C.

According to the invention, both salt baths C, D can be conducted in cocurrent or in countercurrent through the space surrounding the reaction tubes relative to the flow direction of reaction gas mixture 3 flowing through the reaction tubes. It is of course also possible in accordance with the invention to employ cocurrent flow in temperature zone C and countercurrent flow in temperature zone D (or vice versa).

In all of the aforementioned cases, it is of course possible to superimpose a transverse flow on the parallel flow of the salt melt, relative to the reaction tubes, taking place within the particular temperature zone, so that the individual reaction zone corresponds to a tube bundle reactor as described in EP-A 700714 or in EP-A 700893, which results overall in a meandering flow profile of the heat exchange medium in a longitudinal section through the catalyst tube bundle.

Typically, the catalyst tubes in the aforementioned two-zone tube bundle reactors for the third reaction stage are manufactured from ferritic steel and typically have a wall thickness of from 1 to 3 mm. Their internal diameter is generally from 20 to 30 mm, frequently from 21 to 26 mm. Their length is advantageously from 3 to 4 m, preferably 3.5 m. In each temperature zone, fixed catalyst bed 3 occupies at least 60%, or at least 75%, or at least 90%, of the length of the zone. Any remaining length is optionally occupied by an inert bed. It is advantageous from an application point of view for the number of catalyst tubes accommodated in the tube bundle vessel to be at least 5000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally homogeneously distributed (preferably 6 equidistant adjacent tubes per catalyst tube), and the distribution is advantageously selected in such a way that the separation of the central internal axes of immediately adjacent catalyst tubes (known as the catalyst tube pitch) is from 35 to 45 mm (cf. EP-B 468290).

Suitable heat exchange media are in particular fluid heating media. It is particularly favorable to use melts of salts such as potassium nitrate, potassium nitrite, sodium nitrite and/or sodium nitrate, or of low-melting metals such as sodium, mercury and also alloys of different metals.

In general, in all of the abovementioned flow arrangements in the two-zone tube bundle reactors of the third reaction stage, the flow rate within the two heat exchange medium circuits required is selected in such a way that the temperature of the heat exchange medium rises from the entrance into the temperature zone to the exit from the temperature zone by from 0 to 15° C. In other words, the aforementioned ΔT may, in accordance with the invention, be from 1 to 10° C., or from 2 to 8° C., or from 3 to 6° C.

According to the invention, the entrance temperature of the heat exchange medium into temperature zone C is normally in the range from 230 to 320° C., preferably in the range from 250 to 300° C. and more preferably in the range from 260 to 280° C. According to the invention, in the case of acrolein hourly space velocities on fixed catalyst bed 3 of ≧70 l (STP)/l·h and ≦150 l (STP)/l·h, the entrance temperature of the heat exchange medium into temperature zone D is likewise in the range from 230 to 320° C., but at the same time normally, advantageously in accordance with the invention, from ≧0° C. to ≦20° C. or ≦10° C., or ≧0° C. and ≦5° C., or frequently ≧0° C. and ≦3° C., below the entrance temperature of the heat exchange medium entering temperature zone C. According to the invention, in the case of acrolein hourly space velocities on the fixed catalyst bed 3 of ≧150 l (STP)/l·h and (generally) ≦300 l (STP)/l·h (or 600 l (STP)/l·h), the entrance temperature of the heat exchange medium into temperature zone D will likewise be in the range from 230 to 320° C., but at the same time normally, advantageously in accordance with the invention, from ≧0° C. to ≦40° C., or ≧5° C. and ≦35° C., or 30° C., or ≧10° C. and ≦25° C., or 20° C., or 15° C., above the entrance temperature of the heat exchange medium entering temperature zone C.

It should be pointed out once again at this juncture that, for an implementation of the third reaction stage of the process described, it is also possible in particular to use the two-zone tube bundle reactor type which is described in DE-B 2201528 and includes the possibility of removing a portion of the hotter heat exchange medium of temperature zone D to temperature zone C, in order if appropriate to heat a starting reaction gas mixture 3 which is too cold. The tube bundle characteristics within an individual reaction zone may also be configured as described in EP-A 382098.

It is of course also possible to carry out the process described by combining two two-zone tube bundle reactors to give a four-zone tube bundle reactor, as described in WO 01/36364. In these cases, there is normally an inert bed between fixed catalyst bed 2 and fixed catalyst bed 3. However, such an intermediate inert bed may also be dispensed with. The length of the reaction tubes in the event of combination corresponds in many cases to the sum of the lengths of the uncombined tube bundle reactors.

It should be emphasized at this juncture that the multimetal oxide compositions of DE-A 102 61 186 are also favorable as active compositions both for fixed catalyst bed 2 and for fixed catalyst bed 3.

Favorable designs of a two-zone tube bundle reactor for the second reaction stage may have the following construction (the detailed configuration of the construction can be as described in the utility model applications 202 19 277.6, 2002 19 278.4 and 202 19 279.2 or in the PCT applications PCT/EP02/14187, PCT/EP02/14188 or PCT/EP02/14189):

| Catalyst tubes: | |
|---|---|
| material of the catalyst tubes: | ferritic steel; |
| dimensions of the catalyst tubes: | length, for example, 3500 mm; external diameter, for example, 30 mm; wall thickness, for example, 2 mm; | number of catalyst tubes in the tube bundle: for example, 30 000, or 28 000, or 32 000, or 34 000, or 36 000, or more; in addition up to 10 thermal tubes (as described in EP-A 873 783 and EP-A 12 70 065) which are charged in the same way as the catalyst tubes (in a spiral manner rotating from the very outside toward the inside), for example of the same length and wall thickness but having an external diameter of, for example, 33.4 mm and a centered thermowell of external diameter, for example, 10 mm and wall thickness of, for example, 1 mm;
reactor (same material as the catalyst tubes):
cylindrical vessel of internal diameter 6000-8000 mm;
reactor hoods plated with type 1.4541 stainless steel; plating thickness: a few mm;
annularly arranged tube bundle, for example with free central space:
diameter of the free central space: for example, 1000-2500 mm (for example 1200 mm, or 1400 mm, or 1600 mm, or 1800 mm, or 2000 mm, or 2200 mm, or 2400 mm);
normally homogeneous catalyst tube pitch in the tube bundle (6 equidistant adjacent tubes per catalyst tube), arrangement in an equilateral triangle, catalyst tube pitch (separation of the central internal axes of immediately adjacent catalyst tubes): 35-45 mm, for example 36 mm, or 38 mm, or 40 mm, or 42 mm, or 44 mm;
the catalyst tubes are secured and sealed by their ends in catalyst tube plates (upper plate and lower plate each having a thickness, for example, of 100-200 mm) and open at their upper ends into a hood joined to the vessel which has an inlet for starting reaction gas mixture 2; a separating plate of thickness 20-100 mm disposed, for example, at half the catalyst tube length, divides the reactor space symmetrically into two temperature zones A (upper zone) and B (lower zone); each temperature zone is divided into 2 equidistant longitudinal sections by a deflecting plate;
the deflecting plate preferably has annular geometry; the catalyst tubes are advantageously secured and sealed at the separating plate; they are not secured and sealed at the deflecting plates, so that the transverse flow rate of the salt melt within one zone is very constant;
each zone is provided with salt melt as a heat carrier by a dedicated salt pump; the feed of the salt melt is, for example, below the deflecting plate and the withdrawal is, for example, above the deflecting plate;
a substream is, for example, removed from both salt melt circuits and cooled, for example, in one common or two separate indirect heat exchangers (steam-raising);
in the first case, the cooled salt melt stream is divided, combined with the particular residual stream and pressurized into the reactor by the particular pump into the appropriate annular channel which divides the salt melt over the circumference of the vessel;
the salt melt reaches the tube bundle through the window disposed in the reactor jacket; the flow is, for example, in a radial direction to the tube bundle;
in each zone, the salt melt flows around the catalyst tubes as dictated by the deflection plate, for example in the sequence
  from the outside inward,
  from the inside outward;
through windows mounted around the circumference of the vessel, the salt melt collects at the end of each zone in an annular channel disposed around the reactor jacket, in order to be pumped in a circuit including substream cooling;
the salt melt is conducted from bottom to top through each temperature zone.

The reaction gas mixture leaves the reactor of the second stage at a temperature a few degrees higher than the salt bath entrance temperature of the reactor. For further processing, the reaction gas mixture is advantageously cooled to from 220° C. to 280° C., preferably from 240° C. to 260° C., in a separate aftercooler which is connected downstream of the reactor of the 2nd stage.

The aftercooler is generally flanged on below the lower tube plate and normally consists of tubes of ferritic steel. Stainless steel sheet metal spirals which may be partly or fully wound are advantageously introduced into the interior of the tubes of the aftercooler, in order to improve the heat transfer.
Salt Melt:

The salt melt used may be a mixture of 53% by weight of potassium nitrate, 40% by weight of sodium nitrite and 7% by weight of sodium nitrate; both reaction zones and the aftercooler advantageously employ a salt melt of the same composition; the amount of salt pumped by circulation in the reaction zones may be approx. 10 000 m³/h per zone.
Flow Control:

The starting reaction gas mixture 2 advantageously flows from top to bottom through the second stage reactor, while the salt melts having different temperatures of the individual zones are advantageously conveyed from bottom to top;
Catalyst tube and thermal tube charge (from top to bottom), for example:

Section 1: length 50 cm
  steatite rings of geometry 7 mm × 7 mm × 4 mm (external diameter × length × internal diameter) as a preliminary bed.
Section 2: length 140 cm
  catalyst charge of a homogeneous mixture of 20% by weight of steatite rings of geometry 5 mm × 3 mm × 2 mm (external diameter × length × internal diameter) and 80% by weight of unsupported catalyst from section 3 (alternatively, it is also possible to use a homogeneous mixture of 30% by weight of -continued

|  |  |
|---|---|
| | aforesaid steatite rings and only 70% by weight of unsupported catalyst from section 3). |
| Section 3: | length 160 cm<br>catalyst charge of annular (5 mm × 3 mm × 2 mm = external diameter × length × internal diameter) unsupported catalyst according to example 1 of DE-A 10046957 (stoichiometry: $[Bi_2W_2O_9 \times 2\,WO_3]_{0.5}\,[Mo_{12}Co_{5.5}Fe_{2.94}Si_{1.59}K_{0.08}O_x]_1)$. |

Favorable configurations of a two-zone tube bundle reactor for the third reaction stage can be designed as follows:

Everything as in the two-zone tube bundle reactor for the second reaction stage. However, the thickness of the upper and lower catalyst tube plates is frequently 100-200 mm, for example 110 mm, or 130 mm, or 150 mm, or 170 mm, or 190 mm.

The aftercooler is dispensed with; instead, the lower openings of the catalyst tubes open into a hood which is connected to the vessel at the lower end and has an outlet for the product gas mixture; the upper temperature zone is zone C and the lower temperature zone is zone D. Between the "aftercooler" outlet and the "reactor for the third reaction stage" inlet there is advantageously a means for feeding compressed air.

The catalyst tube and thermal tube charge (from top to bottom) may, for example, be as follows:

|  |  |
|---|---|
| Section 1: | length 20 cm<br>steatite rings of geometry 7 mm × 7 mm × 4 mm (external diameter × length × internal diameter) as a preliminary bed. |
| Section 2: | length 90 cm<br>catalyst charge of a homogeneous mixture of 20% by weight of steatite rings of geometry 7 mm × 3 mm × 4 mm (external diameter × length × internal diameter) and 80% by weight of coated catalyst from section 4 (alternatively, it is also possible to use a homogeneous mixture of only 70% by weight of coated catalyst from section 4 and 30% by weight of the aforementioned steatite rings). |
| Section 3: | length 50 cm<br>catalyst charge of a homogeneous mixture of 15% by weight of steatite rings of geometry 7 mm × 3 mm × 4 mm (external diameter × length × internal diameter) and 85% by weight of coated catalyst from section 4 (alternatively, it is also possible to use a homogeneous mixture of only 80% by weight of coated catalyst from section 4 and 20% by weight of the aforementioned steatite rings). |
| Section 4: | length 190 cm<br>catalyst charge of annular (7 mm × 3 mm × 4 mm = external diameter × length × internal diameter) coated catalyst according to preparative example 5 of DE-A 10046928 (stoichiometry: $Mo_{12}V_3W_{1.2}Cu_{2.4}O_x$). |

The third stage catalyst tube and thermal tube charge may also have the following appearance (from top to bottom):

|  |  |
|---|---|
| Section 1: | length 20 cm<br>steatite rings of geometry 7 mm × 7 mm × 4 mm (external diameter × length × internal diameter) as a preliminary bed. |
| Section 2: | length 140 cm<br>catalyst charge of a homogeneous mixture of 20% by weight of steatite rings of geometry 7 mm × 3 mm × 4 mm (external diameter × length × internal diameter) and 80% by weight of coated catalyst from section 3 (alternatively, it is also possible to use a homogeneous mixture of only 75% by weight of coated catalyst from section 3 and 25% by weight of the aforementioned steatite rings). |
| Section 3: | length 190 cm<br>catalyst charge of annular (7 mm × 3 mm × 4 mm = external diameter × length × internal diameter) coated catalyst according to preparative example 5 of DE-A 10046928 (stoichiometry: $Mo_{12}V_3W_{1.2}Cu_{2.4}O_x$). |

In the second stage charge mentioned, the unsupported catalyst from example 1 of DE-A 100 46 957 may also be replaced by:

a) a catalyst according to example 1c of EP-A 15565 or a catalyst to be prepared in accordance with this example, except having the active composition $Mo_{12}Ni_{6.5}Zn_2Fe_2Bi_1P_{0.0065}K_{0.06}O_x \cdot 10\,SiO_2$;

b) example no. 3 of DE-A 19855913 as an unsupported hollow cylinder catalyst of geometry 5 mm×3 mm×2 mm or 5 mm×2 mm×2 mm;

c) unsupported multimetal oxide II catalyst according to example 1 of DE-A 197 46 210;

d) one of the coated catalysts 1, 2 and 3 of DE-A 100 63 162, except applied in the same coating thickness to support rings of geometry 5 mm×3 mm×1.5 mm or 7 mm×3 mm×1.5 mm;

e) the catalysts, especially the working examples, of DE-A 10344149 and DE-A 10353954.

In all of the abovementioned third stage charges, the coated catalyst may be replaced in accordance with preparative example 5 of DE-A 100 46 928 by:

a) coated catalyst S1 or S7 from DE-A 4442346 having an active composition content of 27% by weight and a coating thickness of 230 μm;

b) a coated catalyst according to examples 1 to 5 of DE 19815281, except applied to support rings of geometry 7 mm×3 mm×4 mm having an active composition content of 20% by weight;

c) coated catalyst having biphasic active composition of stoichiometry $(Mo_{10.4}V_3W_{1.2}O_x)\,(CuMo_{0.5}W_{0.5}O_4)_{1.6}$, prepared according to DE-A 1973610 and having an active composition content of 20% by weight, applied to the aforementioned 7 mm×3 mm×4 mm support.

According to the invention, fixed catalyst bed 2 and fixed catalyst bed 3 are appropriately otherwise selected in such a way (for example by dilution with, for example, inert material) that the temperature difference between the hotspot maximum of the reaction gas mixture in the individual reaction zones and the particular temperature of the reaction zone generally does not exceed 80° C. This temperature difference is usually ≦70° C., frequently from 20 to 70° C.; this temperature difference is preferably small. For safety reasons, the fixed catalyst beds are also selected in a manner known per se to those skilled in the art (for example by dilution with, for example, inert material) in such a way that the peak-to-salt-temperature sensitivity as defined in EP-A 1106598 is ≦9° C., or ≦7° C., or ≦5° C., or ≦3° C.

Aftercooler and reactor for the third stage are connected by a connecting tube whose length is less than 25 m.

In the reactor arrangement above, the annular shaped diluent bodies and the annular shaped catalyst bodies in the third reaction stage may also be replaced by spherical shaped diluent bodies and spherical shaped catalyst bodies (each having a radius from 2 to 5 mm and having an active composition content of from 10 to 30% by weight, frequently from 10 to 20% by weight).

The product gas mixture 3 which leaves the process according to the invention after the third reaction stage is generally composed substantially of the acrylic acid target product, unconverted molecular oxygen (with a view to the lifetime of the catalysts used, it is favorable when the oxygen content in product gas mixture 3 is still from at least 1.5 to 4% by volume), propane, unconverted propylene, molecular nitrogen, steam which has formed as a by-product and/or has been used as a diluent gas, carbon oxides which have been used as a by-product and/or as a diluent gas, and small amounts of other lower aldehydes, lower alkanecarboxylic acids (e.g. acetic acid, formic acid and propionic acid) and maleic anhydride, benzaldehyde, aromatic carboxylic acids and aromatic carboxylic anhydrides (e.g. phthalic anhydride and benzoic acid), in some cases further hydrocarbons, for example C4 hydrocarbons (e.g. butene-1 and possibly other butenes), and other inert diluent gases.

The target product may be removed from product gas mixture 3 in a manner known per se in a separating zone (for example by partial or full and, if appropriate, fractional condensation of acrylic acid, or by absorption of acrylic acid in water or in a high-boiling hydrophobic organic solvent and subsequent workup of the condensates and/or absorbates; according to the invention, product gas mixture 3 will preferably be fractionally condensed; cf., for example, EP-A 13 88 533, EP-A 13 88 532, DE-A 102 35 847, EP-A 79 28 67, WO 98/01415, EP-A 10 15 411, EP-A 10 15 410, WO 99/50219, WO 00/53560, WO 02/09839, DE-A 102 35 847, WO 03/041833, DE-A 102 23 058, DE-A 102 43 625, DE-A 103 36 386, EP-A 85 41 29, U.S. Pat. No. 4,317,926, DE-A 198 37 520, DE-A 196 06 877, DE-A 19 50 1325, DE-A 102 47 240, DE-A 197 40 253, EP-A 69 57 36, EP-A 98 22 87, EP-A 10 41 062, EP-A 11 71 46, DE-A 43 08 087, DE-A 43 35 172, DE-A 44 36 243, DE-A 19 924 532, DE-A 103 32 758 and DE-A 19 924 533). An acrylic acid removal may also be undertaken as in EP-A 98 22 87, EP-A 98 22 89, DE-A 103 36 386, DE-A 101 15 277, DE-A 196 06 877, DE-A 197 40 252, DE-A 196 27 847, EP-A 92 04 08, EP-A 10 68 174, EP-A 10 66 239, EP-A 10 66 240, WO 00/53560, WO 00/53561, DE-A 100 53 086 and EP-A 98 22 88. Preference is given to removing as described in FIG. 7 of WO/0196271 or as described in DE-A 10 2004 032 129 and its equivalent patents. Favorable removal methods are also the processes described in the documents WO 2004/063138, WO 2004/035514, DE-A 102 43 625 and DE-A 102 35 847. Crude acrylic acid obtained in this way may be further processed, for example, as described in the documents WO 01/77056, WO 03/041832, WO 02/055469, WO 03/078378 and WO 03/041833.

A common feature of the above separating processes is (as already mentioned at the outset) that a residual gas stream which comprises substantially those constituents of product gas mixture 3 whose boiling point at standard pressure (1 bar) is $\leq -30°$ C. (i.e. the constituents which are difficult to condense or else volatile) normally remains at the top of the particular separating column which comprises separating internals and in whose lower section product gas mixture 3 is fed, normally after preceding direct and/or indirect cooling thereof.

In the lower section of the separating column, the less volatile constituents of product gas mixture 3, including the acrylic acid target product, are normally obtained in the condensed phase.

The residual gas constituents are primarily propane, propylene which has not been converted in the partial oxidation, molecular oxygen and other inert diluent gases which are frequently also used in the partial oxidation, for example nitrogen and carbon dioxide. Depending on the separation process employed, steam may be present in the residual gas only in traces or in amounts of up to 20% by volume or more.

The propane and propylene present in this (main) residual gas is, as already described, recycled in accordance with the invention.

In the workup of the condensed phase (for the purpose of removing the target product), further residual gases may occur, since it will advantageously be attempted in accordance with the invention to recycle the total amount of unconverted propane and propylene present in product gas mixture 3 or 2 into the first reaction stage (for example into the heterogeneously catalyzed propane dehydrogenation and/or propane oxydehydrogenation). Although these generally still comprise propane and propylene, they frequently no longer comprise any molecular oxygen. Typically, they are recycled, combined with the main residual gas to give an overall residual gas, into the first reaction stage (for example into the heterogeneously catalyzed propane dehydrogenation and/or propane oxydehydrogenation). However, it is also possible to separately recycle these residual gases, for example also into the second and/or third reaction stage.

The preferably full recycling of the remaining propane and propylene thus allows continuous conversion of propane to acrylic acid in continuous operation.

In this context, it is essential to the invention that the recycling described into the first reaction stage makes it possible to achieve therein a conversion over the entire process of propane to propylene with virtually one hundred percent selectivity in spite of restricted propylene conversion in reaction stage 2.

The advantageousness of such a procedure exists both at lower ($\leq 30$ mol %) and at high ($\geq 30$ mol %) dehydrogenation conversions (based on single pass of fresh propane through the dehydrogenation). Generally, it is favorable in the case of such recycling of oxidation cycle gas when the hydrogen content in starting reaction gas mixture 1 is in an at least stoichiometric ratio (based on oxygen combustion to water) to the amount of oxygen recycled into starting reaction gas mixture 1 via oxidation cycle gas.

The inventive cycle gas method can be employed correspondingly when the partial oxidation is a partial ammoxidation of propene to acrylonitrile. It can even be employed correspondingly when propane is replaced by isobutane in the dehydrogenation and the resulting isobutene is partially oxidized in a corresponding manner in a partial oxidation to methacrolein and/or methacrylic acid.

One advantage of the inventive procedure is in principle that, at all points in this document, including the working example which follows, wherever catalyst charges diluted with inert material are described and/or required, the corresponding catalysts can also be used undiluted for the same bed length.

At this point, it should also be emphasized once again that acrylic acid is removed from a product gas mixture 3 obtained in accordance with the invention (in particular also from the product gas mixture 3 of the working example of this document) preferably in such a way that the product gas mixture 3 which has been cooled beforehand if appropriate by direct and/or indirect cooling is fractionally condensed, ascending into itself, in a column comprising separating internals with side draw removal of crude acrylic acid, and/or absorbed by means of water and/or aqueous solution, as described by way of example in WO 2004/035514 and DE-A 10243625. The crude acrylic acid withdrawn is subsequently preferably subjected to a suspension crystallization and the acrylic acid suspension crystals which are formed are preferably removed from remaining mother liquor by means of a wash column. Advantageously, the wash liquid used is the melt of acrylic acid crystals which have been removed beforehand in the wash column. Furthermore, the wash column is preferably one having forced transport of the crystal bed. It is more preferably a hydraulic or a mechanical wash column. For specific details, the description of WO 01/77056, WO 03/041832 and WO 03/041833 may be followed. In other words, preference is given to recycling mother liquor which remains into the fractional condensation (cf. also EP-A 1015410). The secondary component discharge is normally below the side draw of the crude acrylic acid as a purge stream. Using only one crystallization stage, it is thus possible to obtain acrylic acid having a purity of ≧99.8% by weight which is outstandingly suitable for producing superabsorbents based on poly-Na acrylate.

Examples (all pressures, as always in this document, are absolute pressures unless explicitly mentioned otherwise)

A) Configuration of Reaction Stage I (of the Dehydrogenation Stage)

The dehydrogenation stage consisted of three identical tubular reactors which were connected in series and charged in an identical manner with dehydrogenation catalyst.

The individual tubular reactor was a steel tube (stainless steel of DIN materials no. 1.4841) of length 1300 mm, wall thickness 3.6 mm and internal diameter 53.1 mm. The tubular reactors were each flowed through by reaction gas mixture 1 from top to bottom.

At the lower end of each tubular reactor was disposed a support grating made of the same stainless steel. On the support grating was disposed, from bottom to top, the following charge:

| | |
|---|---|
| 175 mm | bed length of steatite spheres (diameter 4-5 mm) of Steatite C-220 from CeramTec; |
| 21 mm | bed length of steatite spheres (diameter 1.5-2.5 mm) of Steatite C-220 from CeramTec; |
| 210 mm | bed length of dehydrogenation catalyst (Pt/Sn alloy which had been promoted with the elements Cs, K and La in oxidic form and which had been applied to the outer and inner surface of $ZrO_2 \cdot SiO_2$ mixed oxide support extrudates (average length (having a Gaussian distribution in the range from 3 mm to 12 mm with a maximum at approx. 6 mm): 6 mm, diameter: 2 mm) in the elemental stoichiometry (mass ratios including support) $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in example 4 of DE-A 10 219 879). |
| 21 mm | bed length of steatite spheres (diameter 1.5-2.5 mm) of Steatite C-220 from CeramTec; and finally, the remaining length of the tubular reactor, again a bed of steatite spheres (diameter 4-5 mm) of Steatite C-220 from CeramTec. |

The exterior of each of the tubular reactors was inserted, for the purposes of a preheating zone, for the first 500 mm of tube length from top to bottom (toward the support grating) into two half-shells made of copper (coating thickness=200 mm) which ensure uniform distribution of the amount of heat supplied and were electrically heated by means of a heating sleeve (from Horst, Heidelberg, Germany, length 500 mm, internal diameter 100 mm) which fully surrounded them.

From bottom to top, each of the tubular reactors, for the purposes of an adiabatic zone, was inserted for a length of 600 mm into in each case two pairs of thermally insulating half-shells (thickness of one half-shell=25 mm) made of MPS-Super G from Microtherm in Germany, which were mounted one on top of the other offset by 90° from one another. The insulating half-shells were in turn surrounded by a cylindrical envelope made of stainless steel (external diameter=173 mm, internal diameter=167 mm), to which was applied, for the purpose of trace heating, a heating sleeve (length=675 mm, internal diameter=173 mm) from Horst, Heidelberg, Germany. In this manner, it was possible in the adiabatic zone to minimize the heat flux from the environment into the reaction tube and out of the reaction tube into the environment.

Into each reaction tube was additionally inserted centrally a 1370 mm-long thermowell (external diameter: 6 mm, internal diameter: 4 mm), into which a multithermoelement (a total of 10 measurement points every 4 cm from the lower end of the reactor upward, thickness 3.2 mm) had been inserted.

Upstream of each individual tubular reactor was connected a steel tube, filled with steatite rings (made of Steatite C-220 from CeramTec and of geometry 7 mm×3 mm×3 mm=external diameter×internal diameter×height), of length 1300 mm as a heater. In this tube, reaction gas mixture 1 was in each case preheated to the entrance temperature of the downstream tubular reactor and simultaneously mixed in an ideal manner. For this purpose, the heater tubes (stainless steel of DIN materials no. 1.4841, wall thickness 3.6 mm, internal diameter 53.1 mm) were electrically heated along the central 1200 mm length of the tube by means of heating sleeves from Horst, Heidelberg, Germany applied to them. The connection between heaters and tubular reactors was brought about by stainless steel tubes (stainless steel of DIN materials no. 1.4841, external diameter 21.3 mm, internal diameter 16.1 mm, length approx. 700 mm) thermally insulated with customary heat insulation materials.

Upstream of the inlet of the reaction gas mixture 1 into the particular heater was mounted a feed tap, through which compressed air could in each case be supplied to the reaction gas mixture 1. The steady state is described hereinbelow.

To the first dehydrogenation reactor was fed a starting reaction gas mixture 1 composed of 300 g/h of crude propane (first feed stream comprising propane), 375 g/h of water and 3768 g/h of overall $C_3$ cycle gas (second feed stream comprising (unconverted) propane (and unconverted propylene)) at a temperature of 400° C. and an absolute pressure of 2.6 bar (on the industrial scale, the inlet pressure was appropriately selected approx. 0.5 bar higher, in order to take account of the increased pressure drop in reaction stage 1 (caused by higher flow rates)).

The crude propane comprised:

| | % by vol. |
|---|---|
| methane | 0 |
| ethane | 0.156 |
| ethene | 0 |
| propane | 96.18 |
| propene (propylene) | 0.002 |
| $H_2$ | 0 |
| $O_2$ | 0 |
| $N_2$ | 1.70 |
| CO | 0 |
| $CO_2$ | 0 |
| isobutane | 1.245 |
| n-butane | 0.711 |
| trans-butene | 0.0005 |
| isobutene | 0 |
| cis-butene | 0.0015 |
| 1-butene | 0.0048 |
| butadiene | 0 |

The overall $C_3$ cycle gas comprised:

| | % by vol. |
|---|---|
| Methane | 0.009 |
| Ethane | 0.088 |
| Ethene | 0.038 |
| Propane | 29.56 |
| Propene | 0.122 |

-continued

| | % by vol. |
|---|---|
| $H_2$ | 0.050 |
| $O_2$ | 3.35 |
| $N_2$ | 64.05 |
| CO | 0.538 |
| $CO_2$ | 1.85 |
| Isobutane | 0.234 |
| n-butane | 0.098 |
| trans-butene | 0.00005 |
| Isobutene | 0.00051 |
| cis-butene | 0.00144 |
| 1-butene | 0.00048 |
| Butadiene | 0.0087 |

The composition of the crude propane and all other gas compositions were determined by gas chromatography [HP 6890 with Chem-Station, detectors: FID, TCD, separating columns: $Al_2O_3$/KCL (Chrompak), Carboxen 1010 (Supelco)]. In the case of gas mixtures comprising steam, the steam was condensed out in a water separator by cooling and, if appropriate, decompression before the gas chromatography analysis. The uncondensed residual gas was analyzed and all data relate to this gas on a dry basis (i.e. the amount of steam present in the gas mixture which was actually to be analyzed was not taken into account).

Starting reaction gas mixture 1 was generated in an evaporator which was connected upstream of the first heater. The evaporator itself was likewise designed as a heater. To it were fed 300 g/h of gaseous crude propane (65° C., 5 bar), 3768 g/h of overall $C_3$ cycle gas (50° C., 2.8 bar) and 375 g/h of water (20° C., 3 bar). The heating of the evaporator was controlled to a gas mixture outlet temperature of 200° C. The evaporator was connected to the first heater in a manner corresponding to that in which the reactors were connected to the heaters.

The heating of the first heater was controlled in such a way that the gas mixture passed from the evaporator into the first heater left the first heater at a temperature of 400° C. (the wall temperature required for this purpose was approx. 440° C.). Starting reaction gas mixture 1 was then conducted into the first tubular reactor and heated further in the preheating zone thereof to a reaction zone inlet temperature of 460° C.

When it passed through the first tubular reactor, the temperature of reaction gas mixture 1 passed through a maximum (known as hotspot temperature) of 549.1° C. (the quantitative data reported here relate to the operating state after 200 operating hours; in the further course of operation, the different temperatures were adjusted such that the conversion based on single pass and the space-time yield remained substantially constant; the corresponding procedure was also used in the first 200 operating hours), which migrated in flow direction in the course of the continuous operation of the experimental plant owing to gradual catalyst deactivation (the migration rate was approx. 0.03 mm/h).

The reaction gas mixture 1 leaving the first dehydrogenation reactor had the following contents:

| | % by vol. |
|---|---|
| methane | 0.045 |
| ethane | 0.109 |
| ethene | 0.042 |
| propane | 30.3 |
| propene | 2.88 |
| $H_2$ | 5.00 |
| $O_2$ | 0 |
| $N_2$ | 59.13 |
| CO | 0.06 |
| $CO_2$ | 3.24 |
| isobutane | 0.257 |
| n-butane | 0.116 |
| trans-butene | 0.05 |
| isobutene | 0.001 |
| cis-butene | 0.004 |
| 1-butene | 0.001 |
| butadiene | 0.003 |

Its temperature was 509° C. and its pressure was approx. 2.56 bar.

Before it entered the downstream heater, 80 l (STP)/h of compressed air were metered to reaction gas mixture 1 (23° C., 4.2 bar).

Reaction gas mixture 1 was then heated to 465° C. (2nd reaction zone inlet) by means of the electrical heating means of the heater (wall temperature approx. 540° C.) and the preheating zone of the downstream (second) reaction tube (wall temperature approx. 560° C.). The pressure of reaction gas mixture 1 at this point was 2.56 bar.

When it passed through the second tubular reactor, the temperature of reaction gas mixture 1 passed through a maximum of approx. 560° C. which migrated in flow direction in the course of the continuous operation of the experimental plant owing to gradual catalyst deactivation (the migration rate was approx. 0.1 mm/h). The reaction gas mixture 1 leaving the second dehydrogenation reactor had the following contents:

| | % by vol. |
|---|---|
| methane | 0.078 |
| ethane | 0.144 |
| ethene | 0.063 |
| propane | 26.6 |
| propene | 4.94 |
| $H_2$ | 6.43 |
| $O_2$ | 0 |
| $N_2$ | 58.58 |
| CO | 0.384 |
| $CO_2$ | 3.58 |
| isobutane | 0.22 |
| n-butane | 0.094 |
| trans-butene | 0.063 |
| isobutene | 0.001 |
| cis-butene | 0.01 |
| 1-butene | 0 |
| butadiene | 0.004 |

Its temperature was approx. 493° C. and its pressure was approx. 2.52 bar.

Before it entered the downstream heater, 98 l (STP)/h of compressed air were metered to reaction gas mixture 1 (23° C., 4.2 bar).

Reaction gas mixture 1 was then heated to 521° C. (3rd reaction zone inlet) by means of the electrical heating means of the heater (wall temperature approx. 540° C.) and the preheating zone of the downstream (third) reaction tube (wall temperature approx. 540° C.). The pressure of reaction gas mixture 1 at this point was 2.52 bar.

When it passed through the third tubular reactor, the temperature of reaction gas mixture 1 passed through a maximum of 570° C. which migrated in flow direction in the course of the continuous operation of the experimental plant owing to gradual catalyst deactivation (the migration rate was approx. 0.1 mm/h). The reaction gas mixture 1 leaving the third dehydrogenation reactor had the following contents:

|  | % by vol. |
| --- | --- |
| methane | 0.1046 |
| ethane | 0.144 |
| ethene | 0.0743 |
| propane | 25.22 |
| propene | 5.51 |
| $H_2$ | 4.69 |
| $O_2$ | 0 |
| $N_2$ | 60.10 |
| CO | 0.237 |
| $CO_2$ | 3.54 |
| isobutane | 0.201 |
| n-butane | 0.085 |
| trans-butene | 0.070 |
| isobutene | 0.0013 |
| cis-butene | 0.011 |
| 1-butene | 0.0004 |
| butadiene | 0.0056 |

Its temperature was 480.4° C. and its pressure was 2.48 bar.

This resulted in an overall dehydrogenation conversion of the propane over the dehydrogenation stage (reaction stage 1), based on single pass of starting reaction gas mixture 1, of 19.91 mol %.

In the event of advanced deactivation of the dehydrogenation catalyst beds, the process was interrupted and they were regenerated as described in DE-A 10028582. This was essentially always the case when the hotspot temperature in all three tubular reactors was approx. 580° C.

Surprisingly, the deactivation of the dehydrogenation catalyst beds progressed more slowly at elevated working pressure.

B) Configuration of the Secondary Component Discharge

Direct cooling with sprayed cooled water (T=20° C.) cooled the product gas mixture 1 leaving the third dehydrogenation reactor to 40° C. in a direct cooler (quench) in cocurrent (the remaining gaseous mixture was conducted out of the water quench in the opposite direction to the product gas inflow direction). About 75% by weight of the steam present in product gas mixture 1 (steam was added to starting reaction gas mixture 1 and formed in the dehydrogenation stage as a result of combustion of hydrogen and also possibly hydrocarbon with atmospheric oxygen; the heat of combustion substantially maintained the reaction temperature in reaction gas mixture 1 in reaction stage 1) condensed out in the course of direct cooling. The condensate which formed was conducted out of the water quench by means of level control and sent to its disposal. Otherwise, the water used for direct cooling was circulated (by pumping), recooled by indirect heat exchange and sprayed again for the purpose of direct cooling.

Instead of the direct cooling with water described, the product gas mixture 1 from the dehydrogenation stage may also initially be cooled by heating the starting reaction gas mixture 1 to be fed to the dehydrogenation stage (for example to a temperature in the range from 350° C. to 450° C.) with product gas mixture 1 in an indirect heat exchanger (for example in a tube bundle heat exchanger in cocurrent or in countercurrent). This cools the product gas mixture 1 of the dehydrogenation stage to an appropriate degree from the high exit temperature of the dehydrogenation stage (for example from 450 to 550° C.) to from approx. 200 to 300° C.

A further cooling of the product gas mixture 1 of the dehydrogenation stage can be effected by using it in an indirect heat exchanger for the purpose of heating the starting reaction gas mixture 2 for the partial oxidation, still to be described hereinbelow, of the propene generated in the dehydrogenation stage, and/or by using it for the purpose of balancing the absorber offgas cooling, still to be described below, in the preferably two-stage expansion thereof by means of expansion turbines, or for the purpose of compensating for it by advance incipient heating.

Afterward, product gas mixture 1 is at a temperature of about 180° C. Subsequently, it is possible to cool it to a temperature in the range from 30° C. to 60° C. by means of air and/or surface water coolers.

Droplet separators integrated into the coolers or connected downstream thereof collect the water which has condensed out in the course of cooling and feed it to disposal under level control.

The thus cooled and steam-deburdened product gas mixture 1 of the dehydrogenation stage, having a pressure of about 2 bar, was subsequently compressed to a pressure of from 10 to 13 bar.

In an appropriate manner from an application point of view, the compression was carried out in two stages in order to avoid excessively high compression temperatures (this purpose was also served by the cooling carried out in advance; the steam separation additionally deburdens the compressor output to be expended). In the first stage, compression was effected to a pressure of from 4 to 4.5 bar. The outlet temperature of the gas mixture on leaving the compressor was about 115° C.

In a downstream indirect heat exchanger (air cooler or surface water cooler), the gas mixture was cooled again to from 40 to 60° C., in the course of which further steam condensed. Droplet separators collected the condensate and discharged it under level control.

In the second compressor stage, compression was effected starting from a pressure of about 4 bar to an end pressure of 10 bar (here, it is also possible if appropriate to condense to a pressure of up to 13 bar and more). The outlet temperature on leaving the compressor was about 126° C.

In two further downstream indirect heat exchangers (initially an air cooler (is normally a tube bundle heat exchanger; the gas to be cooled appropriately flows through the tube interior) and then a surface water cooler), the compressed gas mixture was cooled initially to from 40 to 60° C. and then to 30° C. Water which condensed out was again separated by means of droplet separators and conducted out. When it leaves the second compressor, the gas mixture only comprises approximately 0.2% by weight of water. The low water content reduces the occurrence of water and thus prevents operation problems, caused by biphasicity of the liquid, in the downstream absorption, and the high pressure reduces the amount of absorbent required for the purpose of absorption.

While turbocompressors (non-oil-lubricated, dry-running, contactless compressors) are used on the industrial scale for the purpose of compression (for example of the 12 MH 4B type from Mannesmann DEMAG, Germany), MV 3459 II membrane compressors from Sera were used here. In principle, the compressors may be driven either by electric motors or by vapor or gas turbines. Frequently, driving by vapor turbines is the most economic. The gas mixture, cooled and compressed as described, was fed to an absorption column directly above the bottom (approx. 4650 g/h). It had the following contents:

|  | % by vol. |
|---|---|
| nitrogen | 61.22 |
| oxygen | 0.25 |
| propane | 24.23 |
| propene | 5.07 |
| methane | 0.02 |
| ethane | 0.11 |
| ethene | 0.03 |
| n-butane | 0.06 |
| isobutane | 0.09 |
| n-butenes | 0.04 |
| isobutene | 0.10 |
| 1,3-butadiene | 0.00 |
| hydrogen | 5.57 |
| carbon monoxide | 0.05 |
| carbon dioxide | 3.15 |

The absorption column consisted of 1.4571 stainless steel. The column internal diameter was 80 mm, the wall thickness 4 mm and the column length 1.70 m.

About 70% of the volume of the absorption column was filled with Montz packing elements (Montz BSH-750, specific surface area 750 m$^2$/m$^3$) as separating internals. The packing elements were directly adjacent to one another and began at the height of ⅕ of the column length from below. The absorption column was neither cooled nor heated externally. At the top of the column, technical-grade tetradecane from Haltermann, Germany, of the PKWF 4/7 af type was introduced at an introduction temperature of 30° C. as an absorbent (gas chromatography analysis by means of FID detection gave the following GC area % composition at the start (fresh):
n-tridecane 7.6%,
n-tetradecane 47.3%,
n-pentadecane 7.0%,
n-hexadecane 3.2%,
n-heptadecane 14.1% and
residual sum 20.7%;
this composition changed in the course (after approx. 3000 h$^{-1}$) of continuous process operation to the following values:
n-tridecane 2.6%,
n-tetradecane 39.5%,
n-pentadecane 9.4%,
n-hexadecane 4.8%,
n-heptadecane 23.4% and
residual sum 20.3%).

The trickle density was 15 m$^3$ of absorbent per m$^2$ of free cross-sectional area and hour (=28 kg/h of tetradecane).

The offgas stream conducted out of the absorption column as a secondary component discharge to combustion still comprised 950 ppm by volume of propane and 250 ppm by volume of propene. On the industrial scale, this offgas stream is conducted via an expander (for example an expansion turbine) into the combustion, in order to recover the majority of the compression output expended in the two-stage compression and to recycle it into the two-stage compression. Appropriately, the expansion is also carried out in two stages in order to prevent undesired condensation. The mechanical energy obtained in the decompression may be utilized either directly as a secondary or main drive for one of the compressors and/or to generate electricity.

Before the decompressed absorber offgas is conducted to the combustion, it may be appropriate on the industrial scale to remove the hydrogen present therein. This may be effected, for example, by passing the offgas through a membrane, generally shaped to a tube, which is permeable only to the molecular hydrogen. The thus removed molecular hydrogen may be recycled, for example, into the heterogeneously catalyzed dehydrogenation or fed to another utilization (for example in fuel cells).

In principle, the hydrogen removal may also be undertaken by partial condensation, adsorption (pressure swing adsorption) and/or rectification (preferably under pressure). On the industrial scale, it is additionally generally appropriate to conduct the absorber offgas through the acid water, yet to be described below, in order to concentrate it.

The absorbate comprised the following contents (% by weight based on the weight of the absorbate):

|  | % by weight |
|---|---|
| nitrogen | 0.147 |
| propane | 4.58 |
| propene | 0.915 |
| ethane | 0.07 |
| n-butane | 0.015 |
| isobutane | 0.023 |
| n-butenes | 0.009 |
| isobutene | 0.024 |
| carbon dioxide | 0.086 |
| ethene | 0.000 |
| tetradecane | approx. remainder up to 100% by weight |

Before the absorbate was conducted to the top of the downstream desorption column, it was heated to 60° C. in an indirect heat exchanger.

Subsequently, the absorbate (this may be performed, for example, in an inverse pump or by means of a valve) was decompressed to a pressure of 2.7 bar (the mechanical energy released in the case of the inverse pump is appropriately also used to recompress absorbent freed in the desorption column) and the biphasic mixture thus generated was conducted into the desorption column at the top.

Air was conducted at a pressure of 3 bar into the desorption column (internal diameter=80 mm, length=1.70 m, wall thickness=4 mm) from the bottom in countercurrent to the absorbate descending from the desorption column head (1269 l (STP)/h). The amount of absorbate introduced at the top was 33.7 l/h. The absorbent which had been conducted out of the desorption column at the bottom and had been substantially freed of desorbed components was cooled by indirect heat exchange with absorbate, compressed to the pressure required in the absorption column, cooled to 16° C. by another indirect heat exchange (on the industrial scale appropriately with surface water) and then recycled to the top of the absorption column. As separating internals, the desorption column comprised structured sheet metal packings from Montz (Montz BSH-750, specific surface area 750 m$^2$/m$^3$). In order to retain absorbent, the gas stream conducted out of the desorption column (if appropriate through a mechanical droplet separator) was washed with water. In other words, it was conducted through a packing element from Montz (Montz BSH-750, specific surface area 750 m$^2$/m$^3$), to which water (70 l/h) was introduced in countercurrent at a temperature of 18° C. Below the packing was mounted a collecting tray (chimney tray), from which the aqueous phase could be conducted out. In a phase separator, separation was effected into an aqueous phase and into an organic phase. The very small amount of organic phase was combined with the absorbent stream recycled to the top of the absorption column. The aqueous phase was recooled and introduced back to the packing element supplemented with fresh water (in order to compensate for evaporation losses). The washing was effected attached to the desorption column.

From the wash section, the washed gas stream was conducted out through mechanical droplet separators (separated liquid phase is recycled into the wash) with the following contents (when the dehydrogenation conversion selected in reaction stage 1 is higher, the subsequent propene content may also be from 8 to 12% by volume; for example, the washed gas stream may also have 15% by volume of propane, 10% by volume of propene and 14.5% by volume of $O_2$):

|  | % by vol. |
|---|---|
| nitrogen | 46.69 |
| oxygen | 11.84 |
| propane | 32.53 |
| propene | 6.81 |
| ethane | 0.07 |
| n-butane | 0.08 |
| isobutane | 0.12 |
| n-butenes | 0.05 |

-continued

|  | % by vol. |
|---|---|
| isobutene | 0.13 |
| hydrogen | 0.07 |
| carbon monoxide | 0.00 |
| carbon dioxide | 0.61 |
| water | 1.00 |
| ethene | 0.00 |

The temperature of the gas mixture was increased to 250° C. by indirect heat exchange and the gas mixture with the aforementioned composition was conducted in an amount of 2128 l (STP)/l·h and an inlet pressure of 2.1 bar as a new starting reaction gas mixture 2 into the downstream partial oxidation apparatus.

C) Configuration of the Second and of the Third Reaction Stage (the Partial Oxidation)

1. First Fixed Bed Reactor for the Step of Partial Oxidation of Propene (Propylene) to Acrolein

| | |
|---|---|
| Heat exchange medium used: | salt melt consisting of 53% by weight of potassium nitrate, 40% by weight of sodium nitrite and 7% by weight of sodium nitrate. |
| Dimension of the catalyst tube: | total length 4200 mm, internal diameter 26 mm, external diameter 30 mm, wall thickness 2 mm. |
| Reactor: | Consisted of a jacketed cylinder made of stainless steel (cylindrical guide tube surrounded by a cylindrical outer vessel). The wall thicknesses were universally from 2 to 5 mm. The internal diameter of the outer cylinder was 168 mm. The internal diameter of the guide tube was approx. 60 mm. At the top and bottom, the jacketed cylinder was concluded by a lid and bottom respectively. The catalyst tube was mounted, guided by the cylindrical guide tube, in the cylindrical vessel such that it projected at the top and bottom end thereof (with sealing) through the lid and bottom respectively in each case by 250 mm. The heat exchange medium was enclosed in the cylindrical vessel. In order to ensure very uniform thermal boundary conditions at the outer wall of the catalyst tube over the entire catalyst tube length within the cylindrical vessel (3700 mm), the heat exchange medium was circulated by sparging of nitrogen in the cylindrical vessel. By means of the rising nitrogen, the heat exchange medium was conveyed from bottom to top in the cylindrical guide tube in order then to flow back downward in the intermediate space between cylindrical guide tube and cylindrical outer vessel (circulation of equal goodness can also be achieved by pumped circulation (for example propeller pumps)). Electrical heating mounted on the outer jacket might control the temperature of the heat exchange medium to the desired level. Otherwise, there was air cooling. |
| Reactor charge: | Viewed over the reactor, salt melt and reaction gas mixture 2 were conducted in countercurrent. Reaction gas mixture 2 entered the reactor at the top. It was conducted into each reaction tube at a temperature of 250° C. The salt melt entered the cylindrical guide tube at the bottom at a temperature $T^{in} = 335°$ C. and left the cylindrical guide tube at the top at a temperature $T^{out}$. The difference between $T^{in}$ and $T^{out}$ was about 2° C. $T^{average} = (T^{in} + T^{out})/2$. |
| Catalyst tube charge: (from top to bottom) | Section A: length 50 cm Preliminary bed of steatite rings (Steatite C 220 from CeramTec) of geometry 7 mm × 7 mm × 4 mm (external diameter × length × internal diameter). Section B: length 100 cm Catalyst tube charge with a homogeneous mixture of 20% by weight (alternatively 30% by weight) of steatite rings (Steatite C 220 from CeramTec) of geometry 5 mm × 3 mm × 2 mm (external diameter × length × internal diameter) and 80% by weight (alternatively 70% by weight) of unsupported catalyst from section C. Section C: length 170 cm Catalyst charge of annular (5 mm × 3 mm × 2 mm = external diameter × length × internal diameter) unsupported | catalyst according to example 1 of DE-A 10046957.
Section D: length 50 cm
Downstream bed of steatite rings (Steatite C 220 from CeramTec) of geometry 7 mm × 7 mm × 4 mm (external diameter × length × internal diameter).

2. Intermediate Cooling and Intermediate Oxygen Feeding

The product gas mixture 2 leaving the first fixed bed reactor was conducted for the purpose of intermediate cooling (indirectly by means of air) through a connecting tube (length=400 mm, internal diameter=26 mm, wall thickness=2 mm, material=stainless steel) which, mounted centrally for a length of 200 mm, was charged with an inert bed of steatite spheres (Steatite from CeramTec) of diameter from 5 to 6 mm and flanged directly onto the catalyst tube of the first fixed bed reactor.

The gas mixture entered the connecting tube at a temperature of more than 310° C. and left it at a temperature of about 140° C. Subsequently, 269 l (STP)/h of compressed air as an oxygen source were mixed with the gas mixture.

The resulting charge gas mixture mixed on a static mixer was fed at a temperature of 220° C. to the fixed bed reactor for the step of partial oxidation of acrolein to acrylic acid.

3. Second Fixed Bed Reactor for the Step of Partial Oxidation of Acrolein to Acrylic Acid A fixed bed reactor was used which was of identical design to that for the first step. Salt melt and reaction gas mixture were conducted in cocurrent viewed over the reactor. The salt melt entered at the bottom, the reaction gas mixture likewise.

The catalyst tube charge (from bottom to top) was:
Section A: length 20 cm
Preliminary bed of steatite rings (Steatite C 220 from CeramTec) of geometry 7 mm×7 mm×4 mm (external diameter×length×internal diameter).
Section B: length 100 cm
Catalyst charge of a heterogeneous mixture of 20% by weight (alternatively 30% by weight) of steatite rings (Steatite C 220 from CeramTec) of geometry 7 mm×3 mm×4 mm (external diameter×length×internal diameter) and 80% by weight (alternatively 70% by weight) of coated catalyst from section C.
Section C: length 200 cm
Catalyst charge of annular (7 mm×3 mm×4 mm=external diameter×length×internal diameter) coated catalyst according to preparation example 5 of DE-A 10046928 (at this point, it is also possible to use analogous coated catalysts and those prepared in a corresponding manner, but whose active composition has a stoichiometry of $Mo_{12}V_{2.8}W_{1.2}Cu_{2.4}O_x$ or $Mo_{12}V_{3.5}W_{1.3}Cu_{2.4}O_x$).
Section D: length 50 cm
Downstream bed of steatite rings (Steatite C 220 from CeramTec) of geometry 7 mm×7 mm×4 mm (external diameter×length×internal diameter).

The second reactor was charged with approx. 3607 g/h of charge gas mixture (starting reaction gas mixture 3). $T^{average}$ is as defined for the reactor of the second stage and was 284° C.

The propene conversion in the first reaction stage was 98.0 mol % and the acrolein conversion in the second reaction stage was 99.8 mol %.

The contents of the product gas mixture 3 leaving the second fixed bed reactor at a temperature of 281° C. and a pressure of 1.8 bar were:

| | % by vol. |
|---|---|
| nitrogen | 51.54 |
| oxygen | 2.3 |
| propane | 29.20 |
| propene | 0.110 |
| methane | 0 |
| ethane | 0.077 |
| n-butane | 0.101 |
| isobutane | 0.236 |
| n-butenes | 0 |
| isobutene | 0.001 |
| 1,3-butadiene | 0.009 |
| hydrogen | 0.05 |
| carbon monoxide | 0.596 |
| carbon dioxide | 1.72 |
| water | 8.21 |
| acrolein | 0.009 |
| acrylic acid | 5.28 |
| acetic acid | 0.240 |
| propionic acid | 0.002 |
| formic acid | 0.019 |
| formaldehyde | 0.198 |
| benzaldehyde | 0.005 |
| maleic anhydride | 0.047 |
| methacrolein | 0.020 |
| methacrylic acid | 0.011 |
| ethene | 0.032 |

The catalysts used in the two reaction stages 2,3 may also be replaced by the catalysts used in the examples of DE-A 10351269. The catalyst of the second reaction stage may also be replaced by the catalysts of the examples and comparative examples of DE-A 10344149. The catalyst of the third reaction stage may also be replaced by the catalysts of the examples of DE-A 10360057 and DE-A 10360058. In addition, the partial oxidation may be carried out as a high-load method, as described in DE-A 10313210, DE-A 10313213, DE-A 10313212, DE-A 10313211, DE-A 10313208, DE-A 10313209 and DE-A 10313214, and the prior art acknowledged in these documents.

D) Configuration of Separation Zone A (Removal of the Acrylic Acid Target Product from the Product Gas Mixture 3 of the Partial Oxidation)

In a direct cooler, the hot product gas mixture stream (product gas mixture 3) was cooled to approx. 180° C. in cocurrent (after combination with the laden stripping gas stream described below) by spraying in a quench liquid (comprising 57.4% by weight of diphenyl ether, 20.7% by weight of diphenyl, 20% by weight of dimethyl o-phthalate and, as the remainder of up to 100% by weight, phenothiazine (up to 1% by weight) and high boilers (e.g. acrylic acid oligomers)) of temperature from 140 to 150° C., which was also used as the absorbent. In the lower section of the direct cooler, the unevaporated quench liquid was collected, withdrawn and, via a heat exchanger in which it was brought back to input temperature, resprayed into the upper section of the quench vessel. The product gas mixture stream 3 (combined with the laden stripping gas) and the quench liquid which has been sprayed to give jets were fed in parallel to the direct cooler. The cooled product gas mixture stream 3 then flowed into the downstream absorption column. In the quench circuit, high-boiling by-products then accumulated and had to be discharged. From the quench circuit, a portion of 1 kg of quench liquid was therefore discharged discontinuously once per day into a vessel which was worked up discontinuously with the aid of a rotary evaporator (8 mbar, 180° C.). The purified absorbent condensate obtained in this way was fed to the buffer vessel described below for the bottom effluent from the residual gas stainless steel pressure wash column, and the losses of absorbent of about 2.9 g/h which were suffered in the course of workup in the rotary evaporator were replaced once per week by addition of fresh mixture consisting of diphenyl ether (21.2% by weight), diphenyl (58.8% by weight) and dimethyl ophthalate (20% by weight) to the condensate.

The cooled product gas mixture 3 was conducted into the absorption column above the bottom and below the first packing element. The absorption column (without the bottom) was 5420 mm long, had an internal diameter of 50 mm and contained Kuehni (CH) Rhombopak 9M packings for a total length of 3.3 m.

The absorption column was manufactured from glass and, for reasons of heating, had a segmented glass jacket. Immediately above the second packing element, viewed from below, was installed a pressure decoupling valve (an adjustable throttle), with the aid of which a pressure drop over the absorption column (as would occur on the industrial scale) of from 100 to 300 mbar could be simulated. The absorption column was operated at a top pressure of 1.30 bar and a bottom pressure of 1.40 bar. The bottom temperature was approx. 113° C. The glass jacket was divided into five successive, separately operated segments which were used to impose the temperature profile below on the absorption column. This segmentation was also followed by the inner structure of the absorption column.

The segments had, from bottom to top, the following temperatures (they were each thermostatted by means of water pumped in circulation, or with heat carrier oil of corresponding temperature in the 1st segment) and were configured as follows:

1st segment: length 1020 mm (upward starting from the feed point of product gas mixture 3), 113° C., 0.4 m of Rhombopak between the feed point of product gas mixture 3 disposed directly above the bottom of the absorption column and the feed point of bottoms liquid which is continuously withdrawn from the column bottom and recirculated into the column (at approx. 113° C., in an amount of approx. 200 l/h) and 0.6 m of Rhombopak above this introduction point. The distance between the two Rhombopaks was approx. 2 cm.

2nd segment: length 1250 mm, 75° C., at the lower end was disposed the pressure decoupling valve and above the pressure decoupling valve up to the feed point of the low boiler condensate stream from the purifying distillation described below was disposed 0.5 m of Rhombopak.

3rd segment: length 950 mm, 60° C., 0.6 m of Rhombopak which begins directly above the low boiler condensate introduction point of the 2nd segment.

4th segment: length 950 mm, 50-55° C., 0.6 m of Rhombopak which ends directly below the introduction point of the main absorbent stream described below.

5th segment: length 1250 mm, 20° C., 0.6 m of Rhombopak between the collecting tray mounted directly above the absorbent introduction in the 4th segment for the efflux of the acid water (described below) and the introduction point of recirculated acid water at the top of the absorption column.

From the aforementioned collecting tray disposed in the 5th segment, water-rich condensate (acid water) was drawn off continuously (approx. 70.2 l/h). It was cooled indirectly to 20° C. using a heat exchanger and recycled back into the absorption column predominantly above the uppermost Rhombopak packing (70 liters/h). The nonrecycled proportion of the acid water withdrawn (the reaction water) was discharged under level control and sent to an acid water extraction stage. In this stage, the discharged acid water was combined and mixed at ambient pressure with the smaller substream of the absorbent (described below) having a low loading (of acrylic acid and secondary components) in a stirred glass vessel kept at ambient temperature (volume 1 liter, diameter 80 mm). The resulting mixture was discharged continuously into a glass phase separation vessel (volume 7.5 liters, diameter 150 mm) likewise kept at ambient temperature by free overflow. There, the liquid mixture which had overflowed was separated into two liquid phases, short-chain acidic secondary components (for example acetic acid) being transferred preferentially into the aqueous phase having lower specific gravity and acrylic acid preferentially into the organic phase having higher specific gravity. The organic phase is combined with the larger substream of the absorbent having a low loading by means of a forced-conveyance membrane metering pump and this overall stream (approx. 3.0 l/h, 40° C.) was fed as already described directly below the acid water collecting tray as the main absorbent stream to the absorption column.

The (main) residual gas leaving the absorption column at the top (T=20° C., P=1.30 bar) had the following contents:

|  | % by volume |
|---|---|
| nitrogen | 59.9 |
| oxygen | 2.67 |
| propane | 33.93 |
| propene | 0.128 |
| methane | 0 |
| ethane | 0.09 |
| n-butane | 0.118 |
| isobutane | 0.274 |
| n-butenes | 0 |
| isobutene | 0.001 |
| butadienes | 0.010 |
| hydrogen | 0.058 |
| carbon monoxide | 0.693 |
| carbon dioxide | 1.97 |
| acrolein | 0.009 |
| ethene | 0.037 |
| all contents above are calculated without water | |
| water | 1.78 |
| | (based on all) |

The (main) residual gas was heated to 40° C. by indirect heat exchange (in order to rule out undesired condensation), compressed to 2.70 bar by means of a membrane compressor (on the industrial scale, a turbocompressor driven by means of electric motor, for example of the 12MH4B type from Mannesmann DEMAG, Germany) and about 78% by volume were recycled as main $C_3$ cycle gas into reaction stage 1 to charge the first dehydrogenation reactor.

About 22% by volume of the compressed (main) residual gas were branched off with decompression to 1.6 bar and washed in a stainless steel pressure wash column (material 1.4571, internal diameter 30 mm, charge: 2 m of Rhombopak 9M) in countercurrent at approx. 1.6 bar and approx. 51° C. with the total stream, described below, of absorbent having very low loading (the absorbent having very low loading was introduced at the top and the gas was conducted into the column at the bottom).

In a further stainless steel pressure column (material 1.4571, internal diameter 30 mm, charge: 3 m of Rhombopak 9M, jacket heated with oil=stripping column), this washed gas stream at approx. 1.5 bar and from approx. 119 to 125° C. was utilized in order to strip low-boiling components out of the laden absorbent stream which was drawn off continuously from the bottom of the absorption column (approx. 3.5 l/h, approx. 113° C.) (for example as described in DE-A 10336386). The resulting gas stream (laden stripping gas) laden with low boilers (more volatile than acrylic acid) was heated in a jacketed line (diameter 15 mm, outer jacket: corrugated stainless steel tube) heated at 170° C. and combined with the hot product gas mixture stream 3 at the inlet of the quench vessel.

At the lower end of the stainless steel pressure wash column, the absorbent stream with a low loading was discharged under level control into the buffer vessel already mentioned (glass, volume 5 liters) (the absorbent condensate obtained in the rotary evaporator is also passed into this vessel as already described).

From the buffer vessel, a larger substream of 2.5 l/h of absorbent having low loading was conducted by means of a membrane pump to the absorption column and introduced there as already described as a constituent of the main absorbent stream directly below the collecting tray for the acid water discharge in segment 4. The smaller substream of 460 ml/h of absorbent having low loading was, as likewise already described, passed by means of a further membrane pump into the stirred glass vessel of the acid water extraction stage.

From the bottoms circulation system (approx. 100 l/h, compressed air membrane pump) of the stripping column, approx. 3.5 kg of bottoms liquid were drawn off under level control through a stainless steel fabric filter and a regulating valve and fed to the vacuum distillation unit for the purpose of purifying distillation.

The vacuum distillation unit consisted of a metallized and vacuum-insulated glass column (purifying column) with internal diameter 50 mm and length 4000 mm. By means of forced-evaporation bottoms circulation (approx. 250 l/h, peripheral wheel centrifugal pump), a bottom temperature of 191° C. was maintained (p=4 bar). The absolute pressure in the bottom was approx. 230 mbar; the top pressure was 100 mbar. For the purpose of polymerization inhibition, 52 l (STP)/h of air were fed in above the level of the bottoms.

Between the bottom of the vacuum distillation column and the influx of the product-laden stream from the bottom circuit of the stripping column into the vacuum distillation column were mounted first 6 bubble-capped trays (tray separation: 5 cm) and above them (above the influx) a further 15 bubble-capped trays (tray separation: 5 cm), above which the possibility of sampling by means of a miniature membrane metering pump existed.

Above this sampling point, 10 sieve trays (6 equidistant holes of diameter 6.5 mm per tray) were mounted (tray separation: 5 cm) which extended upward up to a collecting tray, from which approx. 364 g/h of purified acrylic acid were discharged continuously as the target product and stored after cooling in a stock vessel.

Secondary component contents of the target product were:

| | |
|---|---|
| acrylic acid (purity: without inhibitor content) | 99.54% by weight |
| all secondary component fractions below are reported here as weights based on the acrylic acid present | |

| | |
|---|---|
| acetic acid | 0.186% |
| propionic acid | 269 ppm |
| maleic anhydride | 406 ppm |
| formaldehyde | 344 ppm |
| benzaldehyde | 186 ppm |
| methacrylic acid | 1597 ppm |
| water | 342 ppm |

A further amount (732 ml/h) of acrylic acid discharged from the collecting tray was recycled into the distillation column while maintaining its withdrawal temperature of approx. 75° C. to the uppermost of the sieve trays disposed below the target product draw.

Above the target product discharge were disposed a further 10 sieve trays (6 holes of diameter 5.5 mm per tray, tray separation: 5 cm) which permitted low boilers which were still present to accumulate toward the top of the column. Above these sieve trays was mounted a further collecting tray in order to collect the low boiler condensate which occurs as a result of condensation caused by indirect cooling in the top of the column (26° C., absolute pressure 100 mbar). The temperature at the collecting tray was 73° C. The low boiler condensate comprised:

| | |
|---|---|
| acrylic acid | 98.42% by weight |
| acetic acid | 1.02% by weight |
| water | 0.427% by weight |
| methacrolein | 0.012% by weight |
| methacrylic acid | 0.021% by weight |
| Diphyl | 0.009% by weight |
| propionic acid | 0.024% by weight |
| furan-2-aldehyde | 0.010% by weight |
| allyl acrylate | 0.009% by weight |
| acrolein | 0.002% by weight |

From the total low boiler condensate stream withdrawn from the collecting tray, a main stream of 570 ml/h was fed as reflux back into the distillation column below the low boiler condensate collecting tray. The residual low boiler condensate stream of 190 ml/h which remained was cooled to 40° C. and fed to the acrylic acid absorption column above the 2nd segment thereof. To wet the walls for inhibition, a target product stream of 51 ml/h stabilized with 0.5% by weight of phenothiazine and having a temperature of 25° C. was sprayed in through a 4-hole full-jet nozzle in the uppermost region of the purifying column head.

The gas stream drawn off by means of a membrane vacuum pump at the top of the purifying column consisted mainly of inert gases and low boilers. In a cold trap cooled to 8° C., it was possible to remove from it another 4.6 g/h of condensable low boiler residual components. This residual component condensate separated in liquid form comprised:

| | |
|---|---|
| acrylic acid | 89.65% by weight |
| acetic acid | 2.45% by weight |
| water | 7.24% by weight |
| methacrolein | 0.197% by weight |
| methacrylic acid | 0.029% by weight |
| Diphyl | 0.059% by weight |
| propionic acid | 0.020% by weight |
| furan-3-aldehyde | 0.021% by weight |
| allyl acrylate | 0.007% by weight |
| acrolein | 0.037% by weight |

The "inert gas" stream remaining minus the residual component condensate had the following composition:

|  | % by volume |
|---|---|
| nitrogen | remainder to 100% |
| oxygen | 1.20 |
| propane | 18.8 |
| propene | 0.08 |
| methane | 0.004 |
| ethane | 0.052 |
| n-butane | 0.069 |
| isobutane | 0.146 |
| n-butene | 0 |
| isobutene | 0.0 |
| butadiene | 0.010 |
| carbon monoxide | 0.372 |
| carbon dioxide | 1.88 |
| ethene | 0.022 |

It was recycled into the 2nd segment of the absorption column above the pressure decoupling valve and below the Rhomopak packing disposed above it.

At the bottom of the purifying column, the absorbent freed substantially of acrylic acid was drawn off under level control and passed as the total absorbent stream having very low loading to the stainless steel pressure wash column already described, and the pressure increase of the bottoms circulation pump of the purifying column was utilized for discharge from the vacuum.

The absorbent having very low loading comprised:

|  | % by weight |
|---|---|
| acetic acid | 0.012 |
| furan-2-aldehyde | 0.0000 |
| propionic acid | 0.0000 |
| benzaldehyde | 0.097 |
| acrylic acid | 0.056 |
| methacrylic acid | 0.017 |
| Diphyl | 77.5 |
| DMP | 20.0 |
| benzoic acid | 0.642 |
| diacrylic acid | 0.910 |
| water | 0.0283 |

To reduce reactant losses and to achieve a high yield, all analysis gas streams laden with reactant or target product were combined in a glass vessel (0.5 liter) and fed by means of a small membrane pump to the first compressor stage of the secondary component discharge and combined with the cooled product gas mixture 1 of the dehydrogenation stage upstream of the compressor there and subsequently compressed. Based on converted propane, a yield of acrylic acid of 78.9 mol % was thus achieved.

Based on the propane and propylene present in product gas mixture 3, a recycle rate of >98 mol % into the first reaction stage was achieved both for the propane and for the propylene. In the case of a removal of acrylic acid from product gas mixture 3, in which product gas mixture 3, after direct and/or indirect cooling if appropriate, is fractionally condensed ascending in a column comprising separating internals with side draw removal of crude acrylic acid, and/or absorbed with water and/or aqueous solution, as described by way of example, by WO 2004/035514 and DE-A 10243625, the aforementioned recycle rates are generally >99.9 mol % and more. This is attributable to the fact that aqueous media substantially do not absorb propane and propylene and the oxidation cycle gas which thus escapes, for example, at the top of the column (residual gas) substantially quantitatively comprises unconverted propane and propylene. The crude acrylic acid withdrawn is further purified appropriately by means of suspension crystallization and subsequent wash column removal of the suspension crystals as described in the description of this document.

The crude acrylic acid obtained as the target product may be further purified by crystallization or rectification as described in the document EP-A 616998 (taking into account the teaching of EP-A 912486) or as described in the document DE-A 19606877 (the mother liquor may be recycled into the absorption column and/or into the purification column) or as described in the document EP-A 648732 to give glacial acrylic acid which can then be free-radically polymerized in a manner known per se to produce water-superabsorbent polymers. Both the crude acrylic acid obtained and the glacial acrylic acid obtained are outstandingly suitable for preparing esters of acrylic acid, for example for preparing alkyl acrylates.

It is essential to the invention that the process according to the invention is also suitable when the second reaction stage is carried out in a tube (bundle) reactor and the catalyst tube charge in the second reaction stage from top to bottom in flow direction of reaction gas mixture 2 is not configured as follows:

| | |
|---|---|
| Section A: | 50 cm-long preliminary bed of steatite rings (Steatite C220 from CeramTec) of geometry 7 mm × 7 mm × 4 mm (external diameter × length × internal diameter). |
| Section B: | 100 cm-long catalyst charge of homogeneous mixture of 30% by weight of steatite rings (Steatite C220 from CeramTec) of geometry 5 mm × 3 mm × 2 mm (external diameter × length × internal diameter) and 70% by weight of unsupported catalyst from section C. |
| Section C: | 170 cm-long catalyst charge of annular unsupported catalyst (5 mm × 3 mm × 2 mm = external diameter × length × internal diameter) according to example 1 of DE-A 10046957 |
| Section D: | 50 cm-long subsequent bed of steatite rings (Steatite C220 from CeramTec) of geometry 7 mm × 7 mm × 4 mm (external diameter × length × internal diameter). |

It is also essential to the invention that the process according to the invention is also suitable when the second reaction stage is carried out in a tube (bundle) reactor and, viewed over the reactor, salt melt and reaction gas mixture 2 are not conducted in countercurrent.

The aforementioned is especially true when the catalyst tube charge is not configured as described above.

The process according to the invention is also suitable when an intermediate oxygen feed is undertaken between the second and the third reaction stage.

The process according to the invention is also suitable when the third reaction stage is carried out in a tube (bundle) reactor and the catalyst tube charge from top to bottom in flow direction of reaction gas mixture 3 is not configured as follows:

| | |
|---|---|
| Section A: | 20 cm-long preliminary bed of steatite rings (Steatite C220 from CeramTec) of geometry 7 mm × 7 mm × 4 mm (external diameter × length × internal diameter) |
| Section B: | 100 cm-long catalyst charge of homogeneous or heterogeneous mixture of 30% by weight of steatite rings (Steatite C220 from CeramTec) of geometry 7 mm × 3 mm × 4 mm (external |

-continued

| | |
|---|---|
| | diameter × length × internal diameter) and 70% by weight of coated catalyst from section C. |
| Section C: | 200 cm-long catalyst charge of annular (7 mm × 3 mm × 4 mm = external diameter × length × internal diameter) coated catalyst according to preparation example 5 of DE-A 10046928 (or a coated catalyst (for example one prepared correspondingly) with the active composition $Mo_{12}V_{2.8}W_{1.2}Cu_{2.4}O_x$ or $Mo_{12}V_{3.5}W_{1.3}Cu_{2.4}O_x$). |
| Section D: | 50 cm-long subsequent bed of steatite rings (Steatite C220 from CeramTec) of geometry 7 mm × 7 mm × 4 mm (external diameter × length × internal diameter). |

It is also essential to the invention that the process according to the invention is also suitable when the third reaction stage is carried out in a tube (bundle) reactor and, viewed over the reactor, salt melt and reaction gas mixture 3 are not conducted in cocurrent.

The process according to the invention is also suitable when the second and the third reaction stage are carried out in one tube (bundle) reactor, and the catalyst tube charge from top to bottom in flow direction of the reaction gas mixtures in both reaction stages is not configured as described above.

The process according to the invention is also suitable when the second reaction stage and the third reaction stage are carried out in tube bundle reactors in which the heat carrier (the salt melt) flows in a meandering manner.

The process according to the invention is also suitable when neither an unsupported catalyst according to example 1 of DE-A 10046957, nor a catalyst according to the examples of DE-A 10351269 nor according to the examples or comparative examples of DE-A 10344149 is used in the second reaction stage.

The process according to the invention is also suitable when neither a coated catalyst according to preparation example 5 of DE-A 10046928 nor a coated catalyst (for example one prepared in a corresponding manner) with one of the active compositions $Mo_{12}V_{2.8}W_{1.2}Cu_{2.4}O_x$, $Mo_{12}V_{3.5}W_{1.3}Cu_{2.4}O_x$, nor a catalyst according to the examples of DE-A 10351269, DE-A 10360057 and DE-A 10360058 is used in the third reaction stage.

In particular, the process according to the invention is also suitable when the removal of the acrylic acid from product gas mixture 3 is not effected with an absorbent which comprises 57.4% by weight of diphenyl ether, 20.7% by weight of diphenyl and 20% by weight of dimethyl o-phthalate.

The process according to the invention is also suitable when it does not have any combination of the above negative features (in particular no combination of all negative features).

U.S. Provisional Patent Applications No. 60/584,469 (filed on Jul. 1, 2004), 60/656,875 (filed on Mar. 1, 2005) and 60/657,407 (filed on Mar. 2, 2005) are incorporated into the present application by literature reference. With regard to the abovementioned teachings, numerous alterations and deviations from the present invention are possible. It can therefore be assumed that the invention, within the scope of the appended claims, may be performed differently to the way specifically described herein.

What is claimed is:

1. A process for preparing acrylic acid by heterogeneously catalyzed partial gas phase oxidation of propylene, comprising:
   a) in a first reaction stage, subjecting propane to a heterogeneously catalyzed dehydrogenation in the presence of and/or with exclusion of oxygen to obtain a product gas mixture 1 comprising propane and propylene, and
   b) optionally, removing and/or converting to other compounds a portion of the constituents, other than propane and propylene, present in the product gas mixture 1 formed in the first reaction stage to obtain a product gas mixture 1' from product gas mixture 1, and
   c) in a second reaction stage, subjecting product gas mixture 1 and/or product gas mixture 1', as a constituent of a starting reaction gas mixture (2-a) which comprises molecular oxygen, molecular nitrogen, and propylene, wherein the molar ratio of $O_2:C_3H_6$ is $\geq 1$ and the molar ratio of $N_2:O_2$ ranges from 3 to 6, to a heterogeneously catalyzed partial gas phase oxidation of propylene present in product gas mixture 1 and/or product gas mixture 1' to acrolein in a second reaction stage charged with a fixed catalyst bed (2-b) whose catalysts have at least one multimetal oxide comprising the elements Mo, Fe and Bi as an active composition to obtain a product gas mixture (2-c), and
   d) optionally, lowering the temperature of the product gas mixture (2-c) leaving the second reaction stage by indirect and/or direct cooling and optionally, adding molecular oxygen and/or inert gas to product gas mixture (2-c), and then
   e) in a third reaction stage, subjecting product gas mixture (2-c), as a starting reaction gas mixture (3-a) which comprises acrolein, molecular oxygen and at least one inert gas and comprises molecular oxygen and acrolein in a molar $O_2:C_3H_4O$ ratio of $\geq 0.5$, to a heterogeneously catalyzed partial gas phase oxidation of acrolein present in starting reaction gas mixture (3-a) to acrylic acid in a third reaction stage charged with a fixed catalyst bed (3-b) whose catalysts have at least one multimetal oxide comprising the elements Mo and V as an active composition to obtain a product gas mixture (3-c), and
   f) removing acrylic acid in a separating zone A from product gas mixture (3-c) and recycling at least the unconverted propane and propylene present in product gas mixture (3-c) to an extent of in each case at least 90 mol % based on the particular amount present in product gas mixture (3-c) into at least the first of the three reaction stages, wherein
   the conversion $C^P$ of propylene in the second reaction stage, based on a single pass through it, ranges from 90 to 98 mol %, and
   the process has at least one separate discharge for constituents other than propane and propene and the content of propane and propene in that discharge is <1% by volume and the conversion $C^A$ of acrolein in the third reaction stage, based on a single pass through it, ranges from 99 to 99.9 mol %.

2. The process according to claim 1, wherein $C^A$ is $\geq 99.3$ mol %.

3. The process according to claim 1, wherein $C^A$ is $\geq 99.5$ mol %.

4. The process according to claim 1, wherein the unconverted propane and propylene present in product gas mixture (3-c) are recycled to an extent of in each case at least 92 mol % into at least the first reaction stage.

5. The process according to claim 1, wherein the unconverted propane and propylene present in product gas mixture (3-c) are recycled to an extent of in each case at least 94 mol % into at least the first reaction stage.

6. The process according to claim 1, wherein the unconverted propane and propylene present in product gas mixture (3-c) are recycled to an extent of in each case at least 95 mol % into at least the first reaction stage.

7. The process according to claim 1, wherein fresh propane is fed to at least one of the three reaction stages.

8. The process according to claim 1, wherein fresh propane is fed to reaction stage 2, or to reaction stage 3, or to both reaction stages.

9. The process according to claim 1, wherein starting gas mixture (2-a) comprises ≧7% by volume of propylene.

10. The process according to claim 1, wherein the molar ratio $V_1$ of propane present in starting reaction gas mixture (2-a) to propylene present in starting reaction gas mixture (2-a) is from 1 to 4.

11. The process according to claim 10, wherein $V_1$ is from 1 to 3.

12. The process according to claim 10, wherein $V_1$ is from 1 to 2.5.

13. The process according to claim 1, wherein starting reaction gas mixture (3-a) comprises ≧5.5% by volume of acrolein.

14. The process according to claim 13, wherein starting reaction gas mixture (3-a) comprises ≧6% by volume of acrolein.

15. The process according to claim 1, wherein the molar ratio $V_5$ of propane present in starting reaction gas mixture (3-a) to acrolein present therein is from 1 to 4.

16. The process according to claim 15, wherein $V_5$ is from 1.5 to 3.5.

17. The process according to claim 15, wherein $V_5$ is from 1.5 to 3.

18. The process according to claim 1, wherein starting reaction gas mixture (3-a) comprises:
from 6 to 8% by volume of acrolein,
from 6 to 9% by volume of molecular oxygen,
from 10 to 20% by volume of propane,
from 50 to 20% by volume of molecular nitrogen and
from 7 to 13% by volume of steam.

19. The process according to claim 1, wherein the hourly space velocity of propylene on fixed catalyst bed (2-a) is ≧140 l (STP)/l·h.

20. The process according to claim 1, wherein the hourly space velocity of acrolein on fixed catalyst bed (2-a) is ≧120 l (STP)/l·h.

21. The process according to claim 1, wherein reaction stage 1 is an autothermal heterogeneously catalyzed dehydrogenation.

22. The process according claim 1, wherein there is no intermediate oxygen feeding between reaction stages 2 and 3.

23. The process according to claim 1, wherein reaction stages 2 and 3 are carried out in a combined reactor.

24. The process according to claim 1, which is followed by a process in which product gas mixture (3-c) after optional direct and/or indirect cooling, is fractionally condensed as it rises in a column comprising separating internals with side draw removal of crude acrylic acid and/or absorbed with water and/or aqueous solution.

25. The process according to claim 24, which is followed by a process in which the crude acrylic acid is subjected to a suspension crystallization to form acrylic acid suspension crystals and remaining mother liquor.

26. The process according to claim 25, which is followed by a process in which the acrylic acid suspension crystals are removed from remaining mother liquor by means of a wash column.

27. The process according to claim 26, wherein the wash column is one which provides the forced transport of the crystal bed.

28. The process according to claim 26 or 27, wherein the wash column is a hydraulic wash column.

29. The process according to claim 26, wherein the washing liquid used is the melt of acrylic acid crystals which have been removed beforehand in the wash column.

30. The process according to claim 26, which is followed by a process in which the removed acrylic acid suspension crystals are melted and free-radically polymerized into polymers.

31. The process according to claim 1, wherein $C^P$ ranges from >90 to 98 mol % and $C^a$ ranges from >99 to 99.9 mol %.

32. The process according to claim 4, wherein $C^P$ ranges from >90 to 98 mol % and $C^a$ ranges from >99 to 99.9 mol %.

* * * * *